United States Patent
Cadden et al.

(10) Patent No.: US 10,632,012 B2
(45) Date of Patent: *Apr. 28, 2020

(54) SUSTAINED RELEASE DELIVERY OF ACTIVE AGENTS TO TREAT GLAUCOMA AND OCULAR HYPERTENSION

(71) Applicant: Mati Therapeutics Inc., Austin, TX (US)

(72) Inventors: Suzanne Cadden, North Vancouver (CA); Yong Hao, Vancouver (CA); Deepank Utkhede, Surrey (CA); Valery Rubinchik, Richmond (CA); Charles Richard Kjelbotn, Surrey (CA)

(73) Assignee: Mati Therapeutics Inc., Austin, TX (US)

( * ) Notice: Subject to any disclaimer, the term of this patent is extended or adjusted under 35 U.S.C. 154(b) by 446 days.

This patent is subject to a terminal disclaimer.

(21) Appl. No.: 15/478,220

(22) Filed: Apr. 3, 2017

(65) Prior Publication Data
US 2017/0202853 A1 Jul. 20, 2017

Related U.S. Application Data

(63) Continuation of application No. 14/136,024, filed on Dec. 20, 2013, now Pat. No. 9,610,271, which is a
(Continued)

(51) Int. Cl.
*A61F 9/00* (2006.01)
*A61K 9/00* (2006.01)
(Continued)

(52) U.S. Cl.
CPC ........ *A61F 9/0017* (2013.01); *A61F 9/00772* (2013.01); *A61F 9/00781* (2013.01);
(Continued)

(58) Field of Classification Search
CPC . A61K 31/5575; A61K 31/216; A61F 9/0017; A61F 9/00772; A61F 9/00781; A61F 9/0051; A61F 9/0092
See application file for complete search history.

(56) References Cited

U.S. PATENT DOCUMENTS 3,865,108 A 2/1975 Hartop
3,949,750 A 4/1976 Freeman
(Continued)

FOREIGN PATENT DOCUMENTS

AU 20023644336 7/2003
EP 0442745 A1 8/1991
(Continued)

OTHER PUBLICATIONS

Agarwal, et al., "Garg Textbook of Opthalmology Ed.", New Dehli, Jaypee Brothers Medical Publishing, (2002), 39-42.
(Continued)

*Primary Examiner* — Philip R Wiest
(74) *Attorney, Agent, or Firm* — Koren Anderson

(57) ABSTRACT

A method of decreasing intraocular pressure (IOP) in an eye of a patient in need thereof includes implanting a first lacrimal implant through a firsts punctum and into a first lacrimal canaliculus of the eye of the patient. The method may further comprise implanting a second lacrimal implant through a second punctum and into a second lacrimal canaliculus of the eye of the patient, and releasing, on a sustained basis a therapeutically effective amount of an intraocular pressure-reducing therapeutic agent.

30 Claims, 28 Drawing Sheets

Related U.S. Application Data continuation of application No. 13/598,573, filed on Aug. 29, 2012, now abandoned.

(60) Provisional application No. 61/644,397, filed on May 8, 2012, provisional application No. 61/528,736, filed on Aug. 29, 2011.

(51) Int. Cl.
  *A61F 9/007* (2006.01)
  *A61K 31/216* (2006.01)
  *A61K 31/5575* (2006.01)

(52) U.S. Cl.
  CPC .......... *A61K 9/0051* (2013.01); *A61K 9/0092* (2013.01); *A61K 31/216* (2013.01); *A61K 31/5575* (2013.01)

(56) References Cited

U.S. PATENT DOCUMENTS

| | | | |
|---|---|---|---|
| 4,014,335 A | 3/1977 | Arnold |
| 4,281,654 A | 8/1981 | Shell |
| 4,304,765 A | 12/1981 | Shell |
| 4,540,408 A | 9/1985 | Lloyd |
| 4,660,546 A | 4/1987 | Herrick |
| 4,747,404 A | 5/1988 | Jampel |
| 4,886,488 A | 12/1989 | White |
| 4,915,684 A | 4/1990 | MacKeen |
| 4,959,048 A | 9/1990 | Seder |
| 5,041,081 A | 8/1991 | Odrich |
| 5,049,142 A | 9/1991 | Herrick |
| 5,053,030 A | 10/1991 | Herrick |
| 5,128,058 A | 7/1992 | Ishii |
| 5,133,159 A | 7/1992 | Nelson |
| 5,163,959 A | 11/1992 | Herrick |
| 5,171,270 A | 12/1992 | Herrick |
| 5,254,089 A | 10/1993 | Wang |
| 5,283,063 A | 2/1994 | Freeman |
| 5,318,513 A | 6/1994 | Leib |
| 5,334,137 A | 8/1994 | Freeman |
| 5,395,618 A | 3/1995 | Darougar |
| 5,417,651 A | 5/1995 | Guena |
| 5,423,777 A | 6/1995 | Tajiri |
| 5,466,233 A | 11/1995 | Weiner |
| 5,556,633 A | 9/1996 | Haddad |
| 5,707,643 A | 1/1998 | Ogura |
| 5,723,005 A | 3/1998 | Herrick |
| 5,741,292 A | 4/1998 | Mendius |
| 5,766,243 A | 6/1998 | Christensen |
| 5,770,589 A | 6/1998 | Billson |
| 5,773,019 A | 6/1998 | Ashton |
| 5,824,073 A | 10/1998 | Peyman |
| 5,826,584 A | 10/1998 | Schmitt |
| 5,830,171 A | 11/1998 | Wallace |
| 5,840,054 A | 11/1998 | Hamano |
| 5,902,598 A | 5/1999 | Chen |
| 5,928,662 A | 7/1999 | Phillips |
| 5,947,974 A | 9/1999 | Brady |
| 5,961,370 A | 10/1999 | Valle |
| 5,962,383 A | 10/1999 | Doyel |
| 5,993,407 A | 11/1999 | Moazed |
| 6,010,391 A | 1/2000 | Lewellen |
| 6,016,806 A | 1/2000 | Webb |
| 6,027,470 A | 2/2000 | Mendius |
| 6,041,785 A | 3/2000 | Webb |
| 6,082,362 A | 7/2000 | Webb |
| 6,095,901 A | 8/2000 | Robinson |
| 6,149,684 A | 11/2000 | Herrick |
| 6,196,993 B1 | 3/2001 | Cohan |
| 6,225,348 B1 | 5/2001 | Paulsen |
| 6,234,175 B1 | 5/2001 | Zhou |
| 6,238,363 B1 | 5/2001 | Kurihashi |
| 6,254,562 B1 | 7/2001 | Fouere |
| 6,264,971 B1 | 7/2001 | Darougar |
| 6,290,684 B1 | 9/2001 | Herrick |
| 6,306,114 B1 | 10/2001 | Freeman |
| 6,331,313 B1 | 12/2001 | Wong |
| 6,344,047 B1 | 2/2002 | Price |
| 6,371,122 B1 | 4/2002 | Mandelkorn |
| 6,375,972 B1 | 4/2002 | Guo |
| 6,383,192 B1 | 5/2002 | Kurihashi |
| 6,416,780 B1 | 7/2002 | Passmore |
| 6,428,502 B1 | 8/2002 | Lang |
| 6,455,062 B1 | 9/2002 | Olejnik |
| 6,534,693 B2 | 3/2003 | Fischell |
| 6,605,108 B2 | 8/2003 | Mendius |
| 6,629,533 B1 | 10/2003 | Webb |
| 6,645,963 B2 | 11/2003 | Higashiyama |
| 6,706,275 B1 | 3/2004 | Camp |
| 6,729,939 B2 | 5/2004 | Wrue |
| 6,756,049 B2 | 6/2004 | Brubaker |
| 6,780,164 B2 | 8/2004 | Bergheim |
| 6,840,931 B2 | 1/2005 | Peterson |
| 6,846,318 B2 | 1/2005 | Camp |
| 6,866,563 B2 | 3/2005 | Green |
| 6,964,781 B2 | 11/2005 | Brubaker |
| 6,982,090 B2 | 1/2006 | Gillespie |
| 6,991,808 B2 | 1/2006 | Brubaker |
| 6,994,684 B2 | 2/2006 | Murray |
| 7,017,580 B2 | 3/2006 | Prescott |
| 7,117,870 B2 | 10/2006 | Prescott |
| 7,135,009 B2 | 11/2006 | Tu |
| 7,204,253 B2 | 4/2007 | Mendius |
| 7,204,995 B2 | 4/2007 | El-Sherif |
| 7,510,541 B2 | 3/2009 | Hanna |
| 7,662,864 B2 | 2/2010 | Kanamathareddy |
| 7,998,497 B2 | 8/2011 | de Juan |
| 8,333,726 B2 | 12/2012 | Rapacki et al. |
| 8,691,265 B2 | 4/2014 | de Juan |
| 8,702,643 B2 | 4/2014 | Rapacki et al. |
| 8,795,711 B2 | 8/2014 | de Juan |
| 9,610,271 B2 * | 4/2017 | Cadden ................ A61K 9/0051 |
| 9,974,685 B2 * | 5/2018 | Cadden ................ A61F 9/0017 |
| 2002/0028181 A1 | 3/2002 | Miller |
| 2002/0032400 A1 | 3/2002 | Moazed |
| 2002/0055701 A1 | 5/2002 | Fischell |
| 2002/0151960 A1 | 10/2002 | Mendius |
| 2002/0198453 A1 | 12/2002 | Herrick |
| 2003/0130612 A1 | 7/2003 | Moazed |
| 2003/0152522 A1 | 8/2003 | Miller |
| 2004/0043067 A1 | 3/2004 | Salamone |
| 2004/0071761 A1 | 4/2004 | Miller |
| 2004/0092435 A1 | 5/2004 | Peyman |
| 2004/0102729 A1 | 5/2004 | Haffner |
| 2004/0116524 A1 | 6/2004 | Cohen |
| 2004/0121014 A1 | 6/2004 | Guo |
| 2004/0127843 A1 | 7/2004 | Tu |
| 2004/0137068 A1 | 7/2004 | Bhushan |
| 2004/0141151 A1 | 7/2004 | Gillespie |
| 2004/0144392 A1 | 7/2004 | Mueller |
| 2004/0147870 A1 | 7/2004 | Burns |
| 2004/0170685 A1 | 9/2004 | Carpenter |
| 2004/0175410 A1 | 9/2004 | Ashton |
| 2004/0176341 A1 | 9/2004 | Chou |
| 2004/0208910 A1 | 10/2004 | Ashton |
| 2004/0210182 A1 | 10/2004 | Fouere |
| 2004/0236343 A1 | 11/2004 | Taylor |
| 2004/0249333 A1 | 12/2004 | Bergheim |
| 2004/0254516 A1 | 12/2004 | Murray |
| 2004/0265356 A1 | 12/2004 | Mosack |
| 2005/0048121 A1 | 3/2005 | East |
| 2005/0095269 A1 | 5/2005 | Ainpour |
| 2005/0107734 A1 | 5/2005 | Coroneo |
| 2005/0129731 A1 | 6/2005 | Horres |
| 2005/0192527 A1 | 9/2005 | Gharib |
| 2005/0197614 A1 | 9/2005 | Pritchard |
| 2005/0220882 A1 | 10/2005 | Pritchard |
| 2005/0232972 A1 | 10/2005 | Odrich |
| 2005/0244469 A1 | 11/2005 | Whitcup |
| 2005/0244506 A1 | 11/2005 | Burke |
| 2005/0255564 A1 | 11/2005 | Sakai |
| 2005/0266047 A1 | 12/2005 | Tu |
| 2005/0271704 A1 | 12/2005 | Tu |

(56) References Cited

U.S. PATENT DOCUMENTS

| | | |
|---|---|---|
| 2005/0283109 A1 | 12/2005 | Peyman |
| 2006/0013835 A1 | 1/2006 | Anderson |
| 2006/0020248 A1 | 1/2006 | Prescott |
| 2006/0020253 A1 | 1/2006 | Prescott |
| 2006/0074370 A1 | 4/2006 | Zhou |
| 2006/0100700 A1 | 5/2006 | Bernard |
| 2006/0106352 A1 | 5/2006 | Kurihashi |
| 2006/0122553 A1 | 6/2006 | Hanna |
| 2007/0021762 A1 | 1/2007 | Liu |
| 2007/0083146 A1 | 4/2007 | Murray |
| 2007/0123924 A1 | 5/2007 | Becker |
| 2007/0132125 A1 | 6/2007 | Rastogi |
| 2007/0135914 A1 | 6/2007 | Herrick |
| 2007/0243230 A1 | 10/2007 | de Juan |
| 2007/0269487 A1 | 11/2007 | de Juan |
| 2007/0298075 A1 | 12/2007 | Borgia |
| 2007/0299515 A1 | 12/2007 | Herrick |
| 2007/0299516 A1 | 12/2007 | Cui |
| 2008/0038317 A1 | 2/2008 | Chang |
| 2008/0045878 A1 | 2/2008 | Bergheim |
| 2008/0045911 A1 | 2/2008 | Borgia |
| 2008/0181930 A1 | 7/2008 | Rodstrom |
| 2008/0299176 A1 | 12/2008 | Lai |
| 2009/0092654 A1 | 4/2009 | de Juan |
| 2009/0099626 A1 | 4/2009 | de Juan |
| 2009/0104243 A1 | 4/2009 | Utkhede |
| 2009/0104248 A1 | 4/2009 | Rapacki |
| 2009/0105749 A1 | 4/2009 | de Juan |
| 2009/0118702 A1 | 5/2009 | Lazar |
| 2009/0264861 A1 | 10/2009 | Jain |
| 2009/0280158 A1 | 11/2009 | Butuner |
| 2009/0281621 A1 | 11/2009 | Becker |
| 2009/0298390 A1 | 12/2009 | Rapacki |
| 2010/0034870 A1 | 2/2010 | Sim |
| 2010/0189766 A1 | 7/2010 | Utkhede |
| 2010/0209477 A1 | 8/2010 | Butuner |
| 2010/0274204 A1 | 10/2010 | Rapacki |
| 2010/0274224 A1 | 10/2010 | Jain |
| 2014/0161863 A1 | 6/2014 | de Juan |
| 2014/0180253 A1 | 6/2014 | Rapacki et al. |

FOREIGN PATENT DOCUMENTS

| | | |
|---|---|---|
| EP | 0621022 | 7/1999 |
| EP | 0988844 A2 | 3/2000 |
| GB | 2216795 A | 10/1989 |
| JP | 7178130 A | 7/1995 |
| JP | 10033584 A | 2/1998 |
| JP | 11505159 A | 5/1999 |
| JP | 2004202276 A | 7/2004 |
| JP | 2005000628 A | 1/2005 |
| JP | 2005058622 A | 3/2005 |
| JP | 2005110765 A | 4/2005 |
| JP | 2005110930 A | 4/2005 |
| JP | 2005312835 A | 11/2005 |
| JP | 2005319190 A | 11/2005 |
| JP | 2005328922 A | 12/2005 |
| JP | 2007195819 A | 8/2007 |
| NZ | 581461 A | 4/2011 |
| WO | WO-1993012765 | 7/1993 |
| WO | WO-1995001764 | 1/1995 |
| WO | WO-1995028984 | 11/1995 |
| WO | WO-1997011655 | 4/1997 |
| WO | WO-1998033461 | 8/1998 |
| WO | WO-1998042282 | 10/1998 |
| WO | WO-1999037260 | 7/1999 |
| WO | WO-1999044553 | 9/1999 |
| WO | WO-1999064089 | 12/1999 |
| WO | WO-1999065544 | 12/1999 |
| WO | WO-2000027321 | 5/2000 |
| WO | WO-2000062760 | 10/2000 |
| WO | WO-2001080825 | 11/2001 |
| WO | WO-2002011783 | 2/2002 |
| WO | WO-2002058667 | 8/2002 |
| WO | WO-2003017897 | 3/2003 |
| WO | WO-2003022242 | 3/2003 |
| WO | WO-2003057101 | 7/2003 |
| WO | WO-2004004614 | 1/2004 |
| WO | WO-2004024043 | 3/2004 |
| WO | WO-2004105658 | 12/2004 |
| WO | WO-2004112639 | 12/2004 |
| WO | WO-2005000154 | 1/2005 |
| WO | WO-2005086694 | 9/2005 |
| WO | WO-2006014434 | 2/2006 |
| WO | WO-2006014793 | 2/2006 |
| WO | WO-2006031658 | 3/2006 |
| WO | WO-2006044669 | 4/2006 |
| WO | WO-2006057859 | 6/2006 |
| WO | WO-2006096586 | 9/2006 |
| WO | WO-2006122414 | 11/2006 |
| WO | WO-2007008262 | 1/2007 |
| WO | WO-2007115259 | 10/2007 |
| WO | WO-2007115261 | 10/2007 |
| WO | WO-2007149771 | 12/2007 |
| WO | WO-2007149832 | 12/2007 |
| WO | WO-2008056060 | 5/2008 |
| WO | WO-2008094989 | 8/2008 |
| WO | WO-2009032328 | 3/2009 |
| WO | WO-2009035562 | 3/2009 |
| WO | WO-2009035565 | 3/2009 |
| WO | WO-2009137085 | 11/2009 |
| WO | WO-2010008883 | 1/2010 |
| WO | WO-2010096822 | 8/2010 |
| WO | WO-2010085696 | 6/2011 |
| WO | WO-2011066479 | 6/2011 |

OTHER PUBLICATIONS

Anand, Aashish, et al., "Sequential Glaucoma Implants in Refractory Glaucoma", Am. J. Ophtalm, 149(1), (Jan. 2010), 95-101.

"U.S. Appl. No. 10/825,047, Preliminary Amendment and Response filed Aug. 18, 2008 to Restriction Requirement dated Jul. 17, 2008", 10 pgs.

"U.S. Appl. No. 10/825,047, Response filed Apr. 22, 2009 to Non Final Office Action dated Oct. 22, 2008", 17 pgs.

"U.S. Appl. No. 10/825,047, Final Office Action dated Jun. 9, 2009", 14 pgs.

"U.S. Appl. No. 11/695,537, Non Final Office Action dated Sep. 18, 2009", 12 pgs.

"U.S. Appl. No. 11/695,537, Response filed Dec. 17, 2008 to Office Communication dated Nov. 28, 2008", 8 pgs.

"U.S. Appl. No. 11/695,537, Restriction Requirement dated Oct. 3, 2008", 10 pgs.

"U.S. Appl. No. 11/695,545, Preliminary Amendment and Response filed Nov. 6, 2008 to Restriction Requirement dated Oct. 6, 2008", 14 pgs.

"U.S. Appl. No. 11/695,545, Restriction Requirement dated Oct. 6, 2008", 10 pgs.

"U.S. Appl. No. 12/604,202, Preliminary Amendment filed Nov. 30, 2009", 6 pgs.

"Australian Application No. 2007234445, Examiner Report dated Oct. 12, 2009", 2 pgs.

"Australian Application Serial No. 2007234447, Examiner Report dated Oct. 6, 2009", 3 pgs.

"Canadian Application Serial No. 2,648,066, Office Action dated Nov. 1, 2010".

"Chinese Application Serial No. 200580028979.2, First Office Action dated Dec. 12, 2008", 7 pgs.

"Chinese Application Serial No. 200780017166.2, Second Office Action dated Mar. 6, 2012".

CRISP, "Time Release Ophthalmic Drug Delivery Insert", Abstract for Grant No. 1R43EY012916-01; [Online]. Retrieved from the Internet: <http://crisp.cit.nih.gov.crisp/CRISP LIB.getdoc?textkey+ 6073940&p grant num = 1R43EY012916-01&p query=&ticket= 63935662&p audit session id=325068793&p keyWO-rds=, 1 pg.

"European Application No. 08330451.4. Examination Report dated Nov. 5, 2010".

"European Application Serial No. 05768122.3. Office Action dated Mar. 31, 2009", 3 pgs.

(56) References Cited

OTHER PUBLICATIONS

"European Serial No. 12827871.0, European Extended Search Report dated Feb. 13, 2015", 6 pgs.
Gulsen, Derya, "Dispersion of DMPC Liposomes in Contact Lenses for Ophthalmic Drug Delivery", 30 Curr. Eye Res, 1071, (2005).
"International Application Serial No. PCT/IB2012/002210, International Preliminary Report on Patentability dated Feb. 25, 2013", 6 pgs.
"International Application Serial No. PCT/IB2012/002210, International Search Report dated Feb. 25, 2013", 5 pgs.
"International Application Serial No. PCT/IB2012/002210, Written Opinion dated Feb. 18, 2013", 5 pgs.
"International Application Serial No. PCT/US07/65792, International Search Report dated Nov. 20, 2008", 2 pgs.
"International Application Serial No. PCT/US07/65792, International Written Opinion dated Nov. 20, 2008", 5 pgs.
"International Application Serial No. PCT/US2007/065789, International Search Report dated Aug. 13, 2008", 3 pgs.
"International Application Serial No. PCT/US2007/065789, Written Opinion dated Aug. 13, 2008", 5 pgs.
"International Application Serial No. PCT/US2008/010487, International Search Report dated May 25, 2009", 5 pgs.
"International Application Serial No. PCT/US2008/010487, Written Opinion dated May 25, 2009", 8 pgs.
"International Application Serial No. PCT/US2008/010497, International Search Report dated Mar. 6, 2009".
"International Application Serial No. PCT/US2008/010497, Written Opinion dated Mar. 6, 2009".
"International Application Serial No. PCT/US2008/010502, International Search Report dated Mar. 5, 2009".
"International Application Serial No. PCT/US2008/010502, Written Opinion dated Mar. 5, 2009".
"International Application Serial No. PCT/US2009/002854, International Preliminary Report on Patentability dated Nov. 18, 2010".
"International Application Serial No. PCT/US2009/002854, International Search Report dated May 3, 2010".
"International Application Serial No. PCT/US2009/002854, Written Opinion dated May 3, 2010".
"International Application Serial No. PCT/US2010/021868, International Preliminary Report on Patentability dated Aug. 4, 2011".
"International Application Serial No. PCT/US2010/025089, International Preliminary Report on Patentability dated Sep. 1, 2011".
"International Application Serial No. PCT/US2010/025089, International Search Report dated Dec. 10, 2010".
"International Application Serial No. PCT/US2010/025089, Written Opinion dated Dec. 10, 2010".
"Israeli Application Serial No. 194514, Notice of Defects dated Sep. 12, 2011".
"Israeli Application Serial No. 212114, Notice of Defects dated Sep. 12, 2011".
"Japanese Application Serial No. 2009-503334, Notice of Rejection dated Aug. 30, 2011".
"Japanese Application Serial No. 2009-503335, Decision of Rejection dated Apr. 3, 2012".
"Korean Application Serial No. 10-2008-7026758, Office Action dated Oct. 25, 2010".
"Korean Application Serial No. 10-2008-7026781, Office Action dated Aug. 26, 2010".
"New Zealand Application Serial No. 571758, Examination Report dated May 24, 2010", 2 pgs.
"New Zealand Application Serial No. 571758, Examination Report dated Nov. 14, 2011".
Shah, et al., "Shunt revision versus additional tube shunt implantation after failed tube shunt surgery in refractory glaucoma", Am. J. Ophtalm, 129(4), (Apr. 1, 2000), 455-460.
International Application Serial No. PCT/IB2013/000694, International Preliminary Report on Patentability, dated Nov. 4, 2014, 6 pages.
International Application Serial No. PCT/IB2013/000694, International Search Report, dated Aug. 21, 2013, 4 pages.
International Application Serial No. PCT/IB2013/000694, Written Opinion, dated Aug. 21, 2013, 5 pages.

\* cited by examiner

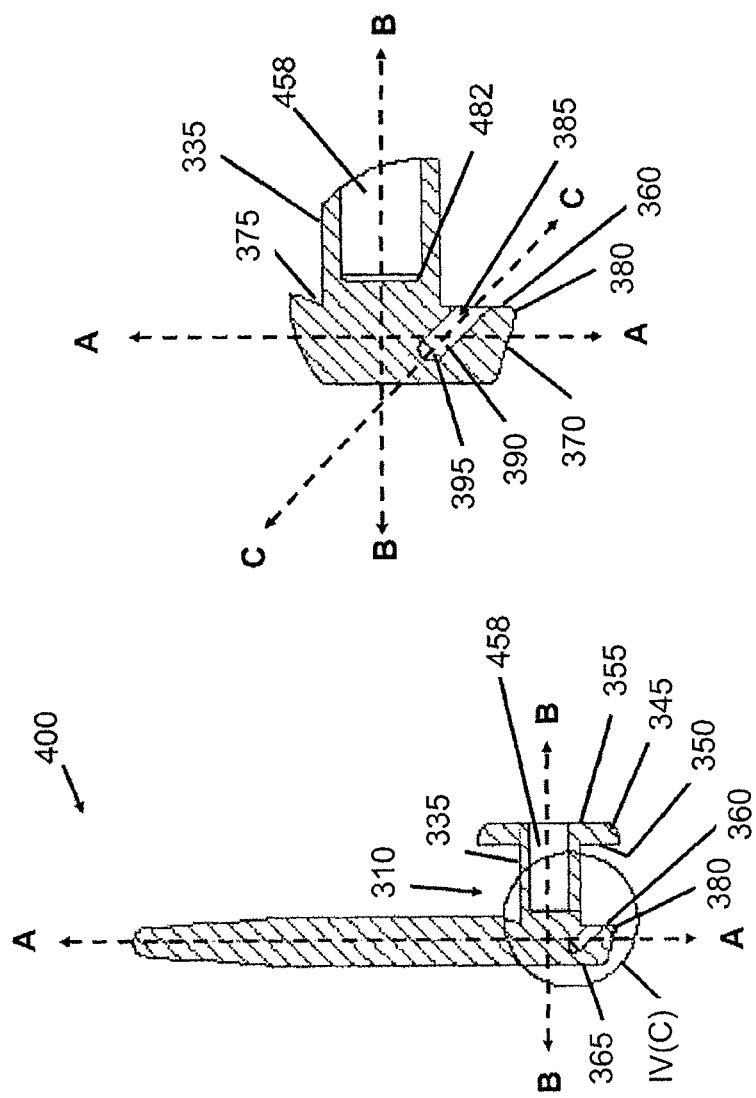

| Punctum Size Day 0 | | Example 1 Implant 300 (L68) 40D | Example 2 Implant 400 (L65) 40D | Example 3 Implant 500 (L67) 40D | Example 4 Implant 600 (L60) 40D | Example 5 Implant 600 (L63) 70D | Example 6 Implant 700 (L66) 70D | Example 7 Implant 800 (L61) 40D | Example 8 Implant 900 (L64) 70D | Example 9 Implant 1000 (L69) 70D | Example 10 Implant 1100 (L75) 70D | Example 11 Implant 1200 (L72) 70D |
|---|---|---|---|---|---|---|---|---|---|---|---|---|
| | | | (N=32) | | (N=72) | (N=85) | (N=28) | (N=33) | | | | |
| ~0.5 mm | n | | 0 | | 5 | 2 | 4 | 2 | | | | |
| | Yes | | 0 | | 5 (100%) | 2 (100%) | 4 (100%) | 2 (100%) | | | | |
| | No | | 0 | | 0 | 0 | 0 | 0 | | | | |
| 0.6 mm | n | | 3 | | 14 | 21 | 4 | 7 | | | | |
| | Yes | | 3 (100%) | | 14 (100%) | 21 (100%) | 4 (100%) | 7 (100%) | | | | |
| | No | | 0 | | 0 | 0 | 0 | 0 | | | | |
| 0.7 mm | n | | 11 | | 12 | 9 | 6 | 12 | | | | |
| | Yes | | 11 (100%) | | 12 (100%) | 9 (100%) | 6 (100%) | 12 (100%) | | | | |
| | No | | 0 | | 0 | 0 | 0 | 0 | | | | |
| ~0.8 mm | n | | 10 | | 38 | 35 | 12 | 10 | | | | |
| | Yes | | 10 (100%) | | 38 (100%) | 35 (100%) | 12 (100%) | 10 (100%) | | | | |
| | No | | 0 | | 0 | 0 | 0 | 0 | | | | |
| Total | n | | 24 | | 69 | 67 | 26 | 31 | | | | |
| | Yes | | 24 (100%) | | 69 (100%) | 67 (100%) | 26 (100%) | 31 (100%) | | | | |
| | No | | 0 | | 0 | 0 | 0 | 0 | | | | |

Table 1

FIG. 8A

| Punctum Size Day 1 | | Example 1 Implant 300 (L68) 40D | Example 2 Implant 400 (L65) 40D | Example 3 Implant 500 (L67) 40D | Example 4 Implant 600 (L60) 40D | Example 5 Implant 600 (L63) 70D | Example 6 Implant 700 (L66) 70D | Example 7 Implant 800 (L61) 40D | Example 8 Implant 900 (L64) 70D | Example 9 Implant 1000 (L69) 70D | Example 10 Implant 1100 (L75) 70D | Example 11 Implant 1200 (L72) 70D |
|---|---|---|---|---|---|---|---|---|---|---|---|---|
| | | (N=32) | | | (N=72) | (N=85) | (N=28) | (N=33) | | | | |
| ~0.5 mm | n | 0 | 0 | | 5 | 2 | 4 | 2 | | | | |
| | Yes | 0 | 0 | | 5 (100%) | 2 (100%) | 4 (100%) | 2 (100%) | | | | |
| | No | 0 | 0 | | 0 | 0 | 0 | 0 | | | | |
| 0.6 mm | n | | 3 | | 14 | 21 | 4 | 7 | | | | |
| | Yes | | 3 (100%) | | 14 (100%) | 21 (100%) | 4 (100%) | 7 (100%) | | | | |
| | No | | 0 | | 0 | 0 | 0 | 0 | | | | |
| 0.7 mm | n | | 11 | | 12 | 9 | 6 | 12 | | | | |
| | Yes | | 11 (100%) | | 12 (100%) | 9 (100%) | 6 (100%) | 12 (100%) | | | | |
| | No | | 0 | | 0 | 0 | 0 | 0 | | | | |
| ~0.8 mm | n | | 10 | | 38 | 35 | 12 | 10 | | | | |
| | Yes | | 10 (100%) | | 37 (97%) | 35 (100%) | 12 (100%) | 10 (100%) | | | | |
| | No | | 0 | | 1 (3%) | 0 | 0 | 0 | | | | |
| Total | n | | 24 | | 69 | 67 | 26 | 31 | | | | |
| | Yes | | 24 (100%) | | 68 (99%) | 67 (100%) | 26 (100%) | 31 (100%) | | | | |
| | No | | 0 | | 1 (1%) | 0 | 0 | 0 | | | | |

Table 2

FIG. 8B

| Punctum Size Week 1 | | Example 1 Implant 300 (L68) 40D | Example 2 Implant 400 (L65) 40D | Example 3 Implant 500 (L67) 40D | Example 4 Implant 600 (L60) 40D | Example 5 Implant 600 (L63) 70D | Example 6 Implant 700 (L66) 70D | Example 7 Implant 800 (L61) 40D | Example 8 Implant 900 (L64) 70D | Example 9 Implant 1000 (L69) 70D | Example 10 Implant 1100 (L75) 70D | Example 11 Implant 1200 (L72) 70D |
|---|---|---|---|---|---|---|---|---|---|---|---|---|
| | | (N=32) | | | (N=72) | (N=85) | (N=28) | (N=33) | | | | |
| ~0.5 mm | n | 0 | | | 5 | 2 | 2 | 2 | | | | |
| | Yes | 0 | | | 5 (100%) | 2 (100%) | 2 (100%) | 2 (100%) | | | | |
| | No | 0 | | | 0 | 0 | 0 | 0 | | | | |
| 0.6 mm | n | | 3 | | 14 | 21 | 4 | 7 | | | | |
| | Yes | | 3 (100%) | | 14 (100%) | 21 (100%) | 4 (100%) | 7 (100%) | | | | |
| | No | | 0 | | 0 | 0 | 0 | 0 | | | | |
| 0.7 mm | n | | 11 | | 11 | 9 | 6 | 12 | | | | |
| | Yes | | 11 (100%) | | 10 (91%) | 9 (100%) | 6 (100%) | 12 (100%) | | | | |
| | No | | 0 | | 1 (9%) | 0 | 0 | 0 | | | | |
| ~0.8 mm | n | | 10 | | 38 | 35 | 12 | 10 | | | | |
| | Yes | | 10 (100%) | | 37 (97%) | 35 (100%) | 12 (100%) | 10 (100%) | | | | |
| | No | | 0 | | 1 (3%) | 0 | 0 | 0 | | | | |
| Total | n | | 24 | | 68 | 67 | 24 | 31 | | | | |
| | Yes | | 24 (100%) | | 66 (97%) | 67 (100%) | 24 (100%) | 31 (100%) | | | | |
| | No | | 0 | | 2 (3%) | 0 | 0 | 0 | | | | |

Table 3

FIG. 8C

| Punctum Size Week 2 | | Example 1 Implant 300 (L68) 40D | Example 2 Implant 400 (L65) 40D | Example 3 Implant 500 (L67) 40D | Example 4 Implant 600 (L60) 40D | Example 5 Implant 600 (L63) 70D | Example 6 Implant 700 (L66) 70D | Example 7 Implant 800 (L61) 40D | Example 8 Implant 900 (L64) 70D | Example 9 Implant 1000 (L69) 70D | Example 10 Implant 1100 (L75) 70D | Example 11 Implant 1200 (L72) 70D |
|---|---|---|---|---|---|---|---|---|---|---|---|---|
| | | (N=32) | | | (N=72) | (N=85) | (N=28) | (N=33) | | | | |
| ~0.5 mm | n | 0 | 0 | | 5 | 2 | 2 | 2 | | | | |
| | Yes | | 0 | | 5 (100%) | 2 (100%) | 2 (100%) | 2 (100%) | | | | |
| | No | 0 | 0 | | 0 | 0 | 0 | 0 | | | | |
| 0.6 mm | n | | 3 | | 14 | 21 | 4 | 7 | | | | |
| | Yes | | 3 (100%) | | 14 (100%) | 21 (100%) | 2 (50%) | 7 (100%) | | | | |
| | No | | 0 | | 0 | 0 | 2 (50%) | 0 | | | | |
| 0.7 mm | n | | 11 | | 11 | 9 | 6 | 12 | | | | |
| | Yes | | 11 (100%) | | 10 (91%) | 9 (100%) | 5 (100%) | 10 (83%) | | | | |
| | No | | 0 | | 1 (9%) | 0 | 1 | 2 (17%) | | | | |
| ~0.8 mm | n | | 10 | | 38 | 35 | 12 | 10 | | | | |
| | Yes | | 10 (100%) | | 36 (95%) | 35 (100%) | 12 (100%) | 9 (90%) | | | | |
| | No | | 0 | | 2 (5%) | 0 | 0 | 1 (10%) | | | | |
| Total | n | | 24 | | 68 | 67 | 24 | 31 | | | | |
| | Yes | | 24 (100%) | | 65 (96%) | 67 (100%) | 21 (88%) | 28 (90%) | | | | |
| | No | | 0 | | 3 (4%) | 0 | 3 (13%) | 3 (10%) | | | | |

Table 4

FIG. 8D

| Punctum Size Week 4 | | Example 1 Implant 300 (L68) 40D | Example 2 Implant 400 (L65) 40D (N=32) | Example 3 Implant 500 (L67) 40D | Example 4 Implant 600 (L60) 40D (N=72) | Example 5 Implant 600 (L63) 70D (N=85) | Example 6 Implant 700 (L66) 70D (N=28) | Example 7 Implant 800 (L61) 40D (N=33) | Example 8 Implant 900 (L64) 70D | Example 9 Implant 1000 (L69) 70D | Example 10 Implant 1100 (L75) 70D | Example 11 Implant 1200 (L72) 70D |
|---|---|---|---|---|---|---|---|---|---|---|---|---|
| 0.5 mm | n | | 0 | | 5 | 2 | 2 | 2 | | | | |
| | Yes | | 0 | | 4 (80%) | 2 (100%) | 2 (100%) | 2 (100%) | | | | |
| | No | | 0 | | 1 (20%) | 0 | 0 | 0 | | | | |
| 0.6 mm | n | | 3 | | 12 | 21 | 4 | 7 | | | | |
| | Yes | | 3 (100%) | | 12 (100%) | 21 (100%) | 2 (50%) | 6 (86%) | | | | |
| | No | | 0 | | 0 | 0 | 2 (50%) | 1 (14%) | | | | |
| 0.7 mm | n | | 11 | | 10 | 9 | 5 | 12 | | | | |
| | Yes | | 10 (91%) | | 9 (90%) | 9 (100%) | 4 (80%) | 10 (83%) | | | | |
| | No | | 1 (9%) | | 1 (10%) | 0 | 1 (20%) | 2 (17%) | | | | |
| 0.8 mm | n | | 10 | | 38 | 35 | 9 | 10 | | | | |
| | Yes | | 10 (100%) | | 34 (89%) | 34 (97%) | 9 (100%) | 9 (90%) | | | | |
| | No | | 0 | | 4 (11%) | 1 (3%) | 0 | 1 (10%) | | | | |
| Total | n | | 24 | | 65 | 67 | 20 | 31 | | | | |
| | Yes | | 23 (96%) | | 59 (91%) | 66 (99%) | 17 (85%) | 27 (87%) | | | | |
| | No | | 1 (4%) | | 6 (9%) | 1 (1%) | 3 (15%) | 4 (13%) | | | | |

Table 5

FIG. 8E

| Punctum Size Week 8 | | Example 1 Implant 300 (L68) 40D | Example 2 Implant 400 (L65) 40D | Example 3 Implant 500 (L67) 40D | Example 4 Implant 600 (L60) 40D | Example 5 Implant 600 (L63) 70D | Example 6 Implant 700 (L66) 70D | Example 7 Implant 800 (L61) 40D | Example 8 Implant 900 (L64) 70D | Example 9 Implant 1000 (L69) 70D | Example 10 Implant 1100 (L75) 70D | Example 11 Implant 1200 (L72) 70D |
|---|---|---|---|---|---|---|---|---|---|---|---|---|
| | | (N=32) | | | (N=72) | (N=85) | (N=28) | (N=33) | | | | |
| ~0.5 mm | n | 0 | | | 5 | 2 | 2 | 2 | | | | |
| | Yes | 0 | | | 4 (80%) | 1 (50%) | 2 (100%) | 2 (100%) | | | | |
| | No | 0 | | | 1 (20%) | 1 (50%) | 0 | 0 | | | | |
| 0.6 mm | n | 3 | | | 12 | 21 | 3 | 7 | | | | |
| | Yes | 3 (100%) | | | 8 (67%) | 20 (95%) | 2 (67%) | 6 (86%) | | | | |
| | No | 0 | | | 4 (33%) | 1 (5%) | 1 (33%) | 1 (14%) | | | | |
| 0.7 mm | n | 11 | | | 9 | 9 | 4 | 12 | | | | |
| | Yes | 10 (91%) | | | 7 (78%) | 9 (100%) | 4 (100%) | 10 (83%) | | | | |
| | No | 1 (9%) | | | 2 (22%) | 0 | 0 | 2 (17%) | | | | |
| ~0.8 mm | n | 10 | | | 37 | 35 | 9 | 8 | | | | |
| | Yes | 9 (90%) | | | 30 (81%) | 32 (91%) | 9 (100%) | 5 (63%) | | | | |
| | No | 1 (10%) | | | 7 (19%) | 2 (9%) | 0 | 5 (38%) | | | | |
| Total | n | 24 | | | 63 | 67 | 18 | 29 | | | | |
| | Yes | 22 (92%) | | | 49 (78%) | 62 (93%) | 17 (94%) | 23 (79%) | | | | |
| | No | 2 (8%) | | | 14 (22%) | 5 (7%) | 1 (6%) | 6 (21%) | | | | |

Table 6

FIG. 8F

| Punctum Size Week 8 | | Example 1 Implant 300 (L68) 40D | Example 2 Implant 400 (L65) 40D | Example 3 Implant 500 (L67) 40D | Example 4 Implant 600 (L60) 40D | Example 5 Implant 600 (L63) 70D | Example 6 Implant 700 (L66) 70D | Example 7 Implant 800 (L61) 40D | Example 8 Implant 900 (L64) 70D | Example 9 Implant 1000 (L69) 70D | Example 10 Implant 1100 (L75) 70D | Example 11 Implant 1200 (L72) 70D |
|---|---|---|---|---|---|---|---|---|---|---|---|---|
| | | (N=32) | | | (N=72) | (N=85) | (N=28) | (N=33) | | | | |
| ~0.5 mm | n | 0 | 0 | | 5 | 2 | 2 | 2 | | | | |
| | Yes | 0 | 0 | | 4 (80%) | 1 (50%) | 2 (100%) | 2 (100%) | | | | |
| | No | 0 | 0 | | 1 (20%) | 1 (50%) | 0 | 0 | | | | |
| 0.6 mm | n | | 3 | | 12 | 21 | 3 | 7 | | | | |
| | Yes | | 3 (100%) | | 8 (67%) | 20 (95%) | 2 (67%) | 6 (86%) | | | | |
| | No | | 0 | | 4 (33%) | 1 (5%) | 1 (33%) | 1 (14%) | | | | |
| 0.7 mm | n | | 11 | | 9 | 9 | 4 | 12 | | | | |
| | Yes | | 10 (91%) | | 7 (78%) | 9 (100%) | 4 (100%) | 10 (83%) | | | | |
| | No | | 1 (9%) | | 2 (22%) | 0 | 0 | 2 (17%) | | | | |
| ~0.8 mm | n | | 10 | | 37 | 35 | 9 | 8 | | | | |
| | Yes | | 9 (90%) | | 30 (81%) | 32 (91%) | 9 (100%) | 5 (63%) | | | | |
| | No | | 1 (10%) | | 7 (19%) | 2 (9%) | 0 | 5 (38%) | | | | |
| Total | n | | 24 | | 63 | 67 | 18 | 29 | | | | |
| | Yes | | 22 (92%) | | 49 (78%) | 62 (93%) | 17 (94%) | 23 (79%) | | | | |
| | No | | 2 (8%) | | 14 (22%) | 5 (7%) | 1 (6%) | 6 (21%) | | | | |

Table 7

FIG. 8G

SECTION A-A

DETAIL B

| | L-PPDS Combined (N=95) |
|---|---|
| Age (years, mean ± SD) | 65.9 ± 9.8 |
| Male (%) | 45% |
| Race (%) | |
| Caucasian | 65% |
| Black | 25% |
| Asian | 3% |
| Hispanic | 5% |
| Other | 1% |
| Punctum size (mm, mean ± SD) | |
| OD, lower | 0.71 ± 0.14 |
| OS, lower | 0.71 ± 0.15 |
| OD, upper | 0.66 ± 0.12 |
| OS, upper | 0.65 ± 0.12 |
| Central Corneal Thickness (μm, mean ± SD) | |
| OD | 552.5 ± 28.7 |
| OS | 556.3 ± 29.3 |
| IOP (mmHg; mean ± SD) | 25.75 ± 1.62 |

FIG. 11

Summary of Retention Rate by Visit and Punctum Size FOR Group 1

| Visit | Punctum Size | | L67-L (N=94) | | L67-U (N=40) | | L69-L (N=152) | | L69-U (N=153) | | Other (N=5) | | Total (N=444) | |
|---|---|---|---|---|---|---|---|---|---|---|---|---|---|---|
| Day 0 | < 0.6 mm | n | 12 | | 7 | | 42 | | 51 | | 1 | | 113 | |
| | | Yes | 12 | (100%) | 7 | (100%) | 42 | (100%) | 51 | (100%) | 1 | (100%) | 113 | (100%) |
| | | No | 0 | | 0 | | 0 | | 0 | | 0 | | 0 | |
| | 0.6-0.8 mm | n | 53 | | 24 | | 92 | | 100 | | 4 | | 273 | |
| | | Yes | 53 | (100%) | 24 | (100%) | 92 | (100%) | 100 | (100%) | 4 | (100%) | 273 | (100%) |
| | | No | 0 | | 0 | | 0 | | 0 | | 0 | | 0 | |
| | > 0.8 mm | n | 29 | | 9 | | 18 | | 2 | | 0 | | 58 | |
| | | Yes | 29 | (100%) | 9 | (100%) | 18 | (100%) | 2 | (100%) | 0 | | 58 | (100%) |
| | | No | 0 | | 0 | | 0 | | 0 | | 0 | | 0 | |
| | Total | n | 94 | | 40 | | 152 | | 153 | | 5 | | 444 | |
| | | Yes | 94 | (100%) | 40 | (100%) | 152 | (100%) | 153 | (100%) | 5 | (100%) | 444 | (100%) |
| | | No | 0 | | 0 | | 0 | | 0 | | 0 | | 0 | |
| Week 4 | < 0.6 mm | n | 12 | | 7 | | 30 | | 39 | | 1 | | 89 | |
| | | Yes | 11 | (92%) | 6 | (86%) | 25 | (83%) | 26 | (67%) | 1 | (100%) | 69 | (78%) |
| | | No | 1 | (8%) | 1 | (14%) | 5 | (17%) | 13 | (33%) | 0 | | 20 | (22%) |
| | 0.6-0.8 mm | n | 47 | | 24 | | 63 | | 68 | | 4 | | 206 | |
| | | Yes | 47 | (100%) | 21 | (88%) | 57 | (90%) | 44 | (65%) | 4 | (100%) | 173 | (84%) |
| | | No | 0 | | 3 | (13%) | 6 | (10%) | 24 | (35%) | 0 | | 33 | (16%) |
| | > 0.8 mm | n | 26 | | 9 | | 12 | | 2 | | 0 | | 49 | |
| | | Yes | 25 | (96%) | 6 | (67%) | 12 | (100%) | 2 | (100%) | 0 | | 45 | (92%) |
| | | No | 1 | (4%) | 3 | (33%) | 0 | | 0 | | 0 | | 4 | (8%) |
| | Total | n | 85 | | 40 | | 105 | | 109 | | 5 | | 344 | |
| | | Yes | 83 | (98%) | 33 | (83%) | 94 | (90%) | 72 | (66%) | 5 | (100%) | 287 | (83%) |
| | | No | 2 | (2%) | 7 | (18%) | 11 | (10%) | 37 | (34%) | 0 | | 57 | (17%) |

FIG. 12A

Summary of Retention Rate by Visit and Punctum Size FOR Group 1

| Visit | Punctum Size | | L67-L (N=94) | | L67-U (N=40) | | L69-L (N=152) | | L69-U (N=153) | | Other (N=5) | | Total (N=444) | |
|---|---|---|---|---|---|---|---|---|---|---|---|---|---|---|
| Week 8 | < 0.6 mm | n | 12 | | 7 | | 28 | | 37 | | 1 | | 85 | |
| | | Yes | 11 | (92%) | 5 | (71%) | 20 | (71%) | 20 | (54%) | 1 | (100%) | 57 | (67%) |
| | | No | 1 | (8%) | 2 | (29%) | 8 | (29%) | 17 | (46%) | 0 | | 28 | (33%) |
| | 0.6-0.8 mm | n | 42 | | 21 | | 58 | | 65 | | 2 | | 188 | |
| | | Yes | 39 | (93%) | 17 | (81%) | 50 | (86%) | 34 | (52%) | 2 | (100%) | 142 | (76%) |
| | | No | 3 | (7%) | 4 | (19%) | 8 | (14%) | 31 | (48%) | 0 | | 46 | (24%) |
| | > 0.8 mm | n | 21 | | 8 | | 11 | | 2 | | 0 | | 42 | |
| | | Yes | 20 | (95%) | 4 | (50%) | 10 | (91%) | 2 | (100%) | 0 | | 36 | (86%) |
| | | No | 1 | (5%) | 4 | (50%) | 1 | (9%) | 0 | | 0 | | 6 | (14%) |
| | Total | n | 75 | | 36 | | 97 | | 104 | | 3 | | 315 | |
| | | Yes | 70 | (93%) | 26 | (72%) | 80 | (82%) | 56 | (54%) | 3 | (100%) | 235 | (75%) |
| | | No | 5 | (7%) | 10 | (28%) | 17 | (18%) | 48 | (46%) | 0 | | 80 | (25%) |
| Week 12 | < 0.6 mm | n | 12 | | 7 | | 28 | | 35 | | 0 | | 82 | |
| | | Yes | 11 | (92%) | 5 | (71%) | 18 | (64%) | 16 | (46%) | 0 | | 50 | (61%) |
| | | No | 1 | (8%) | 2 | (29%) | 10 | (36%) | 19 | (54%) | 0 | | 32 | (39%) |
| | 0.6-0.8 mm | n | 30 | | 11 | | 47 | | 50 | | 2 | | 140 | |
| | | Yes | 27 | (90%) | 9 | (82%) | 34 | (72%) | 19 | (38%) | 2 | (100%) | 91 | (65%) |
| | | No | 3 | (10%) | 2 | (18%) | 13 | (28%) | 31 | (62%) | 0 | | 49 | (35%) |
| | > 0.8 mm | n | 9 | | 2 | | 11 | | 1 | | 0 | | 23 | |
| | | Yes | 8 | (89%) | 1 | (50%) | 10 | (91%) | 0 | | 0 | | 19 | (83%) |
| | | No | 1 | (11%) | 1 | (50%) | 1 | (9%) | 1 | (100%) | 0 | | 4 | (17%) |
| | Total | n | 51 | | 20 | | 86 | | 86 | | 2 | | 245 | |
| | | Yes | 46 | (90%) | 15 | (75%) | 62 | (72%) | 35 | (41%) | 2 | (100%) | 160 | (65%) |
| | | No | 5 | (10%) | 5 | (25%) | 24 | (28%) | 51 | (59%) | 0 | | 85 | (35%) |

FIG. 12B

SUSTAINED RELEASE DELIVERY OF ACTIVE AGENTS TO TREAT GLAUCOMA AND OCULAR HYPERTENSION

CROSS-REFERENCE TO RELATED APPLICATIONS

This application is a Continuation application of U.S. Ser. No. 14/136,024; filed on 20 Dec. 2013, which is a Continuation application of U.S. application Ser. No. 13/598,573, filed on Aug. 29, 2012, and claims priority to U.S. Provisional Patent Application No. 61/528,736, filed on Aug. 29, 2011, and U.S. Provisional Patent Application No. 61/644,397, filed on May 8, 2012, the disclosures of each of which are incorporated herein by reference in their entirety for all purposes.

FIELD OF THE INVENTION

This application pertains generally to methods of treating ocular diseases, particularly glaucoma.

BACKGROUND OF THE INVENTION

Glaucoma is a collection of disorders characterized by progressive visual field loss due to optic nerve damage. It is the leading cause of blindness in the United States, affecting 1-2% of individuals aged 60 and over. Although there are many risk factors associated with the development of glaucoma (age, race, myopia, family history, and injury), elevated intraocular pressure, also known as ocular hypertension, is the only risk factor successfully manipulated and correlated with the reduction of glaucomatous optic neuropathy. Public health figures estimate that 2.5 million Americans manifest ocular hypertension.

In glaucoma associated with an elevation in eye pressure the source of resistance to outflow is in the trabecular meshwork. The tissue of the trabecular meshwork allows the "aqueous" to enter Schlemm's canal, which then empties into aqueous collector channels in the posterior wall of Schlemm's canal and then into aqueous veins. The aqueous or aqueous humor is a transparent liquid that fills the region between the cornea at the front of the eye and the lens. The aqueous humor is constantly secreted by the ciliary body around the lens, so there is a continuous flow of the aqueous humor from the ciliary body to the eye's front chamber. The eye's pressure is determined by a balance between the production of aqueous and its exit through the trabecular meshwork (major route) or via uveal scleral outflow (minor route). The trabecular meshwork is located between the outer rim of the iris and the internal periphery of the cornea. The portion of the trabecular meshwork adjacent to Schlemm's canal causes most of the resistance to aqueous outflow (juxtacanilicular meshwork).

Glaucoma is grossly classified into two categories: closed-angle glaucoma and open-angle glaucoma. The closed-angle (glaucoma is caused by closure of the anterior angle by contact between the iris and the inner surface of the trabecular meshwork. Closure of this anatomical angle prevents normal drainage of aqueous humor from the anterior chamber of the eye. Open-angle glaucoma is any glaucoma in which the angle of the anterior chamber remains open, but the exit of aqueous through the trabecular meshwork is diminished. The exact cause for diminished filtration is unknown for most cases of open-angle glaucoma. However, there are secondary open-angle glaucomas that may include edema or swelling of the trabecular spaces (from steroid use), abnormal pigment dispersion, or diseases such as hyperthyroidism that produce vascular congestion.

All current therapies for glaucoma are directed at decreasing intraocular pressure. This is initially by medical therapy with drops or pills that reduce the production of aqueous humor or increase the outflow of aqueous. Surgical therapy for open-angle glaucoma consists of laser (trabeculoplasty), trabeculectomy and aqueous shunting implants after failure of trabeculectomy or if trabeculectomy is unlikely to succeed. Trabeculectomy is a major surgery that is most widely used and is augmented with topically applied anticancer drugs such as 5-flurouracil or mitomycin-c to decrease scarring and increase surgical success.

Other means to treat glaucoma and ocular hypertension, involve the administration of drugs to the eye. A conventional method of drug delivery is by topical drop application to the eye's surface. Topical eye drops, though effective, can be inefficient. For instance, when an eye drop is instilled in an eye, it often overfills the conjunctival sac (i.e., the pocket between the eye and the lids) causing a substantial portion of the drop to be lost due to overflow of the lid margin and spillage onto the cheek. In addition, a large portion of the drop remaining on the ocular surface can be washed away into and through a lacrimal canaliculus, thereby diluting the concentration of the drug before it can treat the eye. Further, in many cases, topically applied medications have a peak ocular effect within about two hours, after which additional applications of the medications should be performed to maintain the therapeutic benefit. PCT Publication WO 06/014434 (Lazar), which is incorporated herein by reference in its entirety, may be relevant to these or other issues associated with eye drops.

Compounding ocular management difficulty, patients often do not use their eye drops as prescribed. Noncompliance rates of at least 25% are reported. This poor compliance can be due to discomfort and the normal reflex to protect the eye. Therefore, one or more drops may miss the eye. Older patients may have additional problems instilling drops due to arthritis, unsteadiness, and decreased vision. Pediatric and psychiatric populations pose difficulties as well.

Lacrimal implants are devices that are inserted into a punctum and an associated lacrimal canaliculus of an eye, either to block drainage of tears (to prevent conditions such as dry eye), or to contain a quantity of drug for release into the eye.

FIGS. 1-2 illustrate example views of anatomical tissue structures associated with an eye 100. Certain of the anatomical tissue structures shown may be suitable for treatment using the various lacrimal implants and methods discussed herein. The eye 100 is a spherical structure including a wall having three layers: an outer sclera 102, a middle choroid layer 104 and an inner retina 106. The sclera 102 includes a tough fibrous coating that protects the inner layers. It is mostly white except for the transparent area at the front, commonly known as the cornea 108, which allows light to enter the eye 100.

The choroid layer 104, situated inside the sclera 102, contains many blood vessels and is modified at the front of the eye 100 as a pigmented iris 110. A biconvex lens 112 is situated just behind the pupil. A chamber 114 behind the lens 112 is filled with vitreous humor, a gelatinous substance. Anterior and posterior chambers 116 are situated between the cornea 108 and iris 110, respectively and filled with aqueous humor. At the back of the eye 100 is the light-detecting retina 106.

The cornea 108 is an optically transparent tissue that conveys images to the back of the eye 100. It includes a vascular tissue to which nutrients and oxygen are supplied via bathing with lacrimal fluid and aqueous humor as well as from blood vessels that line the junction between the cornea 108 and sclera 102. The cornea 108 includes a pathway for the permeation of drugs into the eye 100.

Turing to FIG. 2, other anatomical tissue structures associated with the eye 100 including the lacrimal drainage system, which includes a secretory system 230, a distributive system and an excretory system, are shown. The secretory system 230 comprises secretors that are stimulated by blinking and temperature change due to tear evaporation and reflex secretors that have an efferent parasympathetic nerve supply and secrete tears in response to physical or emotional stimulation. The distributive system includes the eyelids 202 and the tear meniscus around the lid edges of an open eye, which spread tears over the ocular surface by blinking, thus reducing dry areas from developing.

The excretory system of the lacrimal drainage system includes, in order of flow, drainage, the lacrimal puncta, the lacrimal canaliculi, the lacrimal sac 204 and the lacrimal duct 206. From the lacrimal duct 206, tears and other flowable materials drain into a passage of the nasolacrimal system. The lacrimal canaliculi include an upper (superior) lacrimal canaliculus 208 and a lower (inferior) lacrimal canaliculus 210, which respectively terminate in an upper 212 and lower 214 lacrimal punctum. The upper 212 and lower 214 punctum are slightly elevated at the medial end of a lid margin at the junction 216 of the ciliary and lacrimal portions near a conjunctival sac 218. The upper 212 and lower 214 punctum are generally round or slightly ovoid openings surrounded by a connective ring of tissue. Each of puncta 212, 214 leads into a vertical portion 220, 222 of their respective canaliculus before turning more horizontal at a canaliculus curvature 250 to join one another at the entrance of the lacrimal sac 204. The canaliculi 208, 210 are generally tubular in shape and lined by stratified squamous epithelium surrounded by elastic tissue, which permits them to be dilated. As shown, a lacrimal canaliculus ampulla 252 exists near an outer edge of each canaliculus curvature 250.

For numerous reasons (e.g., the size, shape, positioning, and materials of some conventional lacrimal implants, and variability in punctum size and shape), retention of the implants in the punctum and associated lacrimal canaliculus has been inconsistent. Users of lacrimal implants may inadvertently dislodge the lacrimal implant by wiping their eye. Further, some configurations of lacrimal implants may dislodge themselves, such as when a user sneezes, or tears excessively.

Accordingly, it is desirable to have a lacrimal implant that solves these problems and provides improved retention across different sizes of puncta.

SUMMARY OF THE INVENTION

In an exemplary embodiment, the present invention provides methods of reducing intraocular pressure (IOP) in an eye. In an exemplary embodiment, the method of the invention utilizes two latanoprost-eluting punctal implants. Previous methods of delivering latanoprost to the eye using a latanoprost-eluting punctal implant have met with varied and minimal success. For example, as show in FIG. 16, in an eye implanted with a single latanoprost-eluting plug, the reduction in IOP is minimal, and is substantially identical across a range of latanoprost loadings: from 3.5 µg to 95 µg, the IOP does not decrease even though more latanoprost is being delivered by the plugs with higher latanoprost loading. See, FIG. 17. Thus, it is surprising that the methods of the present invention, in which an eye has a latanoprost-eluting punctal implant in both the upper and lower punctum yields a statistically significant reduction in IOP after about two weeks.

In an exemplary embodiment, the methods of the invention provide a reduction in IOP of at least about 5 mm Hg, at least about 6 mm Hg or at least about 7 mm Hg from baseline during the treatment period during which the two punctal plugs are implanted.

In various embodiments, the method of the invention includes implanting a first lacrimal implant through a first lacrimal punctum and into a first lacrimal canaliculus of the eye of the patient. The first lacrimal implant is configured to release an intraocular pressure-reducing therapeutic agent to the eye of the patient on a sustained basis. In an exemplary embodiment, the first implant contains approximately 46 µg of latanoprost and the second implant contains about 95 µg of latanoprost. In an exemplary embodiment, the first implant is installed in the upper punctum and the second implant is installed in the lower punctum. In various embodiments, the location of the implants is reversed.

The method of the invention can include implanting more than one implant in more than one punctum of one or more eye. Thus, in various embodiments, the method also includes implanting a second lacrimal implant through a second punctum and into a second lacrimal canaliculus of the eye of the patient, the second lacrimal implant being configured to release the intraocular pressure-reducing therapeutic agent to the eye of the patent on a sustained basis.

In various embodiments, the implant is configured to release, on a sustained basis over a selected timecourse to the eye, a total amount of the intraocular pressure-reducing therapeutic agent from a combination of the first lacrimal implant and the second lacrimal implant greater than or equal to a recommended daily total dose of the intraocular pressure-reducing therapeutic agent in eye drop form to reduce intraocular pressure of the eye by at least 5 mm Hg from baseline for a continuous period of time of at least 2 weeks after implantation of the first lacrimal implant and the second lacrimal implant.

In an exemplary embodiment, the invention provides a method for reducing intraocular pressure in an eye of a subject in need thereof. An exemplary method includes implanting a first lacrimal implant through a first punctum and into a first lacrimal canaliculus of an eye of the subject. The first lacrimal implant is configured to release a therapeutically effective amount of an intraocular pressure-reducing therapeutic agent to the eye of the patient on a sustained basis. In various embodiments a second implant is installed in a second punctum or in a second eye. Thus, there is provided a method as set forth above, further comprising implanting a second lacrimal implant through a second punctum and into a second lacrimal canaliculus of the eye of the subject. The second lacrimal implant is configured to release the intraocular pressure-reducing therapeutic agent to the eye of the patent on a sustained basis. The method also includes, once the one or more implant is installed in an eye, releasing, on a sustained basis over a selected time course to the eye, a total amount of the intraocular pressure-reducing therapeutic agent from a combination of the first lacrimal implant and the second lacrimal implant. The total amount of therapeutic agent released is sufficient to reduce the intraocular pressure.

The implant can be of any useful form, structure or composition. In an exemplary embodiment, the implant includes, a first member defining a first axis and having a first end along the first axis. The implant also includes a second member defining a second axis and having a second end along the second axis; and a third member connecting the first end of the first member and the second end of the second member at a first angle to form an angled intersection, and the third member comprising a bore that is characterized by a third axis and a second angle. In general, the first angle is defined by the first axis with respect to the second axis, the second angle is defined by the first axis with respective to the third axis, and the bore is configured to be accessible to an insertion tool for facilitating insertion of the implant.

Also provided are kits that include at least one implant. An exemplary kit includes one or more implant operatively engaged to an implanting tool of use in implanting the device in the puntum of a subject's eye.

The devices and methods described herein include a removable, and optionally drug releasing, lacrimal implant, which can be implanted in the lacrimal caniliculus through a lacrimal punctum. In various embodiments, the lacrimal implants described herein utilize the features of the nasolacrimal drainage system (e.g., by mimicking the shape of the lacrimal canaliculus) to provide improved patient comfort and implant retention in the ocular anatomy. In this way, exemplary lacrimal implants described herein overcome drawbacks associated with current implants. The lacrimal implants described herein are easily implanted and removed without much biasing of the lacrimal punctum or associated canaliculus, and are securely retained in the lacrimal canaliculus upon implantation, optionally without being pre-sized to a particular lacrimal punctum or canaliculus diameter. In various embodiments, the implants are drug delivery system, providing sustained, localized release of one or more drugs or other therapeutic agents at a desired therapeutic level for an extended period of time.

In an exemplary embodiment, the invention provides an implant for insertion into a lacrimal canaliculus. An exemplary implant includes, a first member defining a first axis and having a first end along the first axis. The implant also includes a second member defining a second axis and having a second end along the second axis. The implant further includes a third member connecting the first end of the first member and the second end of the second member at a first angle to form an angled intersection. The third member includes a bore that is characterized by a third axis and a second angle. The bore is configured to be accessible to an insertion tool for facilitating insertion of the implant. In various embodiments, the first angle is defined by the first axis with respect to the second axis and the second angle is defined by the first axis with respective to the third axis.

In various embodiments, the invention includes a kit having an implant of the invention and an insertion tool for inserting the implant into the punctum.

Also provided is a method of treating an ocular disease using one or more punctal implant.

These and other embodiments, advantages, and aspects of the methods disclosed herein are set forth in part in following detailed description.

BRIEF DESCRIPTION OF THE DRAWINGS

In the drawings, like numerals describe similar components throughout the several views. Like numerals having different letter suffixes represent different instances of similar components. The drawings illustrate generally, by way of example, but not by way of limitation, various embodiments disclosed herein.

FIG. 4B is a cross-sectional view depicting an implant having a cavity formed in the second member, in accordance with an embodiment of the present invention.

FIG. 4C is a partially enlarged view taken about circle IV(C) of FIG. 4B depicting a cavity in the second member and a bore in the third member of an implant, in accordance with an embodiment of the present invention.

FIG. 8A provides initial retention data for various exemplary implants in accordance with various embodiments of the present invention.

FIG. 8B lists retention data for various exemplary implants over one day, in accordance with various embodiments of the present invention.

FIG. 8C lists retention data for various exemplary implants over one week, in accordance with various embodiments of the present invention.

FIG. 8D lists retention data for various exemplary implants over two weeks, in accordance with various embodiments of the present invention.

FIG. 8E lists retention data for various exemplary implants over four weeks, in accordance with various embodiments of the present invention.

FIG. 8F lists retention data for various exemplary implants over eight weeks, in accordance with various embodiments of the present invention.

FIG. 8G lists retention data for various exemplary implants over twelve weeks, in accordance with various embodiments of the present invention.

FIG. 11 provides the baseline demographics for the comparison studies herein.

FIG. 12A and FIG. 12B lists retention data for various exemplary implants over four weeks, in accordance with various embodiments of the present invention.

DETAILED DESCRIPTION OF THE INVENTION

In an exemplary embodiment of the present invention, there is provided a method for reducing intraocular pressure in an eye of a patient in need thereof. The method includes releasing from a device implanted in the eye an intraocular pressure reducing therapeutic agent in a sustained release manner. The methods of the invention are applicable to both human and veterinary uses.

Figure 16:
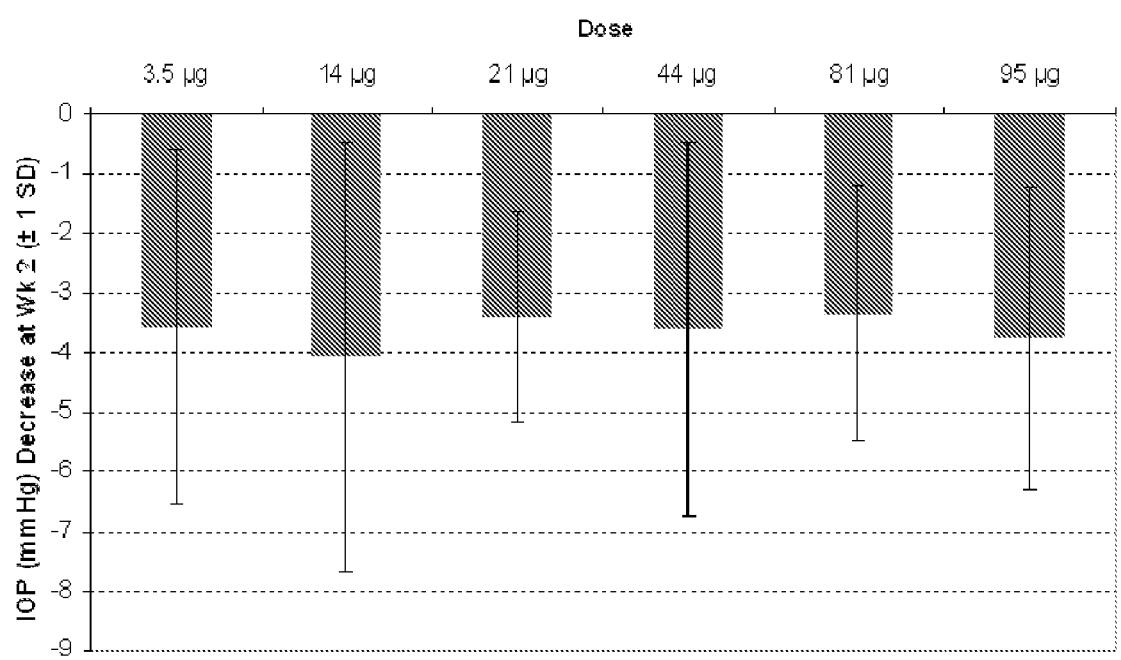
FIG. 16 illustrates the lack of dose dependency of intraocular pressure reduction when latanoprost is administered from a single punctal implant.
Figure 17:
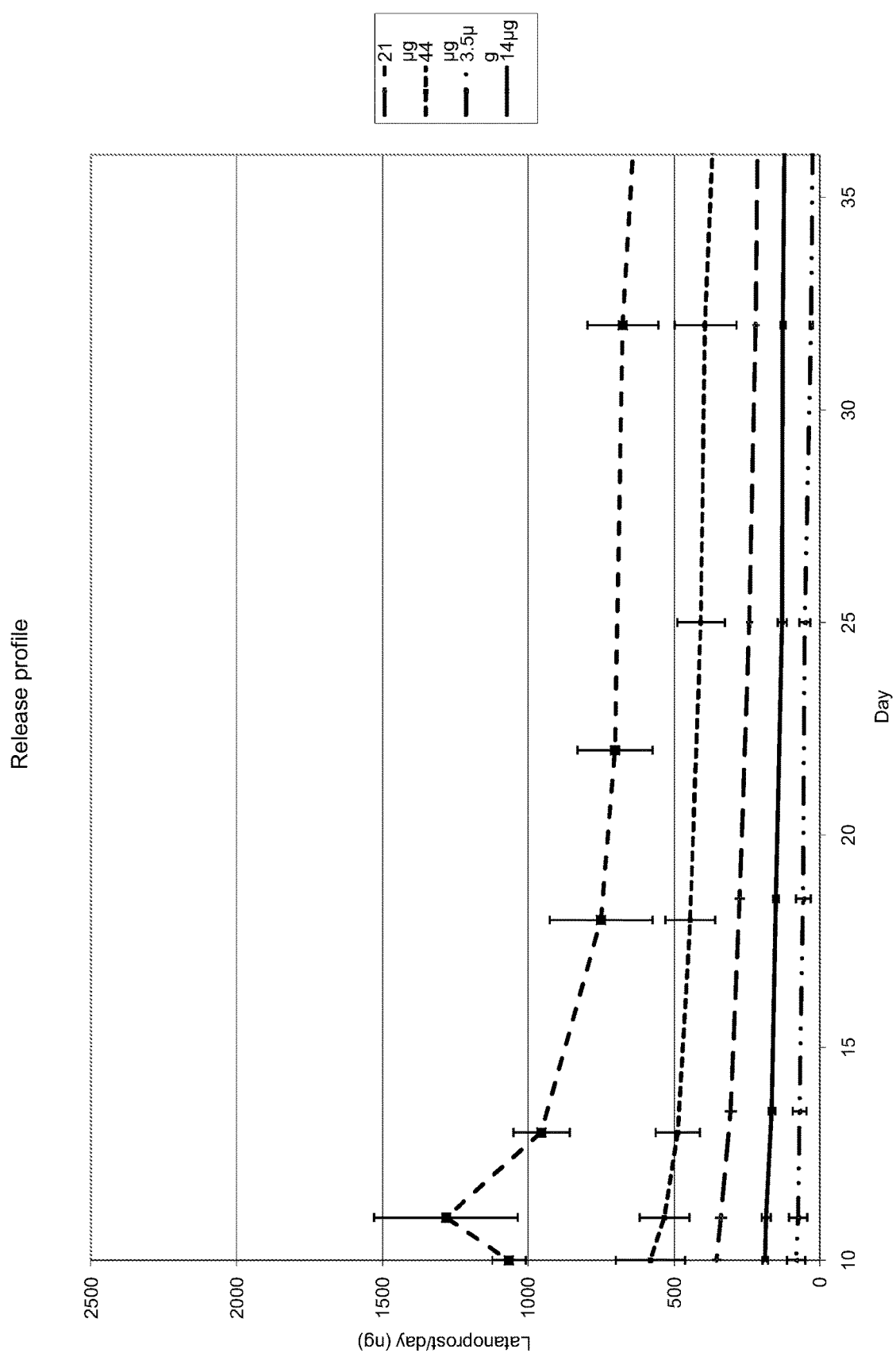
FIG. 17 illustrates the dosages of latanoprost delivered by the punctal implants of FIG. 16.

In an exemplary embodiment, the present invention provides methods of reducing intraocular pressure (IOP) in an eye. In an exemplary embodiment, the method of the invention utilizes two latanoprost-eluting punctal implants. Previous methods of delivering latanoprost to the eye using a latanoprost-eluting punctal implant have met with varied and minimal success. For example, as show in FIG. 16, in an eye implanted with a single latanoprost-eluting plug, the reduction in IOP is minimal, and is substantially identical across a range of latanoprost loadings: from 3.5 µg to 95 µg, the IOP does not decrease even though more latanoprost is being delivered by the plugs with higher latanoprost loading. See, FIG. 17. Thus, it is surprising that the methods of the present invention, in which an eye has a latanoprost-eluting punctal implant in both the upper and lower punctum yields a statistically significant reduction in IOP after about two weeks.

In an exemplary embodiment, the methods of the invention provide a reduction in IOP of at least about 5 mm Hg, at least about 6 mm Hg or at least about 7 mm Hg from baseline during the treatment period during which the two punctal plugs are implanted.

Also disclosed herein are exemplary structures of ocular implants of use in the methods of the invention for treating various diseases and disorders. Exemplary structures include lacrimal implants for at least partial insertion through the lacrimal punctum and into its associated canaliculus. Various embodiments further provide an insertion tool for placing a lacrimal implant into a lacrimal punctum. Also disclosed herein are exemplary implants including therapeutic agents incorporated throughout the device, within one or more section of the device, or in a therapeutic agent core, e.g., a localized therapeutic agent core. The devices of the invention are of use for treating various diseases.

In the various embodiments of methods of the invention, implanting a lacrimal implant of the invention through the lacrimal punctum and into its associated canaliculus, in various embodiments, inhibits or blocks tear flow therethrough. In various embodiments, a device inhibiting or blocking tear flow is of use to treat dry eye. In an exemplary embodiment, the insertion of the lacrimal implant allows for the delivery of a therapeutic agent. In various embodiments, the delivery is sustained delivery. Exemplary therapeutic agents incorporated into the implants of the invention are of use to treat the eye, or they can be of use more broadly systemic therapies. For example, using a device of the invention, the therapeutic agent can be delivered to a nasal passage, to an inner ear system, or to other passages or systems for treatment of various diseases including, but not limited to, eye infection, eye inflammation, glaucoma, other ocular disease, other ocular disorder, a sinus or allergy disorder, dizziness or a migraine. The devices of the invention are of use for systemic delivery of one or more therapeutic agents in an amount having therapeutic efficacy.

Those of ordinary skill in the art will understand that the following detailed description of the present invention is illustrative only and is not intended to be in any way limiting. Other embodiments of the present invention will readily suggest themselves to such skilled persons having benefit of this disclosure. Reference will now be made in detail to implementations of the present invention as illustrated in the accompanying drawings. The same reference indicators will be used throughout the drawings and the following detailed description to refer to the same or like parts.

Definitions

As used herein, the terms "a" or "an" are used, as is common in patent documents, to include one or more than one, independent of any other instances or usages of "at least one" or "one or more."

As used herein, the term "or" is used to refer to a nonexclusive or, such that "A or B" includes "A but not B," "B but not A," and "A and B," unless otherwise indicated.

As used herein, the term "about" is used to refer to an amount that is approximately, nearly, almost, or in the vicinity of being equal to or is equal to a stated amount, e.g., the state amount plus/minus about 5%, about 4%, about 3%, about 2% or about 1%.

As used herein, an "axis" refers to a general direction along which a member extends. According to this definition, the member is not required to be entirely or partially symmetric with respect to the axis or to be straight along the direction of the axis. Thus, in the context of this definition, any member disclosed in the present application characterized by an axis is not limited to a symmetric or a straight structure.

In this document, the term "proximal" refers to a location relatively closer to the cornea of an eye, and the term "distal" refers to a location relatively further from the cornea and inserted deeper into a lacrimal canaliculus.

In the appended claims, the terms "including" and "in which" are used as the plain-English equivalents of the respective terms "comprising" and "wherein." Also, in the following claims, the terms "including" and "comprising" are open-ended, that is, a system, assembly, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

As used herein, the term "adverse event" refers to any undesirable clinical event experienced by a patient undergoing a therapeutic treatment including a drug and/or a medical device, whether in a clinical trial or a clinical practice. Adverse events include a change in the patient's condition or laboratory results, which has or could have a deleterious effect on the patient's health or well-being. For example, adverse events include but are not limited to: device malfunction identified prior to placement, device malposition, device malfunction after placement, persistent inflammation, endophthalmitis, corneal complications (corneal edema, opacification, or graft decompensation), chronic pain, iris pigmentation changes, conjunctival hyperemia, eyelash growth (increased length, thickness, pigmentation, and number of lashes), eyelid skin darkening, intraocular inflammation (iritis/uveitis), macular edema including cystoid macular edema, blurred vision, burning and stinging, foreign body sensation, itching, punctate epithelial keratopathy, dry eye, excessive tearing, eye pain, lid crusting, lid discomfort/pain, lid edema, lid erythema, photophobia, VA decrease, conjunctivitis, diplopia, discharge from the eye, retinal artery embolus, retinal detachment, vitreous hemorrhage from diabetic retinopathy, upper respiratory tract infection/cold/flu, chest pain/angina pectoris, muscle/joint/back pain, and rash/allergic skin reaction, eye pruritus, increase in lacrimation, ocular hyperemia and punctate keratitis. In an exemplary embodiment, use of the device and method of the invention results in one or more of: (i) occurrence of fewer adverse events; or (ii) adverse events of less severity, than those occurring with the use of a therapeutic agent in drop form, e.g., when the therapeutic agent is administered via drops in essentially the same unit dosage as that delivered by a device as set forth herein.

As used herein, the phrase "consisting essentially of" limits a composition to the specified materials or steps and those additional, undefined components that do not materially affect the basic and novel characteristic(s) of the composition.

As used herein, the term "continuous" or "continuously" means essentially unbroken or uninterrupted. For example, continuously administered active agents are administered over a period of time essentially without interruption.

As used herein, the term "diameter" encompasses a broad meaning. For example, with respect to a member having a circular cross section, the term "diameter" has the conventional meaning and refers to a straight line through the center of the circle connecting two points on the circumference. When the cross section is not a circle, the term "diameter" in the present disclosure refers to the characteristic diameter of the cross section. The "characteristic diameter" refers to the diameter of a circle that has the same surface area as the cross section of the element. In the present application, "diameter" is interchangeable with "characteristic diameter."

As used herein, the term "eye" refers to any and all anatomical tissues and structures associated with an eye. The eye is a spherical structure with a wall having three layers: the outer sclera, the middle choroid layer and the inner retina. The sclera includes a tough fibrous coating that protects the inner layers. It is mostly white except for the transparent area at the front, the cornea, which allows light to enter the eye. The choroid layer, situated inside the sclera, contains many blood vessels and is modified at the front of the eye as the pigmented iris. The biconvex lens is situated just behind the pupil. The chamber behind the lens is filled with vitreous humour, a gelatinous substance. The anterior and posterior chambers are situated between the cornea and iris, respectively and filled with aqueous humour. At the back of the eye is the light-detecting retina. The cornea is an optically transparent tissue that conveys images to the back of the eye. It includes avascular tissue to which nutrients and oxygen are supplied via bathing with lacrimal fluid and aqueous humour as well as from blood vessels that line the junction between the cornea and sclera. The cornea includes one pathway for the permeation of drugs into the eye. Other anatomical tissue structures associated with the eye include the lacrimal drainage system, which includes a secretory system, a distributive system and an excretory system. The secretory system comprises secretors that are stimulated by blinking and temperature change due to tear evaporation and reflex secretors that have an efferent parasympathetic nerve supply and secrete tears in response to physical or emotional stimulation. The distributive system includes the eyelids and the tear meniscus around the lid edges of an open eye, which spread tears over the ocular surface by blinking, thus reducing dry areas from developing.

As used herein, the term "implant" refers to a structure that can be configured to contain or be impregnated with a drug, for example via a drug core or a drug matrix, such as those as disclosed in this patent document and in WO 07/115,261, which is herein incorporated by reference in its entirety, and which is capable of releasing a quantity of active agent, such as latanoprost or other intraocular pressure-reducing therapeutic agent(s), into tear fluid for a sustained release period of time when the structure is implanted at a target location along the path of the tear fluid in the patient. The terms "implant," "plug," "punctal plug," and "punctal implant" are meant herein to refer to similar structures. Likewise, the terms "implant body" and "plug body" are meant herein to refer to similar structures. The implants described herein may be inserted into the punctum of a subject, or through the punctum into the canaliculus. The implant may be also the drug core or drug matrix itself, which is configured for insertion into the punctum without being housed in a carrier such as a punctal implant occluder, for example having a polymeric component and a latanoprost or other intraocular pressure-reducing therapeutic agent(s) component with no additional structure surrounding the polymeric component and latanoprost or other intraocular pressure-reducing therapeutic agent(s) component.

As used in exemplary embodiments herein, "loss of efficacy" (LoE) is defined as an IOP increase to baseline (post-washout) IOP in either or both eyes while wearing a latanoprost punctal plug delivery system (L-PPDS) continuously from Day 0. Subjects were followed for at least 4 weeks before the subject could complete the study due to LoE and LoE was confirmed at 2 sequential visits.

As used herein, a "pharmaceutically acceptable vehicle" is any physiologically acceptable vehicle known to those of ordinary skill in the art useful in formulating pharmaceutical compositions. Suitable vehicles include polymeric matrices, sterile distilled or purified water, isotonic solutions such as isotonic sodium chloride or boric acid solutions, phosphate buffered saline (PBS), propylene glycol and butylene glycol. Other suitable vehicular constituents include phenylmercuric nitrate, sodium sulfate, sodium sulfite, sodium phosphate and monosodium phosphate. Additional examples of other suitable vehicle ingredients include alcohols, fats and oils, polymers, surfactants, fatty acids, silicone oils, humectants, moisturizers, viscosity modifiers, emulsifiers and stabilizers. The compositions may also contain auxiliary substances, i.e. antimicrobial agents such as chlorobutanol, parabans or organic mercurial compounds; pH adjusting agents such as sodium hydroxide, hydrochloric acid or sulfuric acid; and viscosity increasing agents such as methylcellulose. An exemplary final composition is sterile, essentially free of foreign particles, and has a pH that allows for patient comfort and acceptability balanced with a pH that is desirable for optimum drug stability. An exemplary "pharmaceutically acceptable vehicle is an "ophthalmically acceptable vehicle" as used herein refers to any substance or combination of substances which are non-reactive with the compounds and suitable for administration to patient. In an exemplary embodiment, the vehicle is an aqueous vehicle suitable for topical application to the patient's eyes. In various embodiments, the vehicle further includes other ingredients which may be desirable to use in the ophthalmic compositions of the present invention include antimicrobials, preservatives, co-solvents, surfactants and viscosity building agents.

In various embodiments, the "pharmaceutically acceptable vehicle" includes more than one therapeutic agent.

As used herein, the term "punctum" refers to the orifice at the terminus of the lacrimal canaliculus, seen on the margins of the eyelids at the lateral extremity of the *lacus lacrimalis*. Puncta (plural of punctum) function to reabsorb tears produced by the lacrimal glands. The excretory part of the lacrimal drainage system includes, in flow order of drainage, the lacrimal puncta, the lacrimal canaliculi, the lacrimal sac and the lacrimal duct. From the lacrimal duct, tears and other flowable materials drain into a passage of the nasal system. The lacrimal canaliculi include an upper (superior) lacrimal canaliculus and a lower (inferior) lacrimal canaliculus, which respectively terminate in an upper and lower lacrimal punctum. The upper and lower punctum are slightly elevated at the medial end of a lid margin at the junction of the ciliary and lacrimal portions near a conjunctival sac. The upper and lower punctum are generally round or slightly ovoid openings surrounded by a connective ring of tissue. Each of the puncta leads into a vertical portion of their respective canaliculus before turning more horizontal at a canaliculus curvature to join one another at the entrance of the lacrimal sac. The canaliculi are generally tubular in shape and lined by stratified squamous epithelium surrounded by elastic tissue, which permits them to be dilated.

The terms "subject" and "patient" refer to animals such as mammals, including, but not limited to, primates (e.g., humans), cows, sheep, goats, horses, dogs, cats, rabbits, rats, mice and the like. In many embodiments, the subject or patient is a human.

An "intraocular pressure-reducing therapeutic agent" can comprise a drug and may be any of the following or their equivalents, derivatives or analogs, including anti-glaucoma medications (e.g. adrenergic agonists, adrenergic antagonists (beta blockers), carbonic anhydrase inhibitors (CAIs, systemic and topical), therapeutic agent(s) such as prostaglandins, antiprostaglandins, prostaglandin precursors, including antiglaucoma drugs including beta-blockers such as timolol, betaxolol, levobunolol, atenolol (see U.S. Pat. No. 4,952,581); adrenergic agonists including clonidine derivatives, such as apraclonidine or brimonidine (see U.S. Pat. No. 5,811,443); and prostaglandin analogues such as bimatoprost, travoprost, tafluprost, latanoprost, etc. In an exemplary embodiment, the therapeutic agent is already marketed for glaucoma, and commercially available preparations thereof can be used. Further therapeutic agents include carbonic anhydrase inhibitors such as acetazolamide, dorzolamide, brinzolamide, methazolamide, dichlorphenamide, diamox; and the like.

The term "topical" refers to any surface of a body tissue or organ. A topical formulation is one that is applied to a body surface, such as an eye, to treat that surface or organ. Topical formulations as used herein also include formulations that can release therapeutic agents into the tears to result in topical administration to the eye.

As used herein, the term "treating" or "treatment" of a state, disease, disorder, injury or condition as used herein is understood to mean one or more of (1) preventing or delaying the appearance of clinical symptoms of the state, disease, disorder, injury or condition developing in a mammal that may be afflicted with or predisposed to the state, disease, disorder, injury or condition but does not yet experience or display clinical or subclinical symptoms of the state, disease, disorder, injury or condition, (2) inhibiting the state, disease, disorder, injury or condition, i.e., arresting or reducing the development of the disease or at least one clinical or subclinical symptom thereof, or (3) relieving the state, disease, disorder, injury or condition, i.e., causing regression of the state, disease, disorder, injury or condition or at least one of its clinical or subclinical symptoms. In an exemplary embodiment, the present invention provides a method of treating glaucoma or ocular hypertension including contacting an effective intraocular pressure reducing amount of a composition with the eye in order to reduce eye pressure and to maintain the pressure on a reduced level for a sustained period, e.g., at least about 1, 2, 3, 4, 5, 6, 7 8, 9, 10, 11 or 12 weeks.

The term "delivering", as used herein, shall be understood to mean providing a therapeutically effective amount of a pharmaceutically active agent to a particular location within a host causing a therapeutically effective concentration of the pharmaceutically active agent at the particular location.

As used herein, the term "diameter" encompasses a broad meaning. For example, with respect to a member having a circular cross section, the term "diameter" has the conventional meaning and refers to a straight line through the center of the circle connecting two points on the circumference. When the cross section is not a circle, the term "diameter" in the present disclosure refers to the characteristic diameter of the cross section. The "characteristic diameter" refers to the diameter of a circle that has the same surface area as the cross section of the element. In the present application, "diameter" is interchangeable with "characteristic diameter."

Some embodiments of the invention provide the use of latanoprost or another active agent or agents for treatment of diabetic retinopathy, uveitis, intraocular inflammation, keratitis, dry eye, macular edema including cystoid macular edema, infection, macular degeneration, blurred vision, herpetic conjunctivitis, blepharitis, retinal or choroidal neovascularizaton, and other proliferative eye diseases. In some embodiments, the invention provides the use of an antiglaucoma drug for treatment of the above diseases. In certain embodiments, the use of a prostaglandin or prostaglandin analogue for treatment of the above diseases is provided.

"Prostaglandin derivatives", as used herein refers to compounds having the basic prostaglandin structure of 20 carbon atoms and a 5-carbon ring. Exemplary prostaglandin derivatives of use in the present invention are of the $PGI_2$, $PGE_2$ and $PGF_2\alpha$ types. The structure can be augmented by incorporating or eliminating functional groups (e.g., HO, carbonyl, ether, ester, carboxylic acid, halide) or by adding carbon atom-based radicals (e.g., Me, Et, i-Pr, etc.). See for example, U.S. Pat. No. 7,910,767. In some embodiments, the prostaglandin derivative is a derivative of PGA, PGB, PGD, PGE and PGF, in which the omega chain has been modified with the common feature of containing a ring structure. See, U.S. Pat. No. 5,296,504. The prostaglandin derivatives of use in the invention are synthesized de novo or derived from modification of naturally occurring prostaglandins.

Lacrimal Implants

FIGS. 3-6 illustrate exemplary embodiments of lacrimal implants of use in the methods of the invention. The exemplary implants are insertable through a lacrimal punctum 212, 214 and into its associated canaliculus 208, 210. Exemplary lacrimal implants of use in the present invention comprise a first member, a second member and a heel, such as the first member 305, the second member 310 and the third member or heel 330 depicted in FIG. 3A. Exemplary lacrimal implants further comprise a bore that is formed in the heel, for example, the bore 385 formed in the third member or heel 330 in FIG. 3A. In some embodiments, exemplary lacrimal implants further comprise a cavity 458 (e.g., lacrimal implants illustrated in FIG. 4A).

Figure 3B:
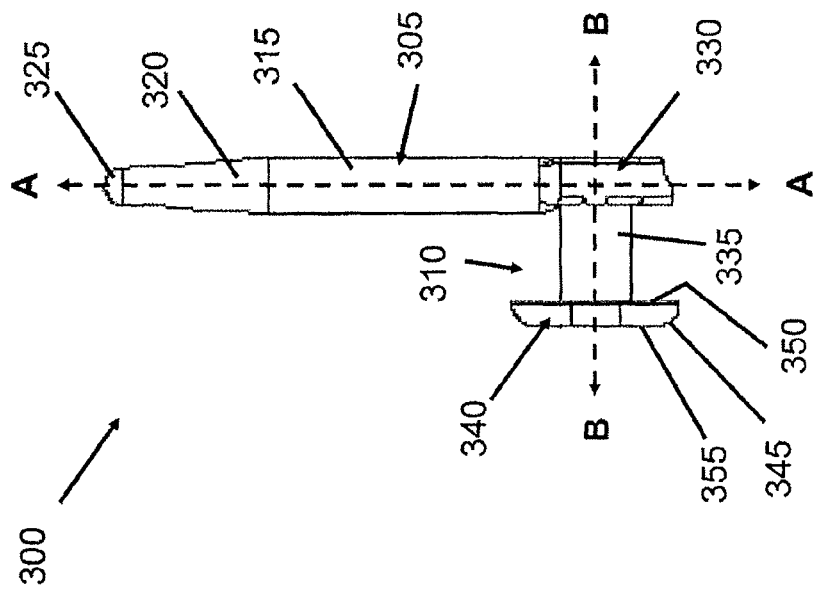
FIG. 3B is a side view of an implant in accordance with an embodiment of the present invention.
Figure 3A:
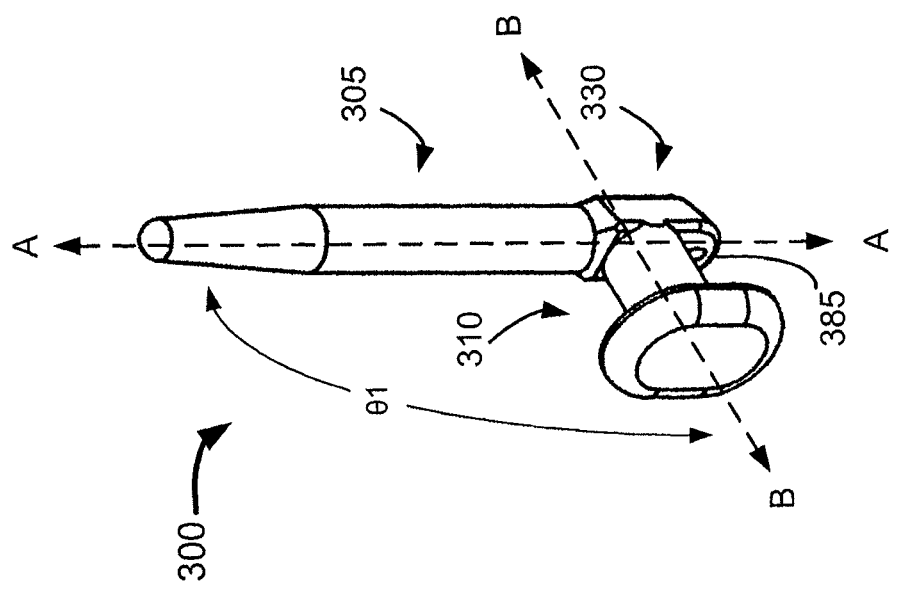
FIG. 3A provides a perspective view of an implant in accordance with an embodiment of the present invention.

Referring to FIG. 3A, where a perspective view of an exemplary lacrimal implant 300 of use in the present methods is depicted, the first member 305 is characterized by a first axis A and the second member 310 is characterized by a second axis B.

The third member or heel 330 is configured to connect the first member 305 and the second member 310 at a first angle $\theta_1$, where $\theta_1$ is defined by the first axis A with respect to the second axis B. For instance, in FIG. 3A, the first angle $\theta_1$ refers to the angle originating at the first axis A and turning counterclockwise from the first axis A to the second axis B. In some embodiments, the first axis A and the second axis B are in the same plane and intersect each other. In some embodiments, the first axis A is in a plane other than the plane of the second axis B, and the first axis A and the second axis B do not intersect. In such embodiments, the first angle $\theta_1$ refers to the angle defined by a parallel line of the first axis A with respect to the second axis B. This parallel line of the first axis A lies in the same plane as the second axis and intersects with the second axis.

In some embodiments, the first angle $\theta_1$ is from about 30 degrees to about 150 degrees, from about 45 degrees to about 135 degrees, or from about 75 degrees to about 105 degrees. For example, in some embodiments, the first angle $\theta_1$ is approximately 90 degrees.

In some embodiments, the overall dimension of the implant along the first axis is from about 4 mm to about 8 mm. In an exemplary embodiment, the overall dimension along the first axis is about 5 mm to about 7 mm. In various embodiments, the overall dimension along the first axis is about 6.3 mm.

In various embodiments, the overall dimension along the second axis B is from about 1 mm to about 3 mm, e.g., from about 1.2 mm to about 1.9 mm.

In some embodiments, the overall dimension along the first axis is approximately 6.3 mm and the overall dimension along the second axis is approximately 1.2 mm. In various embodiments, the overall dimension along the first axis is approximately 6.3 mm and the overall dimension along the second axis is approximately 1.9 mm. In some embodiments, the overall dimension along the first axis is approximately 4.8 mm and the overall dimension along the second axis is approximately 1.9 mm.

First Member 305

Figure 1:
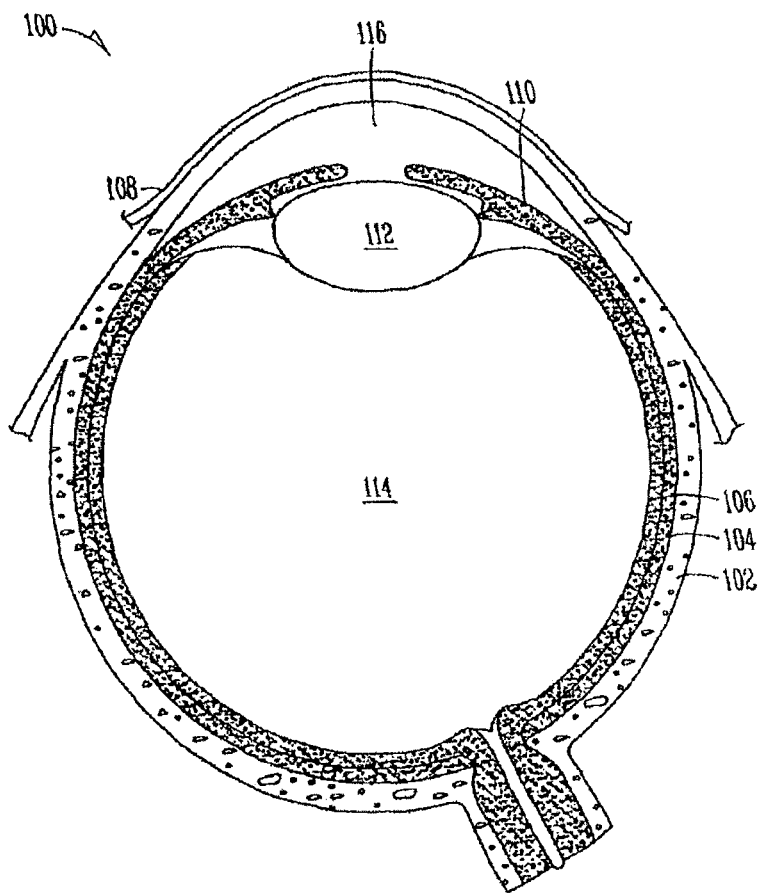
FIG. 1 illustrates an example of anatomical tissue structures associated with an eye, certain of these tissue structures providing a suitable environment in which a lacrimal implant can be used.
Figure 2:
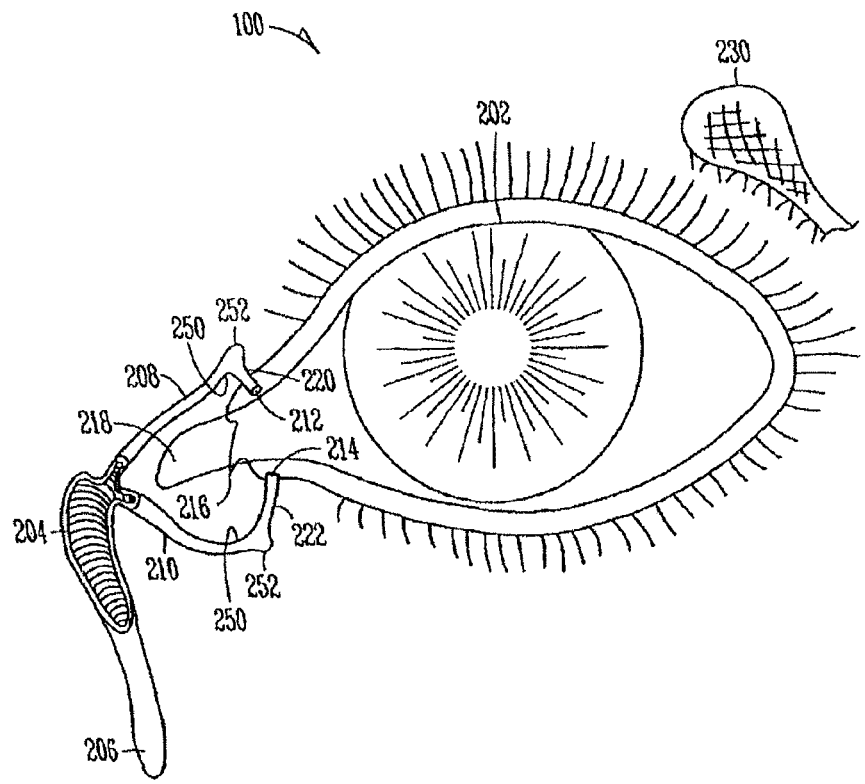
FIG. 2 illustrates another example of anatomical tissue structures associated with an eye, certain of these tissue structures providing a suitable environment in which a lacrimal implant can be used.

In some embodiments, the first member 305 is configured to extend into a canaliculus, while the second member 310 is configured to reside in the vertical portion 220, 222 of the canaliculus and to extend to the opening of, or out of the opening of, the associated puncta. When a lacrimal implant 300 of such configuration is inserted into a canaliculus, the intersection of the first axis A and the second axis B resides generally at a curvature of the canaliculus, such as the canaliculus curvature 250 in FIG. 2. In some embodiments, the first member 305 and the second member 310 are connected at the first angle, and that angle is at least about 45 degree, thereby forming an angled intersection between the first member and the second member. In various embodiments, when the lacrimal implant 300 is positioned in the lacrimal canaliculus, at least a portion of the angled intersection is biased against a canaliculus curvature of the lacrimal canaliculus. In this embodiment, the lacrimal implant 300 uses anatomical structures to facilitate the retention of the implanted lacrimal implant 300.

FIG. 3B depicts a side view of an exemplary lacrimal implant 300 of the invention. In some embodiments, the first member 305 includes an intermediate segment 315, a tip segment or tip 325, and a forward segment 320 in between the forward segment and tip segment. While the intermediate segment 315 is configured to be connected to the second member 310 by the third member or heel 330, the tip segment or tip 325 is configured to be inserted through a punctum prior to the other two segments of the first member 305 and prior to the other members of the lacrimal implant 300.

In some embodiments, the intermediate segment 315, the forward segment 320 and the tip segment or tip 325 are distinguishable from each other in general by their shapes. For example, in some embodiments, the intermediate segment 315 has a generally cylindrical shape with a diameter that is larger than the diameter of the tip segment or tip 325. In various embodiments, the forward segment 320 is tapered and has a conical shape, such that the forward segment 320 connects the intermediate segment 315 at one end and the tip segment or tip 325 at the other end. In some embodiments, the transition from the intermediate segment 315 to the forward segment 320 or the transition from the forward segment 320 to the tip segment or tip 325 is gradual and smooth such that no distinguishable edge exists at the transition.

In some embodiments, the intermediate segment 315 has a cylindrical shape. In various embodiments, the intermediate segment has a circular cross section, an elliptic cross section, or a polygonal cross section. The intermediate segment 315 is of any useful combination of length and diameter.

In some embodiments, the intermediate segment 315 has a diameter that is from about 0.4 mm to about 0.8 mm. For example, in some embodiments the diameter of the intermediate segment 315 is from about 0.53 mm to about 0.63 mm. In some embodiments, the intermediate segment 315 has a length along the first axis A that is from about 0.5 mm to about 3.5 mm. For example, in some embodiments the length of the intermediate segment 315 is from about 1 mm to about 2.8 mm.

In some embodiments, the tip segment or tip 325 is substantially a semi-sphere, or a portion of a semi-sphere. In exemplary embodiments, the semi-sphere, or portion therapy, has a radius that is from about 0.05 mm to about 0.3 mm. For example, in some embodiments, the radius of the tip segment or tip 325 is approximately 0.20 mm.

In some embodiments, the forward segment 320 has a conical configuration, tapering from the diameter of the intermediate segment 315 as it approaches the tip segment or tip 325. In some embodiments, the forward segment 320 is short and is tapered steeply, thus forming a wider taper angle. The forward segment 320 can also be long and tapered more gradually, thus forming a narrower taper angle. The tapering angle $\theta_3$ is illustrated in FIG. 3E. In some embodiments, the tapering angle $\theta_3$ is from about 2° to about 10°. For example, in some embodiments the tapering angle $\theta_3$ is from about 3.8° to about 7.8°. In some embodiments, $\theta_3$ is about 7.8°. In some embodiments, the forward segment 320 has a length along the first axis A that is from about 1 mm to about 5 mm. For example in some embodiments the length of forward segment 320 is from about 1.7 mm to about 3.5 mm.

Second Member 310

Referring to FIG. 3B, in some embodiments of implants of use in the present method, the second member 310 includes an upright segment 335 that extends from the third member or heel 330 generally along the direction of the second axis B. In various embodiments, the second member 310 further includes a head segment 340 that attaches to the upright segment 335 at an end opposite to the third member or heel 330. In some embodiments, the second member 310 is configured such that the upright segment 335 resides in the vertical portion of the canaliculus while the head segment 340 contacts the tissue surrounding the exterior of the punctum when the lacrimal implant 300 is positioned in the lacrimal canaliculus. In an exemplary embodiment, illustrated in FIGS. 3A-3F, the upright segment 335 has a cylindrical shape and the head segment 340 has an oval or oblong configuration. However, it will be appreciated that any other suitable shapes or configurations can be used and are within the scope of the present invention. For example, in various embodiments, the upright segment 335 is configured to be a conical; the head segment 340 is configured to have a circular, elliptical or polygonal cross section.

In some embodiments, the upright segment 335 has a characteristic diameter that is from about 0.7 mm to about 0.9 mm. For example, in some embodiments, the characteristic diameter of the upright segment 335 is about 0.8 mm.

In some embodiments, the upright segment 335 has a length in the direction of the second axis B that is from about 0.7 mm to about 1.5 mm. For example, in some embodiments the length of upright segment 335 along the direction of the second axis B is about 0.9 mm.

Generally, the head segment 340 has a cross section characterized by a minor axis and a major axis. The minor axis and the major axis refer to the shortest characteristic diameter and the longest characteristic diameter of the cross section, respectively. As such, the minor axis is equal to or less than the major axis. For instance, in some embodiments where the head segment 340 has a circular cross section, the minor axis and the major axis are of equal length. In various embodiments, the head segment 340 has an oval or oblong cross section, and the minor axis is shorter than the major axis. In some embodiments, the head segment 340 is elongated in a direction that is parallel to the first axis A. The major axis indicates the extension of the first member 305 and facilitates positioning of the lacrimal implant 300 in the punctum and canaliculus. In some embodiments, the major axis is from about 1.5 mm to about 2.5 mm. In various embodiments, the minor axis is from about 1 mm to about 1.5 mm. For example, in some embodiments, the major axis and the minor axis head segment 340 are approximately 1.9 mm and 1.3 mm respectively. In some embodiments, the head segment 340 has a thickness in the direction of the second axis that is from about 0.2 mm to about 0.4 mm. For example, in some embodiments, the thickness of the head segment 340 in the direction of the second axis is approximately 0.3 mm.

Referring still to FIG. 3B, exemplary head segment 340 comprises an under-surface 350 facing towards the third member or heel 330 and an outer-surface 355 that faces away from the third member or heel 330. Exemplary head segment 340 further comprises an edge surface 345 that couples the under-surface 350 and the outer-surface 355. The distance between the under-surface 350 and the outer-surface 355 can be readily varied. In some embodiments, the distance is from about 0.2 mm to about 0.4 mm.

In some embodiments, the outer-surface 355 is smaller than the under-surface 350 and is substantially flat. In various embodiments, the edge surface 345 is tapered, curved, angular, or multifaceted. In some embodiments, the edge surface 345 has a radius of curvature that is from about 0.2 mm to about 0.7 mm. In some embodiments, the under-surface 350 is in general flat and is configured to contact the exterior tissue surrounding the punctum when the lacrimal implant 300 is positioned in the lacrimal canaliculus.

Third Member or Heel 330

In some embodiments, the third member or heel 330 includes an upper surface 360, a lower surface 365, and side surfaces 370. In the illustrated embodiments, the bore 385 extends from the upper surface 360 into the third member or heel 330. In some embodiments, the upper surface 360 and the lower surface 365 are substantially flat and separated from each other by a distance. Such distance is readily variable and is typically about 0.3 mm to about 0.7 mm. For instance, in some embodiments, the upper surface 360 and the lower surface 365 are separated by a distance that is from about 0.4 mm to 0.6 mm (e.g., about 0.53 mm). In some embodiments, the upper surface 360 extends beyond the intersection with the second member 310. In some embodiments, the upper surface 360 extends beyond the intersection with the second member 310 for a distance that is from about 0.3 to about 0.6 mm. The upper surface 360 can also be joined with the side surfaces 370. In various embodiments, upper surface 360 and side surfaces 370 are joined by a curved intersection 380. In some embodiments, the curved intersection 380 has a radius of curvature that is from about 0.04 mm to about 0.08 mm.

Figures 3C, 3D:
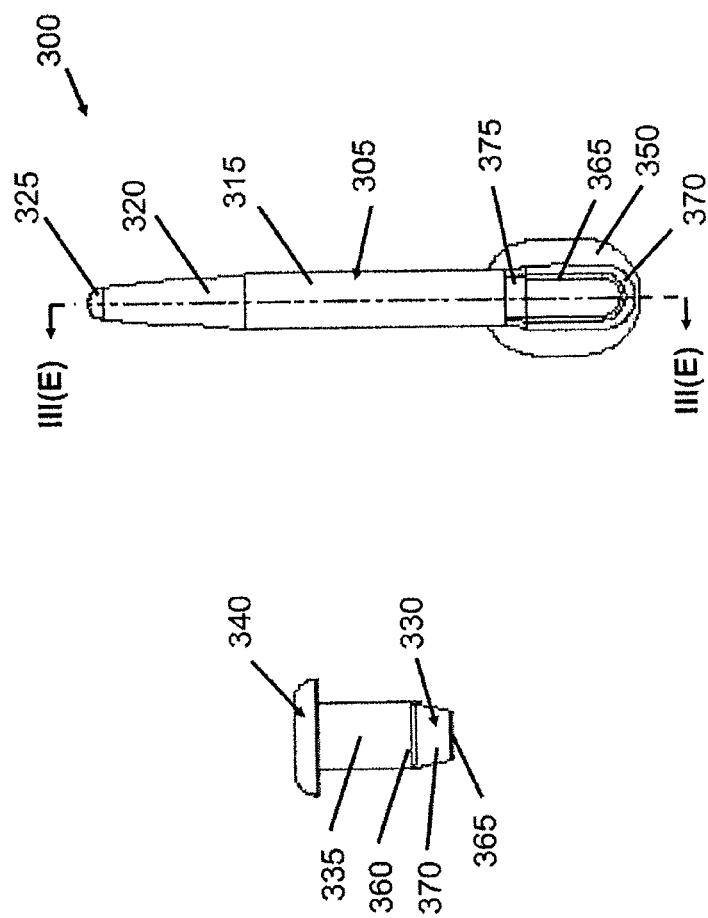
FIG. 3C is a side view illustrating the second member and the third member of an implant in accordance with an embodiment of the present invention.
FIG. 3D is a back view of an implant in accordance with an embodiment of the present invention.
Figures 3E, 3F:
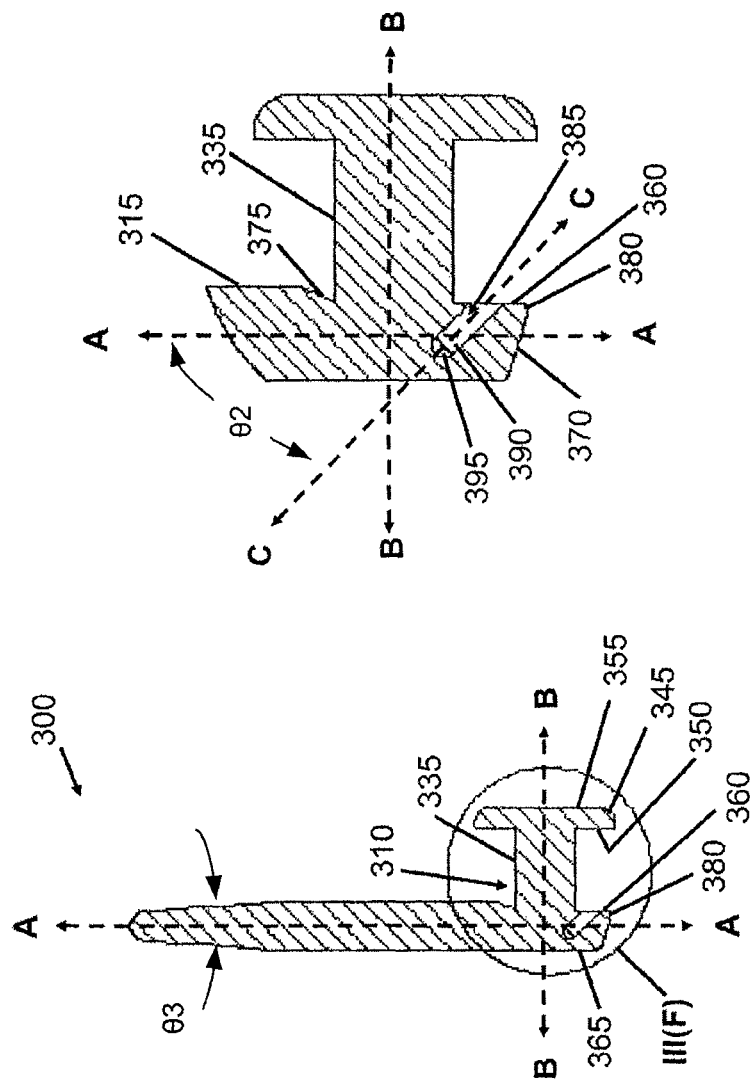
FIG. 3E is a cross-sectional view taken about line III(E)-III(E) of FIG. 3D depicting an implant with a bore, in accordance with an embodiment of the present invention.
FIG. 3F is a partially enlarged view of FIG. 3E taken about circle III(F) depicting the second member, the third member and a bore formed in the third member of an implant, in accordance with an embodiment of the present invention.

Referring now to FIGS. 3D and 3F, in some embodiments, the third member or heel 330 includes a heel connecting segment 375 configured to couple the third member or heel 330 to the first member 305, or to the intermediate segment 315 of the first member 305. The heel connecting segment 375 is of readily variable shape, including flat or curved structures. In FIG. 3F, a width of the heel connecting segment 375 in the direction of the second axis B varies along the direction of the first axis A. For example, the heel connecting segment 375 has a smaller width at or near the side surfaces 370 than the diameter of the intermediate segment 315 of the first member 305. In some embodiments, at or near the intersection with the intermediate segment 315, the heel connecting segment 375 increases the width and thus forms a notch as depicted in FIG. 3F. It will be appreciated that the notch can be either deeper or shallower along both the first axis A and the second axis B before it meets the first member 305 or the second member 310.

A notch is not a required feature in the implants of the present invention. In some embodiments, the heel connecting segment 375 has the same dimension as the diameter of the intermediate segment 315. For example, the thickness of the third member or heel 330 along the second axis B is equal to the diameter of the intermediate segment 315 of the first member 305. For example, in some embodiments, both the thickness of the third member or heel 330 in the direction of the second axis B and the diameter of the intermediate segment 315 are from about 0.53 mm to about 0.63 mm. In such configurations, the third member or heel 330 couples with the intermediate segment 315 without forming a notch, as illustrated by the alternative heel connecting segment 675 in FIG. 6.

By way of illustration, the third member or heel 330 depicted in FIGS. 3A-3F is substantially parallel to the first axis A of the first member 305. It would be appreciated that this is unnecessary. In some embodiments, the third member or heel 330 can form an angle with relation to the first axis A.

Bore 385

Exemplary structures of the bore 385 are detailed in FIGS. 3E and 3F, where a cross sectional view and a partial enlarged cross sectional view of the lacrimal implant 300 are provided. The bore 385 is configured to receive a tip or other protrusion of an external insertion tool for facilitating insertion of the lacrimal implant 300 into a lacrimal punctum. The configuration, including size, shape, angle ($\theta_2$) and position of the bore in the heel are readily adjustable to facilitate the mating of the insertion tool with the bore, the flexibility of the heel, or the retention of the lacrimal implants. Depending on the purpose or use of the implant and the materials used for making the heel, the characteristics of the bore noted above are readily varied. Configurations of the bore 385 disclosed herein are illustrative and any other suitable configurations are within the scope of the present invention.

In FIG. 3F, an exemplary bore 385 is characterized by a third axis C and a second angle $\theta_2$ that is defined by the first axis with respect to the third axis A in a similar way as the first angle $\theta_1$. In some embodiments, the second angle $\theta_2$ is from about 15° to about 90°. For example, in some embodiments, the second angle $\theta_2$ is about 45°.

In some embodiments, the bore 385 has a depth along the direction of the third axis C that is from about 0.3 mm to about 0.7 mm. For example, in some embodiments the depth of the bore 385 is approximately 0.4 mm and in some embodiments is approximately 0.6 mm, The bore 385 may include a bore shaft 390 that is generally cylindrical, with a circular, elliptical, oval, or polygonal cross section. The bore 385 may further include a bore tip 395 at which the bore shaft 390 terminates. An exemplary bore tip 395 generally has a semispherical configuration. In some embodiments, the bore shaft 390 has a characteristic diameter that is from about 0.1 mm to about 0.3 mm. In some embodiments, the characteristic diameter of the bore is approximately 0.17 mm. As will be appreciated, the shapes, sizes, orientations disclosed in the present application are illustrative, and any other suitable shapes, sizes, or orientations are within the scope of the present application. In addition, it will be appreciated that the opening of the bore can be positioned closer to the second member or closer to the edge of the heel.

Cavity 458

Figure 4A:
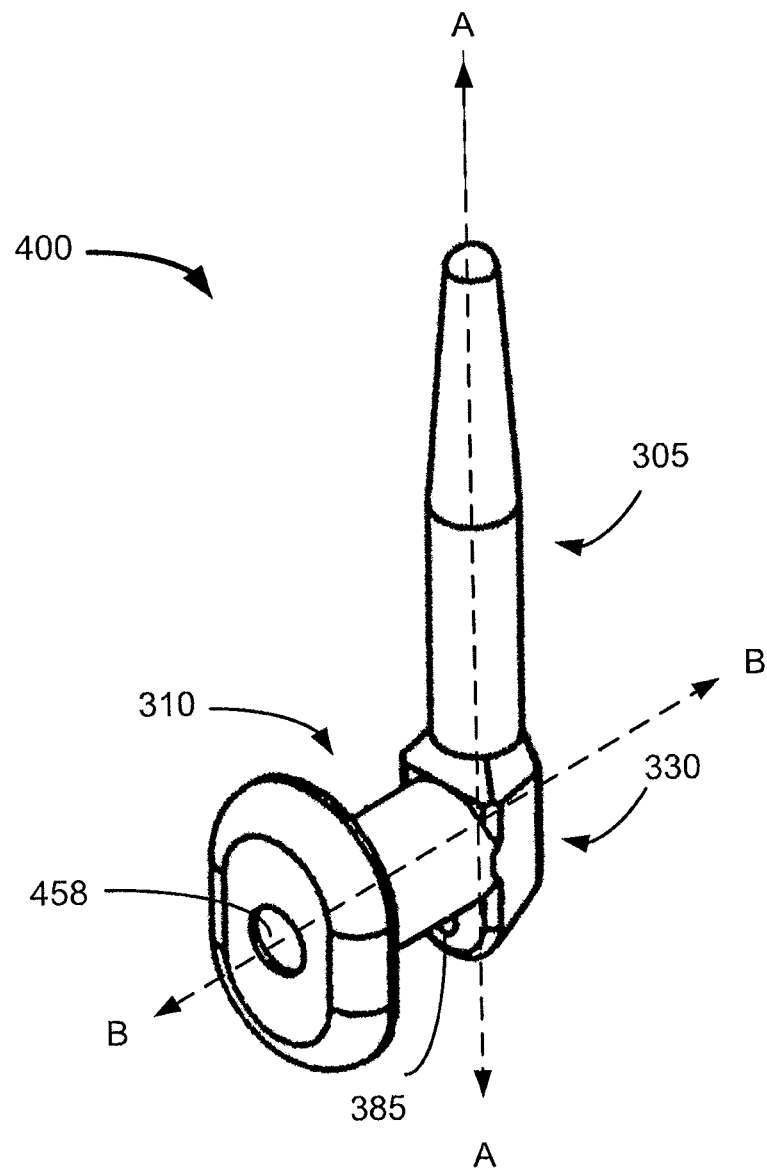
FIG. 4A provides a perspective view of an implant in accordance with an embodiment of the present invention.

FIG. 4A-4C illustrates an exemplary lacrimal implant 400 that is insertable through a lacrimal punctum 212, 214 and into its associated canaliculus 208, 210. In FIG. 4A, the lacrimal implant 400 comprises a cavity 458 that is configured to house a therapeutic agent core or other materials for release into an eye or surrounding tissues for treatment of various ocular, sinus or other diseases.

In the illustrated exemplary embodiment, the cavity 458 is formed in the head segment 340 and has an opening through the outer-surface 355. The cavity 458 can be shallow such that it stays within the head segment 340. The cavity 458 can be also deeper and extend beyond the head segment 340 and into the upright segment 335. Illustrated exemplary cavity 458 is in general substantially cylindrical with a circular cross section. Any other suitable configuration is within the scope of the present application. For example, in some embodiments, the cavity 458 has a truncated spherical configuration, or has a cylindrical configuration with an oblong or a polygonal cross section.

In some embodiments, the cavity 458 has a depth in the direction of the second axis B that is about from 0.2 mm to about 1.4 mm. For example, in some embodiments, the depth of the cavity 458 is approximately 1.2 mm. In some embodiments, the cavity 458 has a diameter that is from about 0.3 mm to about 0.7 mm. For example, in some embodiments the diameter of the cavity 458 is from about 0.42 mm to about 0.55 mm. In an exemplary embodiment, the cavity 458 extends into the upright segment 335, and the diameter of the cavity 458 is smaller than the diameter of the upright segment 335.

Referring to FIG. 4C, the cavity 458 includes a bottom 482. In various embodiments, the bottom 482 is rounded. In various embodiments, the rounded bottom has a radius of curvature that is from about 0.03 mm to about 0.07 mm.

Figure 5:
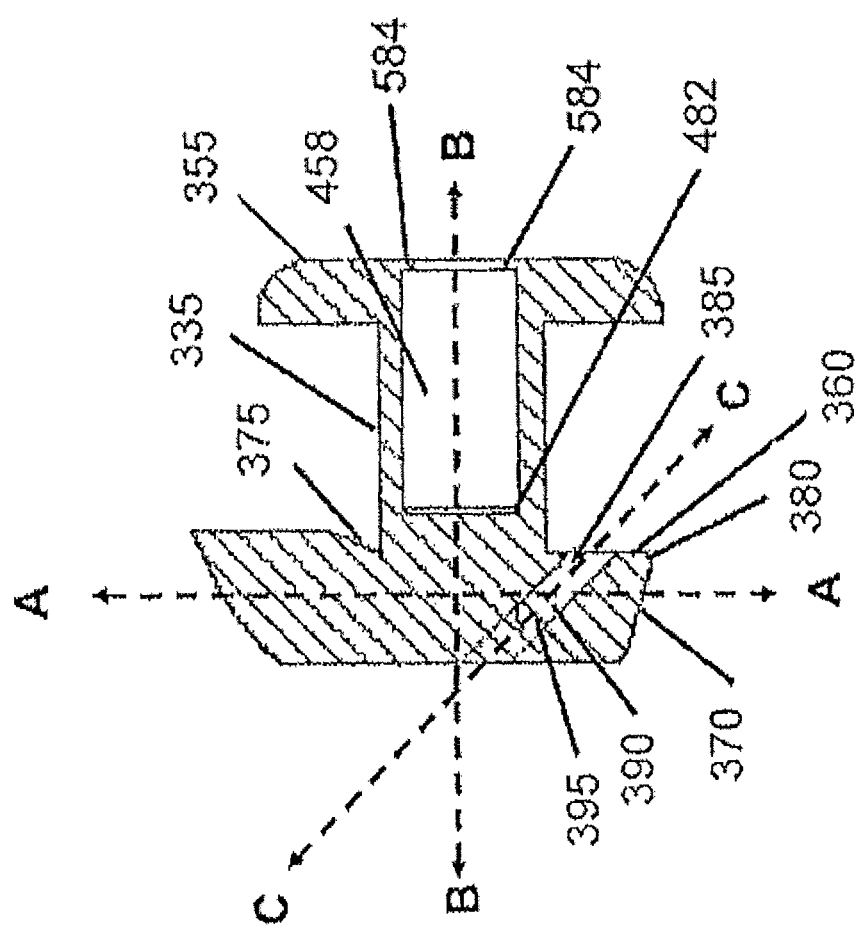
FIG. 5 provides a partial cross-sectional view of an implant in accordance with one embodiment of the present invention.
Figure 6:
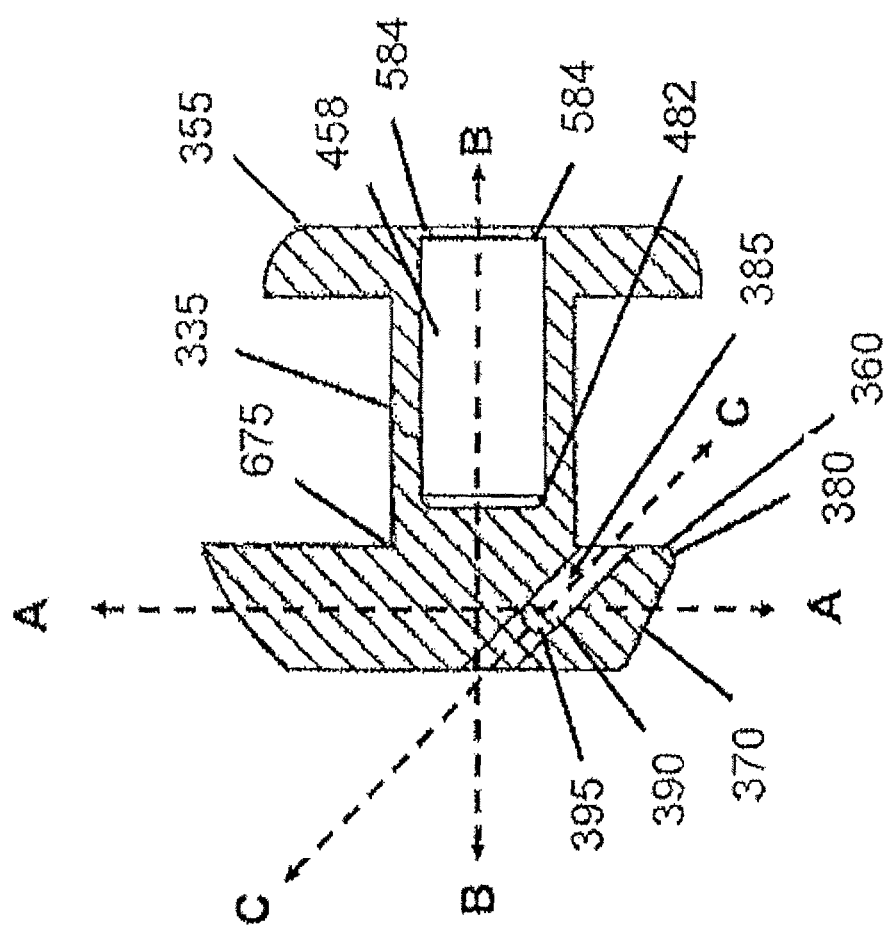
FIG. 6 provides a partial cross-section view of an implant in accordance with another embodiment of the present invention.

FIG. 5 depicts exemplary configurations of the cavity 458. In FIG. 5, the cavity 458 includes a lip 584 or other retaining structure positioned at the opening of the cavity 458. The lip 584 or the other retaining structure are optionally configured to partially enclose the cavity 458, e.g, prevent a therapeutic agent core or other materials from moving out of the cavity 458. In some embodiments, the lip 584 is a square cross sectional annulus that extends down from the outer-surface 355 into the cavity 458 and extends inwardly towards the center of the opening of the cavity 458. In some embodiments, the lip 584 is of a tab configuration and includes a plurality of spaced lips that extend inwardly into the opening of the cavity 458. The lip 584 may extend downwardly from about 0.02 mm to about 0.1 mm and inwardly from about 0.02 mm to about 0.1 mm. For example, in some embodiments, the lip 584 extends about 0.05 mm downwardly or inwardly.

Formation of Lacrimal Implants

Exemplary lacrimal implants of use in methods of the present invention are made of various materials including plastic, rubber, polymer, or composite. Exemplary lacrimal implants of the present invention formed from one or more material including plastic, rubber, polymer, composites, or other appropriate materials. In some embodiments, the lacrimal implants are formed from liquid silicone rubber. For instance, in exemplary embodiments, lacrimal implants are formed from a material marketed as NuSil 4840 liquid silicone rubber, NuSil 4870, or a mixture including such a liquid silicone rubber. Examples of such a mixture include a material marketed as 6-4800, which comprises NuSil 4840 with from about 1% to about 5%, e.g., from about 2% to about 4% 6-4800.

In some embodiments, the lacrimal implant is formed from biodegradable materials, for instance, biodegradable elastic materials including cross-linked polymers, such as poly (vinyl alcohol). In some embodiments, the lacrimal implant can comprise a co-polymer, such as silicone/polyurethane co-polymer, silicone/urethane, silicone/poly (ethylene glycol) (PEG), and silicone/2hydroxyethyl methacrylate (HEMA). As discussed in commonly-owned Utkhede et al., U.S. patent application Ser. No. 12/231,986, entitled "DRUG CORES FOR SUSTAINED RELEASE OF THERAPEUTIC AGENTS," filed Sep. 5, 2008, which is herein incorporated by reference in its entirety, urethane-based polymer and copolymer materials allow for a variety of processing methods and bond well to one another.

The hardness of the material is selected to facilitate or alter the retention of the lacrimal implant within the lacrimal punctum and its associated canaliculus. Accordingly, in some embodiments, a material having a durometer rating of from about 20D to about 80D, e.g., about 30D to about 70D, e.g., from about 40D to about 60D is of use to adjust parameters such as patient comfort and retention. For example, in some embodiments, the durometer rating of the material used to form the lacrimal implants is approximately 40D. Materials other than those exemplified above providing a durometer rating for the lacrimal implants within the stated ranges, and particularly that is about 40D are also of use. In some embodiments, a harder material or softer material is utilized for the entire lacrimal implant or for portions thereof. In such case, the lacrimal implants are formed from the materials that provide a durometer rating of about 70D.

In some embodiments, the lacrimal implants of use in the present methods are formed of multiple materials, where certain members or portions of the lacrimal implants are formed with materials having different properties. For example, in some embodiments the first member 305 is formed of a harder durometer rated material while the second member 310 is formed of a softer durometer rated material. In some embodiments, the first member 305 is formed of a softer durometer rated material while the second member 310 is formed of a harder durometer rated material. In some embodiments the third member or heel 330 is formed of a harder durometer rated material than one or more parts of the remainder of the second member 310. In various embodiments, the third member or heel 330 is formed of a softer durometer rated material than the remainder of the second member 310.

Exemplary implants of use in the invention can be formed by methods known in the art, including, but not limited to, machining a blank to the desired shape and size and molding the material forming the implant.

The implant can be one of any number of different designs that releases latanoprost or other intraocular pressure-reducing therapeutic agent(s) for a sustained period of time. The disclosures of the following patent documents, which describe example implant structure or processing embodiments for use in the methods of embodiments of the current invention and methods of making those implants, are incorporated herein by reference in their entirety: U.S. Application Ser. No. 60/871,864 (filed Dec. 26, 2006 and entitled Nasolacrimal Drainage System Implants for Drug Therapy); U.S. application Ser. No. 11/695,537 (filed Apr. 2, 2007 and entitled Drug Delivery Methods, Structures, and Compositions for Nasolacrimal System); U.S. U.S. application Ser. No. 12/332,219 (filed Dec. 10, 2008 and entitled Drug Delivery Methods, Structures, and Compositions for Nasolacrimal System); U.S. Application Ser. No. 60/787,775 (filed Mar. 31, 2006 and entitled Nasolacrimal Drainage System Implants for Drug Therapy); U.S. application Ser. No. 11/695,545 (filed Apr. 2, 2007 and entitled Nasolacrimal Drainage System Implants for Drug Therapy); U.S. Application Ser. No. 60/585,287 (filed Jul. 2, 2004 and entitled Treatment Medium Delivery Device and Methods for Delivery of Such Treatment Mediums to the Eye Using Such a Delivery Device); U.S. application Ser. No. 11/571,147 (filed Dec. 21, 2006 and entitled Treatment Medium Delivery Device and Methods for Delivery of Such Treatment Mediums to the Eye Using Such a Delivery Device); U.S. Application Ser. No. 60/970,696 (filed Sep. 7, 2007 and entitled Expandable Nasolacrimal Drainage System Implants); U.S. Application Ser. No. 60/974,367 (filed Sep. 21, 2007 and entitled Expandable Nasolacrimal Drainage System Implants); U.S. Application Ser. No. 60/970,699 (filed Sep. 7, 2007 and entitled Manufacture of Drug Cores for Sustained Release of Therapeutic Agents); U.S. Application Ser. No. 60/970,709 (filed Sep. 7, 2007 and entitled Nasolacrimal Drainage System Implants for Drug Delivery); U.S. Application Ser. No. 60/970,720 (filed Sep. 7, 2007 and entitled Manufacture of Expandable Nasolacrimal Drainage System Implants); U.S. Application Ser. No. 60/970,755 (filed Sep. 7, 2007 and entitled Prostaglandin Analogues for Implant Devices and Methods); U.S. Application Ser. No. 60/970,820 (filed Sep. 7, 2007 and entitled Multiple Drug Delivery Systems and Combinations of Drugs with Punctal Implants); U.S. Application Ser. No. 61/066,223 (filed Feb. 18, 2008 and entitled Lacrimal Implants and Related Methods); U.S. Application Ser. No. 61/049,347 (filed Apr. 30, 2008 and entitled Lacrimal Implants and Related Methods); U.S. Application Ser. No. 61/033,211 (filed Mar. 3, 2008 and entitled Lacrimal Implants and Related Methods); U.S. Application Ser. No. 61/049,360 (filed Apr. 30, 2008 and entitled Lacrimal Implants and Related Methods); U.S. Application Ser. No. 61/052,595 (filed May 12, 2008 and entitled Lacrimal Implants and Related Methods); U.S. Application Ser. No. 61/075,309 (filed Jun. 24, 2008 and entitled Lacrimal Implants and Related Methods); U.S. Application Ser. No. 61/154,693 (filed Feb. 23, 2009 and entitled Lacrimal Implants and Related Methods); U.S. Application Ser. No. 61/209,036 (filed Mar. 2, 2009 and entitled Lacrimal Implants and Related Methods); U.S. Application Ser. No. 61/209,630 (filed Mar. 9, 2009 and entitled Lacrimal Implants and Related Methods); U.S. Application Ser. No. 61/036,816 (filed Mar. 14, 2008 and entitled Lacrimal Implants and Related Methods); U.S. Application Ser. No. 61/271,862 (filed Jul. 27, 2009 and entitled Lacrimal Implants and Related Methods); U.S. Application Ser. No. 61/252,057 (filed Oct. 15, 2009 and entitled Lacrimal Implants and Related Methods); U.S. application Ser. No. 12/710,855 (filed Feb. 23, 2010 and entitled Lacrimal Implants and Related Methods); U.S. Application Ser. No. 60/871,867 (filed Dec. 26, 2006 and entitled Drug Delivery Implants for Inhibition of Optical Defects); U.S. application Ser. No. 12/521,543 (filed Dec. 31, 2009 and entitled Drug Delivery Implants for Inhibition of Optical Defects); U.S. Application Ser. No. 61/052,068 (filed May 9, 2008 and entitled Sustained Release Delivery of Latanoprost to Treat Glaucoma); U.S. Application Ser. No. 61/052,113 (filed May 9, 2008 and entitled Sustained Release Delivery of Latanoprost to Treat Glaucoma); U.S. Application Ser. No. 61/108,777 (filed Oct. 27, 2008 and entitled Sustained Release Delivery of Latanoprost to Treat Glaucoma); U.S. application Ser. No. 12/463,279 (filed May 8, 2009 and entitled Sustained Release Delivery of Active Agents to Treat Glaucoma and Ocular Hypertension); U.S. Application Ser. No. 61/049,337 (filed Apr. 30, 2008 and entitled Lacrimal Implants and Related Methods); U.S. application Ser. No. 12/432,553 (filed Apr. 29, 2009 and entitled Composite Lacrimal Insert and Related Methods); U.S. Application Ser. No. 61/049,317 (filed Apr. 30, 2008 and entitled Drug-Releasing Polyurethane Lacrimal Insert); U.S. application Ser. No. 12/378,710 (filed Feb. 17, 2009 and entitled Lacrimal Implants and Related Methods); U.S. Application Ser. No. 61/075,284 (filed Jun. 24, 2008 and entitled Combination Treatment of Glaucoma); U.S. application Ser. No. 12/490,923 (filed Jun. 24, 2009 and entitled Combination Treatment of Glaucoma); U.S. Application Ser. No. 61/134,271 (filed Jul. 8, 2008 and entitled Lacrimal Implant Body Including Comforting Agent); U.S. application Ser. No. 12/499,605 (filed Jul. 8, 2009 and entitled Lacrimal Implant Body Including Comforting Agent); U.S. Application Ser. No. 61/057,246 (filed May 30, 2008 and entitled Surface Treatment of Implants and Related Methods); U.S. Application Ser. No. 61/132,927 (filed Jun. 24, 2008 and entitled Surface Treated Implantable Articles and Related Methods); U.S. application Ser. No. 12/283,002 (filed Sep. 5, 2008 and entitled Surface Treated Implantable Articles and Related Methods); U.S. application Ser. No. 12/231,989 (filed Sep. 5, 2008 and entitled Lacrimal Implants and Related Methods); U.S. Application Ser. No. 61/049,317 (filed Apr. 30, 2008 and entitled Drug-Releasing Polyurethane Lacrimal Insert); U.S. application Ser. No. 12/231,986 (filed Sep. 5, 2008 and entitled Drug Cores for Sustained Release of Therapeutic Agents); U.S. Application Ser. No. 61/050,901 (filed May 6, 2008 and entitled Punctum Plug Detection); U.S. application Ser. No. 12/231,987 (filed Sep. 5, 2008 and entitled Lacrimal Implant Detection); U.S. Application Ser. No. 61/146,860 (filed Jan. 23, 2009 and entitled Sustained Release Delivery of One or More Anti-Glaucoma Agents); U.S. Application Ser. No. 61/152,909 (filed Feb. 16, 2009 and entitled Sustained Release Delivery of One or More Anti-Glaucoma Agents); U.S. Application Ser. No. 61/228,894 (filed Jul. 27, 2009 and entitled Sustained Release Delivery of One or More Anti-Glaucoma Agents); U.S. Application Ser. No. 61/277,000 (filed Sep. 18, 2009 and entitled Drug Cores for Sustained Ocular Release of Therapeutic Agents); U.S. application Ser. No. 12/692,452 (filed Jan. 22, 2010 and entitled Sustained Release Delivery of One or More Agents); U.S. Application Ser. No. 61/283,100 (filed Nov. 27, 2009 and entitled Lacrimal Implants Including Split and Insertable Drug Core); International Application Serial No. PCT/US2010/058129 (filed Nov. 26, 2010, published as WO 2011/066479 and entitled Lacrimal Implants Including Split and Insertable Drug Core); U.S. Application Ser. No. 61/139,456 (filed Dec. 19, 2008 and entitled Substance Delivering Punctum Implants and Methods); U.S. application Ser. No. 12/643,502 (filed Dec. 21, 2009 and entitled Substance Delivering Punctum Implants and Methods); U.S. application Ser. No. 10/825,047 (filed Apr. 15, 2004 and entitled Drug Delivery via Punctal Plug); U.S. application Ser. No. 12/604,202 (filed Oct. 22, 2009 and entitled Drug Delivery via Ocular Implant); International Application Serial No. PCT/US2005/023848 (filed Jul. 1, 2005, published as WO 2006/014434 and entitled Treatment Medium Delivery Device and Methods for Delivery); International Application Serial No. PCT/US2007/065792 (filed Apr. 2, 2007, published as WO 2007/115261 and entitled Drug Delivery Methods, Structures, and Compositions for Nasolacrimal System); and International Application Serial No. PCT/US2007/065789 (filed Apr. 2, 2007, published as WO 2007/115259 and entitled Nasolacrimal Drainage System Implants for Drug Therapy).

Figure 7:
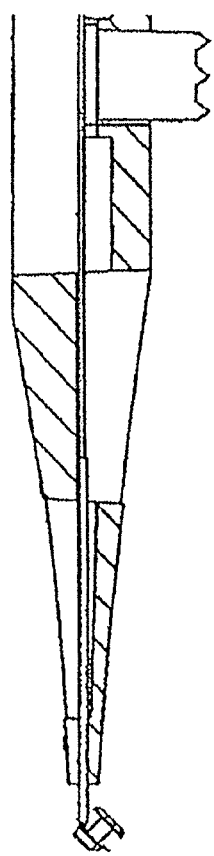
FIG. 7 depicts engagement of an insertion tool with an implant in accordance with an embodiment of the present invention.

Turning to FIG. 7, an exemplary insertion tool is shown engaged with an implant of the invention through meeting of pin 760 and insertion of the lacrimal implants into a lacrimal punctum. The lacrimal implants include the exemplary embodiments disclosed above, variations thereof, or any similar structures.

Retention

In various embodiments of the methods of the invention, an implant including a retention structure is employed to retain the implant in the punctum or canaliculus. The retention structure is attached to or integral with the implant body. The retention structure comprises an appropriate material that is sized and shaped so that the implant can be easily positioned in the desired tissue location, for example, the punctum or canaliculus. In some embodiments, the drug core may be attached to the retention structure via, at least in part, the sheath. In some embodiments, the retention structure comprises a hydrogel configured to expand when the retention structure is placed in the punctum. The retention structure can comprise an attachment member having an axially oriented surface. In some embodiments, expansion of the hydrogel can urge against the axially oriented surface to retain the hydrogel while the hydrogel is hydrated. In some embodiments, the attachment member can comprise at least one of a protrusion, a flange, a rim, or an opening through a portion of the retention structure. In some embodiments, the retention structure includes an implant body portion size and shape to substantially match an anatomy of the punctum and canaliculus.

The retention structure may have a size suitable to fit at least partially within the canalicular lumen. The retention structure can be expandable between a small profile configuration suitable for insertion and a large profile configuration to anchor the retention structure in the lumen, and the retention structure can be attached near the distal end of the drug core. In specific embodiments, the retention structure can slide along the drug core near the proximal end when the retention structure expands from the small profile configuration to the large profile configuration. A length of the retention structure along the drug core can be shorter in the large profile configuration than the small profile configuration.

In some embodiments, the retention structure is resiliently expandable. The small profile may have a cross section of no more than about 0.2 mm, and the large profile may have a cross section of no more than about 2.0 mm. The retention structure may comprise a tubular body having arms separated by slots. The retention structure can be disposed at least partially over the drug core.

In some embodiments, the retention structure is mechanically deployable and typically expands to a desired cross sectional shape, for example with the retention structure comprising a super elastic shape memory alloy such as Nitinol™. Other materials in addition to Nitinol™ can be used, for example resilient metals or polymers, plastically deformable metals or polymers, shape memory polymers, and the like, to provide the desired expansion. In some embodiments polymers and coated fibers available from Biogeneral, Inc. of San Diego, Calif. may be used. Many metals such as stainless steels and non-shape memory alloys can be used and provide the desired expansion. This expansion capability permits the implant to fit in hollow tissue structures of varying sizes, for example canaliculae ranging from 0.3 mm to 1.2 mm (i.e. one size fits all). Although a single retention structure can be made to fit canaliculae from 0.3 to 1.2 mm across, a plurality of alternatively selectable retention structures can be used to fit this range if desired, for example a first retention structure for canaliculae from 0.3 to about 0.9 mm and a second retention structure for canaliculae from about 0.9 to 1.2 mm. The retention structure has a length appropriate to the anatomical structure to which the retention structure attaches, for example a length of about 3 mm for a retention structure positioned near the punctum of the canaliculus. For different anatomical structures, the length can be appropriate to provide adequate retention force, e.g. 1 mm to 15 mm lengths as appropriate.

Although the implant body may be attached to one end of the retention structure as described above, in many embodiments the other end of the retention structure is not attached to the implant body so that the retention structure can slide over the implant body including the sheath body and drug core while the retention structure expands. This sliding capability on one end is desirable as the retention structure may shrink in length as the retention structure expands in width to assume the desired cross sectional width. However, it should be noted that many embodiments may employ a sheath body that does not slide in relative to the core.

In many embodiments, the retention structure can be retrieved from tissue. A projection, for example a hook, a loop, or a ring, can extend from a portion of the implant body to facilitate removal of the retention structure.

In some embodiments the sheath and retention structure can comprise two parts.

Figure 9:
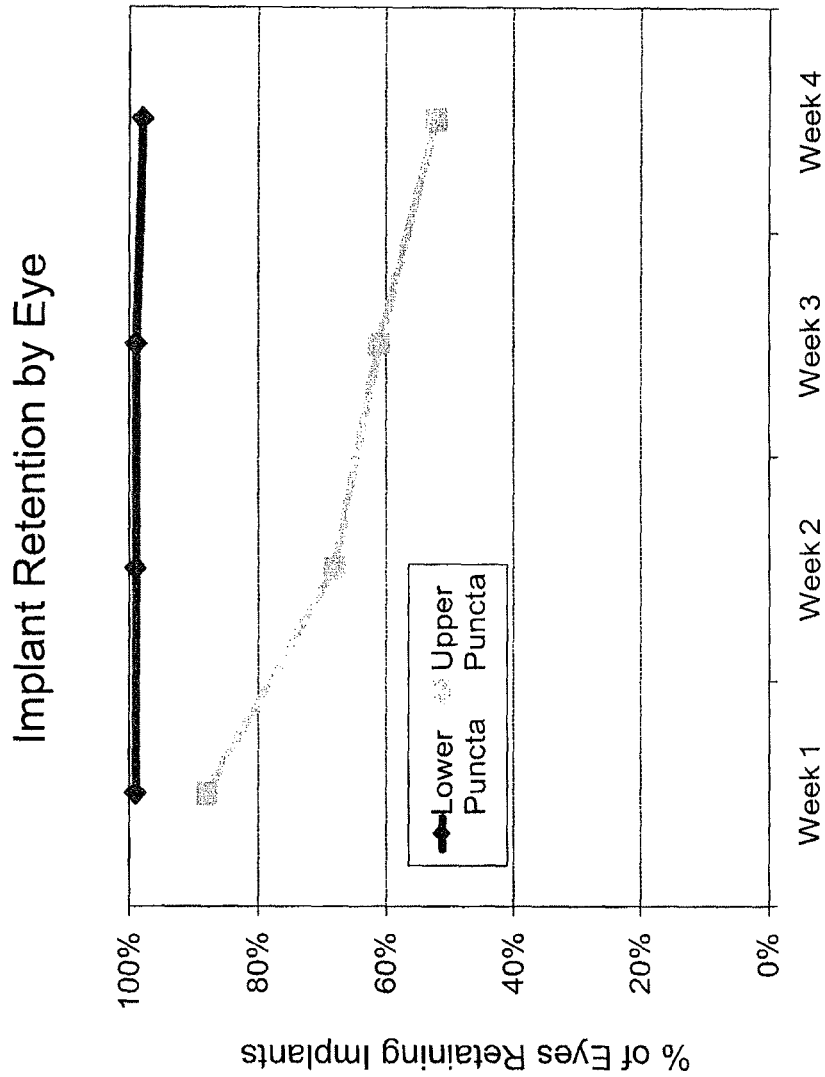
FIG. 9 is a plot comparing retention rates of an implant of the invention (lower punctum) with a commercial implant (upper punctum). The two implants are implanted in the same eye of the patient.

The lacrimal implants of the present invention have exceptional retention properties, and are retained in the punctum and canaliculus for a period that is enhanced relative to a commercially available plug (FIG. 9) based upon the percentage of eyes in which an implant was implanted retaining the implant over a selected time period.

In an exemplary embodiment, the method of the invention uses a lacrimal implant configured to remain implanted in a punctum for at least about 1 week, 2 weeks, 3 weeks, 4 weeks, 5 weeks, 6 weeks, 7 weeks, 8, weeks, 9 weeks 10 weeks, 11 weeks, or at least about 12 weeks or more. In an exemplary embodiment, the lacrimal implant is configured to be retained by the puncta for the duration of the intended sustained release of the therapeutic agent. In various embodiments, the duration of the intended sustained release of the therapeutic agent is at least about 1 week, 2 weeks, 3 weeks, 4 weeks, 5 weeks, 6 weeks, 7 weeks, 8 weeks, 9 weeks 10 weeks, 11 weeks, or at least about 12 weeks or more. In various embodiments at least about 95%, at least about 90%, at least about 85% or at least about 80% of the implanted implants are retained for the duration of the intended controlled release of the therapeutic agent. In an exemplary embodiment, the implant is retained by the puncta for a length of time to show therapeutic efficacy.

In various embodiments, the present invention provides for the use of implants having structural features that enhance the retention of the implant in a puncta. Amongst other features, the heel of the present implant (e.g., 330) is configured to come to rest in the lacrimal canaliculus ampulla (e.g., 252), effectively locking the implant into place. However, the inventors have recognized that to prevent rotation and relative movement of the implanted device, which plays a role in the displacement of the device, a first member was needed to maintain the heel in the ampula. Thus, the first member, e.g., 305, is configured to stabilize the punctal plug within the lacrimal canaliculus, prevent rotation and maintain positioning of the plug when the surrounding tissue moves.

Occlusive Element

In an exemplary embodiment, the methods of the invention use an implant having an occlusive element. An occlusive element can be mounted to and expandable with the retention structure to inhibit tear flow. An occlusive element may inhibit tear flow through the lumen, and the occlusive element may cover at least a portion of the retention structure to protect the lumen from the retention structure. The occlusive element comprises an appropriate material that is sized and shaped so that the implant can at least partially inhibit, even block, the flow of fluid through the hollow tissue structure, for example lacrimal fluid through the canaliculus. The occlusive material may be a thin walled membrane of a biocompatible material, for example silicone, that can expand and contract with the retention structure. The occlusive element is formed as a separate thin tube of material that is slid over the end of the retention structure and anchored to one end of the retention structure as described above. Alternatively, the occlusive element can be formed by dip coating the retention structure in a biocompatible polymer, for example silicone polymer. The thickness of the occlusive element can be in a range from about 0.01 mm to about 0.15 mm, and often from about 0.05 mm to 0.1 mm.

Insertion Tools

Installing the lacrimal implant of use in the invention can be facilitated by the use of an insertion tool. For example, in some embodiments the lacrimal implants and/or the inserter tool may include features or components that are found in U.S. Patent Application Publication No. 2009/0104248, U.S. Patent Application Publication No. 2010/0274204, U.S. Patent Application Publication No. 2009/0105749 and International Patent Application Publication No. WO 2011/066479, both of which are incorporated herein by reference in their entirety.

Therapeutic Agents and Therapeutic Agent Cores

Conventional drug delivery involving frequent periodic dosing is not ideal or practical in many instances. For example, with more toxic drugs, conventional periodic dosing can result in unfavorably high initial drug levels at the time of dosing, followed by low drug levels between doses often times below levels of therapeutic value. Likewise, conventional periodic dosing may not be practical or therapeutically effective in certain instances such as with pharmaceutical therapies targeting areas of the inner eye or brain in need of treatment such as the retina. Accordingly, in some embodiments, the lacrimal implant further includes one or more therapeutic agent within its structure. In various embodiments, the agent is dispersed throughout the device. In some embodiments, the agent is located at one or more distinct locations or zones of the device. In an exemplary embodiment, the therapeutic agent is located in a cavity of the device and the component holding the agent is referred to as a core.

In various embodiments, in which the agent is dispersed throughout the device, the rate and location of release of the agent is controlled by coating at least a component of the device with a material that is impermeable to the drug. In an exemplary embodiment, essentially the entire device is coated with the material with the exception of one or more gaps in the material through which the agent can elute into the eye or surrounding tissue. An exemplary coating is a Parylene coating (See, 2008/0181930, herein incorporated by reference).

In an exemplary embodiment, the lacrimal implant of the invention is configured as a sustained release device, releasing the incorporated therapeutic agent in a therapeutically effective manner, e.g., at a rate that provides a therapeutically effective dosage for at least about 1 week, 2 weeks, 3 weeks, 4 weeks, 5 weeks, 6 weeks, 7 weeks, 8, weeks, 9 weeks 10 weeks, 11 weeks, or at least about 12 weeks or more. In an exemplary embodiment, the lacrimal implant is configured to be retained by the puncta for the duration of the intended controlled release of the therapeutic agent. In various embodiments, the duration of the intended controlled release of the therapeutic agent is at least about 1 week, 2 weeks, 3 weeks, 4 weeks, 5 weeks, 6 weeks, 7 weeks, 8, weeks, 9 weeks 10 weeks, 11 weeks, or at least about 12 weeks or more. In various embodiments at least 95% of the implanted implants are retained for the duration of the intended controlled release of the therapeutic agent. In an exemplary embodiment, the implant is retained by the puncta for a length of time to show therapeutic efficacy.

In an exemplary embodiment, the implant is formatted as a unit dosage of the therapeutic agent. In various embodiments, the implant is formatted as a unit dosage of an antiglaucoma agent. In an exemplary embodiment, the antiglaucoma agent is a prostaglandin.

Elevated Intraocular Pressure

Ocular hypertension (OH) and primary open angle glaucoma (POAG) are caused by a build-up of aqueous humor in the anterior chamber primarily due to the eye's inability to properly drain aqueous fluid. The ciliary body, situated at the root of the iris, continuously produces aqueous humor. It flows into the anterior chamber and then drains via the angle between the cornea and iris through the trabecular meshwork and into a channel in the sclera. In the normal eye, the amount of aqueous humor being produced is equal to the amount that is draining out. However, in an eye in which this mechanism is compromised, intraocular pressure (IOP) rises. Elevated IOP represents a major risk factor for glaucomatous field loss. Results from several studies indicate that early intervention targeted at lowering intraocular pressure retards the progression of optic nerve damage and loss of visual fields that lead to decreased vision and blindness.

Latanoprost

Prostaglandins are regarded as potent ocular hypertensives; however, evidence accumulated in the last decade shows that some prostaglandins are highly effective ocular hypotensive agents and are ideally suited for the long-term medical management of glaucoma (see, for example, Bito, L. Z. Biological Protection with Prostaglandins Cohen, M. M., ed., Boca Raton, Fla., CRC Press Inc., 1985, pp. 231-252; and Bito, L. Z., Applied Pharmacology in the Medical Treatment of Glaucomas Drance, S. M. and Neufeld, A. H. eds., New York, Grune & Stratton, 1984, pp. 477-505). Such prostaglandins include PGF2α, PGF$_{1α}$, PGE$_2$, and certain lipid-soluble esters, such as $C_1$ to $C_5$ alkyl esters, e.g. 1-isopropyl ester, of such compounds.

Thus, in an exemplary embodiment, the therapeutic agent is a prostaglandin, including derivatives thereof. Prostaglandins are derivatives of prostanoic acid. Various types of prostaglandins are known, depending on the structure and substituents carried on the alicyclic ring of the prostanoic acid skeleton. Further classification is based on the number of unsaturated bonds in the side chains indicated by numerical subscripts after the generic type of prostaglandin (e.g., prostaglandin $E_1$ (PGE$_1$), prostaglandin $E_2$ (PGE$_2$)), and on the configuration of the substituents on the alicyclic ring indicated by α or β (e.g. prostaglandin F$_2$α (PGF$_2$α)). Any of these prostaglandins are of use in the present invention.

An exemplary therapeutic agent for use in the methods described herein is latanoprost. Latanoprost is a prostaglandin F$_{2α}$ analogue. Its chemical name is isopropyl-(Z)-7-[(1R,2R,3R,5S)3,5-dihydroxy-2-[(3R)-3-hydroxy-5-phenylpentyl]cyclopentyl]-5-heptenoate. Its molecular formula is $C_{26}H_{40}O_5$ and its chemical structure is:

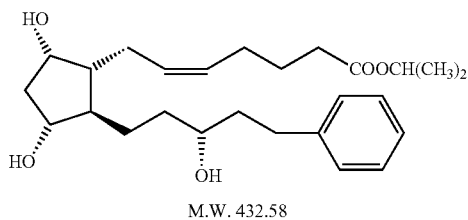

M.W. 432.58

Latanoprost is a colorless to slightly yellow oil that is very soluble in acetonitrile and freely soluble in acetone, ethanol, ethyl acetate, isopropanol, methanol and octanol. It is practically insoluble in water.

Latanoprost is believed to reduce intraocular pressure (IOP) by increasing the outflow of aqueous humor. Studies in animals and man suggest that the main mechanism of action is increased uveoscleral outflow of aqueous fluid from the eyes. Latanoprost is absorbed through the cornea where the isopropyl ester prodrug is hydrolyzed to the acid form to become biologically active. Studies in man indicate that the peak concentration in the aqueous humor is reached about two hours after topical administration.

Xalatan® latanoprost ophthalmic solution is a commercially available product indicated for the reduction of elevated IOP in patients with open-angle glaucoma or ocular hypertension. The amount of latanoprost in the commercially available product Xalatan® is approximately 1.5 micrograms/drop, which is the recommended daily total dose of latanoprost to one eye. As described above, eye drops, though effective, can be inefficient and require multiple applications to maintain the therapeutic benefit. Low patient compliance compounds these effects.

In various embodiments, the prostaglandin is latanoprost. In an illustrative embodiment, the unit dosage format includes from 40 μg to 100 μg of the therapeutic agent. In an exemplary embodiment, the implant includes about 46 μg or about 95 μg of latanoprost.

In an exemplary embodiment, the implant of the invention is a member of a pair of implants. In various embodiments, the pair of implants is configured as a unit dosage. In various embodiments, the implant is formatted as a unit dosage of an antiglaucoma agent. In an exemplary embodiment, the antiglaucoma agent is a prostaglandin. In various embodiments, the prostaglandin is latanoprost. In an illustrative embodiment, the unit dosage format includes from 40 μg to 100 μg of the therapeutic agent. In an exemplary embodiment, the unit dosage is 141 μg of latanoprost. In an exemplary embodiment, one implant includes about 46 μg of latanoprost and the other includes about 95 μg of latanoprost. In an exemplary embodiment, the unit dosage is a unit dosage for both eyes, including four implants as described herein.

In an exemplary embodiment, the implant of the invention is a member of a pair of implants. In various embodiments, the pair of implants is configured as a unit dosage. In various embodiments, the implant is formatted as a unit dosage of an antiglaucoma agent. In an exemplary embodiment, the antiglaucoma agent is a prostaglandin. In various embodiments, the prostaglandin is latanoprost. In an illustrative embodiment, the unit dosage format includes from 40 μg to 100 μg of the therapeutic agent. In an exemplary embodiment, the unit dosage is 190 μg of latanoprost. In an exemplary embodiment, each implant includes about 95 μg of latanoprost. In an exemplary embodiment, the unit dosage is a unit dosage for both eyes, including four implants as described herein.

Therapeutic Agent Core

In an exemplary embodiment, the methods of the invention utilize an implant including a distinct therapeutic agent core or integrated drug or other agent disposed in at least one of the first member 305 or the second member 310 of the implant body, to provide a sustained release of a therapeutic agent. For instance, the drug core or integrated drug or other agent disposed may be disposed in the cavity 458 of the lacrimal implant 400 to provide a sustained drug or other therapeutic agent release.

An exemplary implant of use in the methods of the invention is configured to deliver a therapeutic agent to one or more of an eye, nasal passage or inner ear system. In various embodiments, the drug is delivered systemically to the subject through the eye. A therapeutic agent core can comprise one or more therapeutic agents, and in some examples, one or more matrix materials to provide sustained release of the drug or other agents.

In various embodiments, the therapeutic agent core is inserted into cavity 458.

In various examples, the distinct drug core or integrated drug or other agent includes at least about 20 micrograms, at least about 40 micrograms, at least about 45 micrograms, at least 80 micrograms, or at least 95 micrograms of a drug (e.g., latanoprost), such as is further discussed in commonly-owned Butuner et al., U.S. patent application Ser. No. 12/463,279, entitled "SUSTAINED RELEASE DELIVERY OF ACTIVE AGENTS TO TREAT GLAUCOMA AND OCULAR HYPERTENSION," filed May 8, 2009, and commonly-owned Utkhede, U.S. Patent Application No. 61/277,000, entitled "IMPROVED DRUG CORES FOR SUSTAINED OCULAR RELEASE OF THERAPEUTIC AGENTS," filed Sep. 18, 2009, both of which are incorporated by reference in their entirety, including their descriptions of drug or other agent concentration.

The drug core can comprise one or more biocompatible materials capable of providing a sustained release of the one or more drugs or agents. The drug core can comprise a matrix including a substantially non-biodegradable silicone matrix with dissolvable inclusions of the drugs or agents located therein. The drug core can include other structures that provide sustained release of the drugs or agents, for example a biodegradable matrix, a porous drug core, a liquid drug core or a solid drug core. A matrix that includes the drugs or agents can be formed from either biodegradable or non-biodegradable polymers. In some examples, a non-biodegradable drug core can include silicone, acrylates, polyethylenes, polyurethane, polyurethane, hydrogel, polyester (e.g., DACRON™. from E.I. Du Pont de Nemours and Company, Wilmington, Del.), polypropylene, polytetrafluoroethylene (PTFE), expanded PTFE (ePTFE), polyether ether ketone (PEEK), nylon, extruded collagen, polymer foam, silicone rubber, polyethylene terephthalate, ultra high molecular weight polyethylene, polycarbonate urethane, polyurethane, polyimides, stainless steel, nickel-titanium alloy (e.g., Nitinol), titanium, stainless steel, cobalt-chrome alloy (e.g., ELGILOY™. from Elgin Specialty Metals, Elgin, Ill.; CONICHROME™. from Carpenter Metals Corp., Wyomissing, Pa.). In some examples, a biodegradable drug core can comprise one or more biodegradable polymers, such as protein, hydrogel, polyglycolic acid (PGA), polylactic acid (PLA), poly(L-lactic acid) (PLLA), poly(L-glycolic acid) (PLGA), polyglycolide, poly-L-lactide, poly-D-lactide, poly(amino acids), polydioxanone, polycaprolactone, polygluconate, polylactic acid-polyethylene oxide copolymers, modified cellulose, collagen, polyorthoesters, polyhydroxybutyrate, polyanhydride, polyphosphoester, poly(alpha-hydroxy acid) and combinations thereof. In some examples, the drug core can comprise a hydrogel polymer.

Table 1 shows exemplary drug insert silicones that may be used and associated cure properties, according to embodiments of the present invention. The drug core insert matrix material can include a base polymer comprising dimethyl siloxane, such as MED-4011, MED 6385 and MED 6380, each of which is commercially available from NuSil. The base polymer can be cured with a cure system such as a platinum-vinyl hydride cure system or a tin-alkoxy cure system, both commercially available from NuSil. In many embodiments, the cure system may comprise a known cure system commercially available for a known material, for example a known platinum vinyl hydride cure system with known MED-4011. In a specific embodiment shown in Table 1, 90 parts of MED-4011 can be combined with 10 parts of the crosslinker, such that the crosslinker comprises 10% of the mixture. A mixture with MED-6385 may comprise 2.5% of the crosslinker, and mixtures of MED-6380 may comprise 2.5% or 5% of the crosslinker.

TABLE 1

Drug Insert Silicone Selections

| Material | Base Polymer | Cure System | Crosslinker Percent |
|---|---|---|---|
| MED-4011 | Dimethyl siloxane Silica filler material | Platinum vinyl hydride system 10% | 10% |
| MED-6385 | Dimethyl siloxane Diatomaceous earth filler material | Tin-Alkoxy 2.5% | 2.5% |
| MED-6380 | Dimethyl siloxane without filler material | Tin-Alkoxy | 2.5 to 5% |

It has been determined according to the present invention that the cure system and type of silicone material can affect the curing properties of the solid drug core insert, and may potentially affect the yield of therapeutic agent from the drug core matrix material. In specific embodiments, curing of MED-4011 with the platinum vinyl hydride system can be inhibited with high concentrations of drug/prodrug, for example over 20% drug, such that a solid drug core may not be formed. In specific embodiments, curing of MED-6385 or MED 6380 with the tin alkoxy system can be slightly inhibited with high concentrations, e.g. 20%, of drug/prodrug. This slight inhibition of curing can be compensated by increasing the time or temperature of the curing process. For example, embodiments of the present invention can make drug cores comprising 40% drug and 60% MED-6385 with the tin alkoxy system using appropriate cure times and temperatures. Similar results can be obtained with the MED-6380 system the tin-alkoxy system and an appropriate curing time or temperature. Even with the excellent results for the tin alkoxy cure system, it has been determined according to the present invention that there may be an upper limit, for example 50% drug/prodrug or more, at which the tin-alkoxy cure system may not produce a solid drug core. In many embodiments, the latanoprost or other intraocular pressure-reducing therapeutic agent(s) in the solid drug core may be at least about 5%, for example a range from about 5% to 50%, and can be from about 20% to about 40% by weight of the drug core.

In a specific embodiment, drug cores with two different concentrations of Latanoprost are utilized in the method of the invention.

In one embodiment of the methods of the invention an implant with a drug core with 46 µg of Latanoprost was inserted into a punctual implant, See Table A.

TABLE A

Latanoprost Punctal Plug Delivery System (PPDS) Composition (46 µg)

| Material | Specific Formulation or ID | Description | L-PPDS, 46 µg with DMPC |
|---|---|---|---|
| Latanoprost | Chirogate International Everlight Chemical Industrial Corporation | GMP grade, neat oil | 46.0 µg |
| Silicone | NuSil MED-6385 (MAF 970) | Two part medical grade formulation | |
| | | Part A - proprietary silicone formulation | 60.1 µg |
| | | Part B - stannous octoate | 0.70 nL |
| Crosslinker | NuSil MED5-6382 (MAF 1289) | Only crosslinker is used from kit | 2.1 nL |
| Dimyristoyl Phosphatidylcholine (DMPC) | Nippon Fine Chemical | GMP grade, white solid | 8.6 µg |
| Tubing | Polyimide | Polyimide tube length (0.0155" inner diameter, with 0.0010" wall-medical grade) | 0.95 mm |
| Cyanoacrylate adhesive | Loctite ® 4305 ™ | Medical grade ethyl cyanoacrylate with photoinitiator | ~0.3 µg |

In another embodiment, a drug core with 95 µg of Latanoprost was made and inserted into a punctual plug, see Table B.

TABLE B

Latanoprost Punctal Plug Delivery System (PPDS) Composition (95 µg)

| Material | Specific Formulation or ID | Description | L-PPDS, 95 µg with DMPC |
|---|---|---|---|
| Latanoprost | Everlight Chemical Industrial Corporation | GMP grade, neat oil | 95.0 µg |
| Silicone | NuSil MED-6385 (MAF 970) | Two part medical grade formulation | |
| | | Part A - proprietary silicone formulation | 124.7 µg |
| | | Part B - stannous octoate | 0.70 nL |
| Crosslinker | NuSil MED5-6382 (MAF 1289) | Only crosslinker is used from kit | 4.8 nL |
| Dimyristoyl Phosphatidylcholine (DMPC) | Nippon Fine Chemical | GMP grade, white solid | 17.8 µg |
| Tubing | Polyimide | Polyimide tube length (0.0220" inner diameter, with 0.0010" wall-medical grade) | 0.95 mm |
| Cyanoacrylate adhesive | Loctite ® 4305 ™ | Medical grade ethyl cyanoacrylate with photoinitiator | ~0.3 µg |

Further discussion of drug-releasing or other agent-releasing drug cores can be found in commonly-owned Utkhede et al., U.S. patent application Ser. No. 12/231,986, entitled "DRUG CORES. FOR SUSTAINED RELEASE OF THERAPEUTIC AGENTS," filed Sep. 5, 2008, which is herein incorporated by reference in its entirety.

Sheath Body

In an exemplary embodiment, the implant of use in the methods of the invention includes a therapeutic agent core which is encased in a sheath body. The sheath body can comprise appropriate shapes and materials to control the migration of latanoprost or other anti-glaucoma agent from the drug core. In some embodiments, the sheath body houses the drug core and can fit snugly against the core. The sheath body is made from a material that is substantially impermeable to the latanoprost or other anti-glaucoma agent so that the rate of migration of the agent may be largely controlled by the exposed surface area of the drug core that is not covered by the sheath body. In many embodiments, migration of the latanoprost or other anti-glaucoma agent through the sheath body can be about one tenth of the migration of latanoprost or other anti-glaucoma agent through the exposed surface of the drug core, or less, often being one hundredth or less. In other words, the migration of the latanoprost or other anti-glaucoma agent through the sheath body is at least about an order of magnitude less that the migration of latanoprost or other anti-glaucoma agent through the exposed surface of the drug core. Suitable sheath body materials include polyimide, polyethylene terephthalate (hereinafter "PET"). The sheath body has a thickness, as defined from the sheath surface adjacent the core to the opposing sheath surface away from the core, from about 0.00025" to about 0.0015". The total diameter of the sheath that extends across the core ranges from about 0.2 mm to about 1.2 mm. The core may be formed by dip coating the core in the sheath material. Alternatively or in combination, the sheath body can comprise a tube and the core introduced into the sheath, for example as a liquid or solid that can be slid, injected or extruded into the sheath body tube. The sheath body can also be dip coated around the core, for example dip coated around a pre-formed core.

The sheath body can be provided with additional features to facilitate clinical use of the implant. For example, the sheath may receive a drug core that is exchangeable while the implant body, retention structure and sheath body remain implanted in the subject. The sheath body is often rigidly attached to the retention structure as described above, and the core is exchangeable while the retention structure retains the sheath body. In specific embodiments, the sheath body can be provided with external protrusions that apply force to the sheath body when squeezed and eject the core from the sheath body. Another drug core can then be positioned in the sheath body. In many embodiments, the sheath body or retention structure may have a distinguishing feature, for example a distinguishing color, to show placement such that the placement of the sheath body or retention structure in the canaliculus or other body tissue structure can be readily detected by the subject. The retention element or sheath body may comprise at least one mark to indicate the depth of placement in the canaliculus such that the retention element or sheath body can be positioned to a desired depth in the canaliculus based on the at least one mark.

Therapeutic Agents

Generally, pharmaceutically active agents or drugs useful in the methods of the present invention can be any compound, composition of matter, or mixtures thereof that can be delivered from an implant, such as those described herein, to produce a beneficial and useful result to, for example, the eye, especially an agent effective in obtaining a desired local or systemic physiological or pharmacological effect.

Examples of such agents include, but are not limited to, anesthetics and pain killing agents such as lidocaine and related compounds, benzodiazepam and related compounds and the like; anti-cancer agents such as 5-fluorouracil, adriamycin and related compounds and the like; anti-fungal agents such as fluconazole and related compounds and the like; anti-viral agents such as trisodium phosphomonoformate, trifluorothymidine, acyclovir, ganciclovir, DDI, AZT and the like; cell transport/mobility impending agents such as colchicine, vincristine, cytochalasin B and related compounds and the like; antiglaucoma drugs (e.g. adrenergic agonists, adrenergic antagonists (beta blockers), carbonic anhydrase inhibitors (CAIs, systemic and topical), parasympathomimetics, prostaglandins and hypotensive lipids, and combinations thereof), antimicrobial agent (e.g., antibiotic, antiviral, antiparacytic, antifungal, etc.), a corticosteroid or other anti-inflammatory (e.g., an NSAID or other analgesic and pain management compounds), a decongestant (e.g., vasoconstrictor), an agent that prevents of modifies an allergic response (e.g., an antihistamine, cytokine inhibitor, leucotriene inhibitor, IgE inhibitor, immunomodulator), a mast cell stabilizer, cycloplegic, mydriatic or the like.

Other agents that can be incorporated into devices of use in the invention include antihypertensives; decongestants such as phenylephrine, naphazoline, tetrahydrazoline and the like; immunological response modifiers such as muramyl dipeptide and related compounds and the like; peptides and proteins such as cyclosporin, insulin, growth hormones, insulin related growth factor, heat shock proteins and related compounds and the like; steroidal compounds such as dexamethasone, prednisolone and related compounds and the like; low solubility steroids such as fluocinolone acetonide and related compounds and the like; carbonic anhydrase inhibitors; diagnostic agents; antiapoptosis agents; gene therapy agents; sequestering agents; reductants such as glutathione and the like; antipermeability agents; antisense compounds; antiproliferative agents; antibody conjugates; antidepressants; bloodflow enhancers; antiasthmatic drugs; antiparasiticagents; non-steroidal anti inflammatory agents such as ibuprofen and the like; nutrients and vitamins: enzyme inhibitors: antioxidants; anticataract drugs; aldose reductase inhibitors; cytoprotectants; cytokines, cytokine inhibitors, and cytokin protectants; uv blockers; mast cell stabilizers; anti neovascular agents such as antiangiogenic agents, e.g., matrix metalloprotease inhibitors and the like.

Representative examples of additional pharmaceutically active agent for use herein include, but are not limited to, neuroprotectants such as nimodipine and related compounds and the like; antibiotics such as tetracycline, chlortetracycline, bacitracin, neomycin, polymyxin, gramicidin, oxytetracycline, chloramphenicol, gentamycin, erythromycin and the like; anti-infectives; antibacterials such as sulfonamides, sulfacetamide, sulfamethizole, sulfisoxazole; nitrofurazone, sodium propionate and the like; antiallergenics such as antazoline, methapyriline, chlorpheniramine, pyrilamine, prophenpyridamine and the like; anti-inflammatories such as hydrocortisone, hydrocortisone acetate, dexamethasone 21-phosphate, fluocinolone, medrysone, methylprednisolone, prednisolone 21-phosphate, prednisolone acetate, fluoromethalone, betamethasone, triminolone and the like; miotics; anti-cholinesterase such as pilocarpine, eserine salicylate, carbachol, di-isopropyl fluorophosphate, phospholine iodine, demecarium bromide and the like; miotic agents; mydriatics such as atropine sulfate, cyclopentolate, homatropine, scopolamine, tropicamide, eucatropine, hydroxyamphetamine and the like; sympathomimetics such as epinephrine and the like; and prodrugs such as, for example, those described in Design of Prodrugs, edited by Hans Bundgaard, Elsevier Scientific Publishing Co., Amsterdam, 1985. In addition to the foregoing agents, other agents suitable for treating, managing, or diagnosing conditions in a mammalian organism may be entrapped in the copolymer and administered using the drug delivery systems of the current invention. Once again, reference may be made to any standard pharmaceutical textbook such as, for example, Remington's Pharmaceutical Sciences for pharmaceutically active agents.

Any pharmaceutically acceptable form of the foregoing therapeutically active agent may be employed in the practice of the present invention, e.g., the free base; free acid; pharmaceutically acceptable salts, esters or amides thereof, e.g., acid additions salts such as the hydrochloride, hydrobromide, sulfate, bisulfate, acetate, oxalate, valerate, oleate, palmitate, stearate, laurate, borate, benzoate, lactate, phosphate, tosylate, mesylate, citrate, maleate, fumarate, succinate, tartrate, ascorbate, glucoheptonate, lactobionate, and lauryl sulfate salts and the like; alkali or alkaline earth metal salts such as the sodium, calcium, potassium and magnesium salts and the like; hydrates; enantiomers; isomers; stereoisomers; diastereoisomers; tautomers; polymorphs, mixtures thereof, prodrugs thereof or racemates or racemic mixtures thereof.

Additional agents that can be used with the present methods utilizing lacrimal implants include, but are not limited to, drugs that have been approved under Section 505 of the United States Federal Food, Drug, and Cosmetic Act or under the Public Health Service Act, some of which can be found at the U.S. Food and Drug Administration (FDA) website http://www.accessdatalda.gov/scripts/cder/drugsatfda/index. The present lacrimal implants can also be used with drugs listed in the Orange Book, either in paper or in electronic form, which can be found at the FDA Orange Book website (http://www.fda.gov/cder/ob/)), that has or records the same date as, earlier date than, or later date than, the filing date of this patent document. For example, these drugs can include, among others, dorzolamide, olopatadine, travoprost, bimatoprost, cyclosporin, brimonidine, moxifloxacin, tobramycin, brinzolamide, aciclovir timolol maleate, ketorolac tromethamine, prednisolone acetate, sodium hyaluronate, nepafenac, bromfenac, diclofenac, flurbiprofen, suprofenac, binoxan, patanol, dexamethasone/tobramycin combination, moxifloxacin, or acyclovir.

Further discussion of drugs or other agents can be found in commonly-owned U.S. Patent Application Publication No. 2009/0104248, U.S. Patent Application Publication No. 2010/0274204, and U.S. Patent Application Publication No. 2009/0105749, which are herein incorporated by reference in its entirety.

Actual dosage levels of the pharmaceutically active agent(s) in the drug delivery systems of use in the present invention may be varied to obtain an amount of the pharmaceutically active agent(s) that is effective to obtain a desired therapeutic response for a particular system and method of administration. The selected dosage level therefore depends upon such factors as, for example, the desired therapeutic effect, the route of administration, the desired duration of treatment, and other factors. The total daily dose of the pharmaceutically active agent(s) administered to a host in single or divided doses can vary widely depending upon a variety of factors including, for example, the body weight, general health, sex, diet, time and route of administration, rates of absorption and excretion, combination with other drugs, the severity of the particular condition being treated, etc. Generally, the amounts of pharmaceutically active agent(s) present in the drug delivery systems of the present invention can range from about 0.1% w/w to about 60% w/w and preferably from about 1% w/w to about 50% w/w.

Examples of diseases or disorders that can be treated according to the methods of the invention with above-listed agents include, but are not limited to, glaucoma, pre- and post-surgical ocular treatments, dry eye, anti-eye allergy, anti-infective, post-surgical inflammation or pain, respiration-related disorders, such as allergies, inner ear disorders, such as dizziness or migraines, or other systemic disorders, such as hypertension, cholesterol management, pulmonary disorders or immunological disorders. In some examples, the therapeutic agent can include a lubricant or a surfactant, for example a lubricant to treat dry eye. In other examples, the therapeutic agent can include an absorbent capable of absorbing tear from an eye.

Additional diseases treatable by a method of the invention include matrix controlled diffusion drug delivery systems of the present invention may be used in a broad range of therapeutic applications. The matrix controlled diffusion drug delivery systems of the present invention are particularly useful in the treatment of ophthalmic diseases, disorders and/or injuries. Representative examples of such ophthalmic diseases, disorders or injuries include, but are not limited to, diabetic retinopathy, glaucoma, macular degeneration, retinitis pigmentosa, retinal tears or holes, retinaldetachment, retinal ischemia, acute retinopathies associated with trauma, inflammatory mediated degeneration, post-surgical complications, damage associated with laser therapy including photodynamic therapy (PDT), surgical light induced iatrogenic retinopathy, drug-induced retinopathies, autosomal dominant optic atrophy, toxic/nutritional amblyopias; leber's hereditary optic neuropathy (LHOP), other mitochondrial diseases with ophthalmic manifestations or complications, angiogenesis; atypical RP; bardetbiedl syndrome; blue-cone monochromacy; cataracts; central areolar choroidal dystrophy; choroideremia; cone dystrophy; rod dystrophy; cone-rod dystrophy; rod-cone dystrophy; congenital stationary night blindness; cytomegalovirus retinitis; diabetic macular edema; dominant drusen; giant cell arteritis (GCA); goldmann-favre dystrophy; graves' ophthalmopathy; gyrate atrophy; hydroxychloroquine; iritis; juvenile retinoschisis; kearns-sayre syndrome; lawrence-moon bardet-biedl syndrome; leber congenital amaurosis; lupus-induced cotton wool spots; macular degeneration, dry form; macular degeneration, wet form; macular drusen; macular dystrophy; malattia leventinese; ocular histoplasmosis syndrome; oguchi disease; oxidative damage; proliferative vitreoretinopathy; refsum disease; retinitis *punctata albescens*; retinopathy of prematurity; rod monochromatism; RP and usher syndrome; scleritis; sector RP; sjogren-larsson syndrome; sorsby fundus dystrophy; stargardt disease and other retinal diseases.

The methods of the present invention can be administered to a mammal in need of treatment by way of a variety of routes. For example, drug delivery systems may be used by implantation within a portion of the body in need of localized drug delivery, e.g., the interior portion of an eye. However, the exemplary matrix controlled diffusion drug delivery systems may likewise be used in accordance with other surgical procedures known to those skilled in the field of ophthalmology. For example, the drug delivery systems can be administered to the region of the eye in need of treatment employing instruments known in the art, e.g., a flexible microcatheter system or cannula disclosed in U.S. Patent Application Publication No. 2002/0002362, or the intraretinal delivery and withdrawal systems disclosed in U.S. Pat. Nos. 5,273,530 and 5,409,457, the contents of each which are incorporated by reference herein. The pharmaceutically active agent may be released from the drug delivery device over a sustained and extended period of time. Optionally, the drug release rate may also be controlled through the attachment of an inert diffusion barrier by way of, for example, surface treatment of the drug delivery device. The surface treatment may be applied through a variety of surface treatment techniques known in the art, e.g., oxidative plasma, evaporative deposition, dip coating or extrusion techniques.

The therapeutic agent can be present in the device in a formulation with a pharmaceutically acceptable carrier, e.g., excipients, suspending agents, diluents, fillers, salts, buffers, stabilizers, solubilizers, solvents, dispersion media, coatings, isotonic agents, and other materials known in the art. The pharmaceutical formulation optionally includes potentiators, complexing agents, targeting agents, stabilizing agents, cosolvents, pressurized gases, or solubilizing conjugates.

Exemplary excipients include sugars such as lactose, sucrose, mannitol, or sorbitol; cellulose preparations such as, maize starch, wheat starch, rice starch, potato starch, gelatin, gum tragacanth, methyl cellulose, hydroxypropylmethylcellulose, sodium caroxymethylcellulose, and/or polyvinylpyrrolidone (PVP). Preferred excipients include lactose, gelatin, sodium carboxymethyl cellulose, and low molecular weight starch products.

Exemplary suspending agents that can serve as valve lubricants in pressurized pack inhaler systems are desirable. Such agents include oleic acid, simple carboxylic acid derivatives, and sorbitan trioleate.

Exemplary diluents include water, saline, phosphate-buffered citrate or saline solution, and mucolytic preparations. Other diluents that can be considered include alcohol, propylene glycol, and ethanol; these solvents or diluents are more common in oral aerosol formulations. Physiologically acceptable diluents that have a tonicity and pH compatible with the alveolar apparatus are desirable. Preferred diluents include isotonic saline, phosphate buffered isotonic solutions whose tonicity have been adjusted with sodium chloride or sucrose or dextrose or mannitol.

Exemplary fillers include glycerin, propylene glycol, ethanol in liquid or fluid preparations. Suitable fillers for dry powder inhalation systems include lactose, sucrose, dextrose, suitable amino acids, and derivatives of lactose. Preferred fillers include glycerin, propylene glycol, lactose and certain amino acids.

Exemplary salts include those that are physiologically compatible and provide the desired tonicity adjustment. Monovalent and divalent salts of strong or weak acids are desirable. Preferred salts include sodium chloride, sodium citrate, ascorbates, sodium phosphates.

Exemplary buffers include phosphate or citrate buffers or mixed buffer systems of low buffering capacity. Preferred buffers include phosphate or citrate buffers.

Making the Implant

Those of skill in the art will be familiar with various methods useful for making the implants described as being of use in the methods disclosed herein. Particular methods are described in the above-identified patent documents, the disclosures of which are incorporated herein by reference in their entirety.

For example, drug cores as described above may be fabricated with different cross sectional sizes of 0.006 inches, 0.012 inches, and 0.025 inches. Drug concentrations in the core may be 5%, 10%, 20%, 30% in a silicone matrix. These drug cores can be made with a syringe tube and cartridge assembly, mixing latanoprost or other intraocular pressure-reducing therapeutic agent(s) with silicone, and injecting the mixture into a polyimide tube which is cut to desired lengths and sealed. The length of the drug cores can be approximately 0.80 to 0.95 mm, which for a diameter of 0.012 inches (0.32 mm) corresponds to total latanoprost or other intraocular pressure-reducing therapeutic agent(s) content in the drug cores of approximately 3.5 micrograms, 7 micrograms, 14 micrograms and 21 micrograms for concentrations of 5%, 10%, 20% and 30%, respectively.

Syringe Tube and Cartridge Assembly: 1. Polyimide tubing of various diameters (for example 0.006 inches, 0.0125 inches and 0.025 inches) can be cut to 15 cm length. 2. The polyimide tubes can be inserted into a Syringe Adapter. 3. The polyimide tube can be adhesive bonded into luer adapter (Loctite, low viscosity UV cure). 4. The end of the assembly can then be trimmed. 5. The cartridge assembly can be cleaned using distilled water and then with methanol and dried in oven at 60 degrees C.

The latanoprost or other intraocular pressure-reducing therapeutic agent(s) can be mixed with silicone. Latanoprost or other intraocular pressure-reducing therapeutic agent(s) may be provided as a 1% solution in methylacetate. The appropriate amount of solution can be placed into a dish and using a nitrogen stream, the solution can be evaporated until only the latanoprost or other intraocular pressure-reducing therapeutic agent(s) remains. The dish with the latanoprost or other intraocular pressure-reducing therapeutic agent(s) oil can be placed under vacuum for 30 minutes. This latanoprost or other intraocular pressure-reducing therapeutic agent(s) can then be combined with silicone, with three different concentrations of latanoprost or other intraocular pressure-reducing therapeutic agent(s) (5%, 10% and 20%) in silicone NuSil 6385 being injected into tubing of different diameters (0.006 in, 0.012 in and 0.025 inches) to generate 3×3 matrixes. The percent of latanoprost or other intraocular pressure-reducing therapeutic agent(s) to silicone is determined by the total weight of the drug matrix. Calculation: Weight of latanoprost or other intraocular pressure-reducing therapeutic agent(s)/(weight of latanoprost or other intraocular pressure-reducing therapeutic agent(s)+weight of silicone)×100=percent drug.

The tube can then be injected: 1. The cartridge and polyimide tubes assembly can be inserted into a 1 ml syringe. 2. One drop of catalyst (MED-6385 Curing Agent) can be added in the syringe. 3. Excess catalyst can be forced out of the polyimide tube with clean air. 4. The syringe can then be filled with silicone drug matrix. 5. The tube can then be injected with drug matrix until the tube is filled or the syringe plunger becomes too difficult to push. 6. The distal end of the polyimide tube can be closed off and pressure can be maintained until the silicone begins to solidify. 7. Allow to cure at room temperature for 12 hours. 8. Place under vacuum for 30 minutes. 9. The tube can then be place in the correct size trim fixture (prepared in house to hold different size tubing) and drug inserts can be cut to length (0.80-0.95 mm).

Release of Latanoprost or Other Intraocular Pressure-Reducing Therapeutic Agent(s) at Effective Levels The rate of release of latanoprost or other intraocular pressure-reducing therapeutic agent(s) can be related to the concentration of latanoprost or other intraocular pressure-reducing therapeutic agent(s) dissolved in the drug core. In some embodiments, the drug core comprises non-therapeutic agents that are selected to provide a desired solubility of the latanoprost or other intraocular pressure-reducing therapeutic agent(s) in the drug core. The non-therapeutic agent of the drug core can comprise polymers as described herein, and additives. A polymer of the core can be selected to provide the desired solubility of the latanoprost or other intraocular pressure-reducing therapeutic agent(s) in the matrix. For example, the core can comprise hydrogel that may promote solubility of hydrophilic treatment agent. In some embodiments, functional groups can be added to the polymer to provide the desired solubility of the latanoprost or other intraocular pressure-reducing therapeutic agent(s) in the matrix. For example, functional groups can be attached to silicone polymer.

Additives may be used to control the concentration of latanoprost or other intraocular pressure-reducing therapeutic agent(s) by increasing or decreasing solubility of the latanoprost or other intraocular pressure-reducing therapeutic agent(s) in the drug core so as to control the release kinetics of the latanoprost or other intraocular pressure-reducing therapeutic agent(s). The solubility may be controlled by providing appropriate molecules or substances that increase or decrease the content of latanoprost or other intraocular pressure-reducing therapeutic agent(s) in the matrix. The latanoprost or other intraocular pressure-reducing therapeutic agent(s) content may be related to the hydrophobic or hydrophilic properties of the matrix and latanoprost or other intraocular pressure-reducing therapeutic agent(s). For example, surfactants and salts can be added to the matrix and may increase the content of hydrophobic latanoprost in the matrix. In addition, oils and hydrophobic molecules can be added to the matrix and may increase the solubility of hydrophobic treatment agent in the matrix.

Instead of or in addition to controlling the rate of migration based on the concentration of latanoprost or other intraocular pressure-reducing therapeutic agent(s) dissolved in the matrix, the surface area of the drug core can also be controlled to attain the desired rate of drug migration from the core to the target site. For example, a larger exposed surface area of the core will increase the rate of migration of the treatment agent from the drug core to the target site, and a smaller exposed surface area of the drug core will decrease the rate of migration of the latanoprost or other intraocular pressure-reducing therapeutic agent(s) from the drug core to the target site. The exposed surface area of the drug core can be increased in any number of ways, for example by any of castellation of the exposed surface, a porous surface having exposed channels connected with the tear or tear film, indentation of the exposed surface, protrusion of the exposed surface. The exposed surface can be made porous by the addition of salts that dissolve and leave a porous cavity once the salt dissolves. Hydrogels may also be used, and can swell in size to provide a larger exposed surface area. Such hydrogels can also be made porous to further increase the rate of migration of the latanoprost or other intraocular pressure-reducing therapeutic agent(s).

Further, an implant may be used that includes the ability to release two or more drugs in combination, such as the structure disclosed in U.S. Pat. No. 4,281,654. For example, in the case of glaucoma treatment, it may be desirable to treat a patient with multiple prostaglandins or a prostaglandin and a cholinergic agent or an adrenergic antagonist (beta blocker), such as Alphagan®, or latanoprost and a carbonic anhydrase inhibitor.

In addition, drug impregnated meshes may be used such as those disclosed in U.S. Patent Publication No. 2002/0055701 or layering of biostable polymers as described in U.S. Patent Publication No. 2005/0129731, the disclosures of which are incorporated herein in their entirety. Certain polymer processes may be used to incorporate latanoprost or other intraocular pressure-reducing therapeutic agent(s) into the devices of the present invention; such as so-called "self-delivering drugs" or PolymerDrugs (Polymerix Corporation, Piscataway, N.J.) are designed to degrade only into therapeutically useful compounds and physiologically inert linker molecules, further detailed in U.S. Patent Publication No. 2005/0048121, hereby incorporated by reference in its entirety. Such delivery polymers may be employed in the devices of the present invention to provide a release rate that is equal to the rate of polymer erosion and degradation and is constant throughout the course of therapy. Such delivery polymers may be used as device coatings or in the form of microspheres for a drug depot injectable (such as a reservoir of the present invention). A further polymer delivery technology may also be configured to the devices of the present invention such as that described in U.S. Patent Publication No. 2004/0170685, and technologies available from Medivas (San Diego, Calif.).

In specific embodiments, the drug core matrix comprises a solid material, for example silicone, that encapsulates inclusions of the latanoprost or other intraocular pressure-reducing therapeutic agent(s). The drug comprises molecules which are very insoluble in water and slightly soluble in the encapsulating drug core matrix. The inclusions encapsulated by the drug core can be micro-particles having dimensions from about 1 micrometer to about 100 micrometers across. The drug inclusions can comprise droplets of oil, for example latanoprost oil. The drug inclusions can dissolve into the solid drug core matrix and substantially saturate the drug core matrix with the drug, for example dissolution of latanoprost oil into the solid drug core matrix. The drug dissolved in the drug core matrix is transported, often by diffusion, from the exposed surface of the drug core into the tear film. As the drug core is substantially saturated with the drug, in many embodiments the rate limiting step of drug delivery is transport of the drug from the surface of the drug core matrix exposed to the tear film. As the drug core matrix is substantially saturated with the drug, gradients in drug concentration within the matrix are minimal and do not contribute significantly to the rate of drug delivery. As surface area of the drug core exposed to the tear film is nearly constant, the rate of drug transport from the drug core into the tear film can be substantially constant. Naturally occurring surfactants may affect the solubility of the latanoprost or other intraocular pressure-reducing therapeutic agent(s) in water and molecular weight of the drug can affect transport of the drug from the solid matrix to the tear. In many embodiments, the latanoprost or other intraocular pressure-reducing therapeutic agent(s) is nearly insoluble in water and has a solubility in water of about 0.03% to 0.002% by weight and a molecular weight from about 400 grams/mol. to about 1200 grams/mol.

In many embodiments the latanoprost or other intraocular pressure-reducing therapeutic agent(s) has a very low solubility in water, for example from about 0.03% by weight to about 0.002% by weight, a molecular weight from about 400 grams per mole (g/mol) to about 1200 g/mol, and is readily soluble in an organic solvent. Latanoprost is a liquid oil at room temperature, and has an aqueous solubility of 50 micrograms/mL in water at 25 degrees C., or about 0.005% by weight and a M.W. of 432.6 g/mol.

Naturally occurring surfactants in the tear film, for example surfactant D and phospholipids, may effect transport of the drug dissolved in the solid matrix from the core to the tear film. In some embodiments the drug core can be configured in response to the surfactant in the tear film to provide sustained delivery of latanoprost or other intraocular pressure-reducing therapeutic agent(s) into the tear film at therapeutic levels. For example, empirical data can be generated from a patient population, for example 10 patients whose tears are collected and analyzed for surfactant content. Elution profiles in the collected tears for a drug that is sparingly soluble in water can also be measured and compared with elution profiles in buffer and surfactant such that an in vitro model of tear surfactant is developed. An in vitro solution with surfactant based on this empirical data can be used to adjust the drug core in response to the surfactant of the tear film.

The drug cores may also be modified to utilize carrier vehicles such as nanoparticles or microparticles depending on the size of the molecule to be delivered such as latent-reactive nanofiber compositions for composites and nano-textured surfaces (Innovative Surface Technologies, LLC, St. Paul, Minn.), nanostructured porous silicon, known as BioSilicon®, including micron sized particles, membranes, woven fivers or micromachined implant devices (pSividia, Limited, UK) and protein nanocage systems that target selective cells to deliver a drug (Chimeracore).

In many embodiments, the drug insert comprises of a thin-walled polyimide tube sheath with a drug core comprising latanoprost dispersed in Nusil 6385 (MAF 970), a medical grade solid silicone that serves as the matrix for drug delivery. The distal end of the drug insert is sealed with a cured film of solid Loctite 4305 medical grade adhesive.

The drug insert may be placed within the bore of the punctal implant, the Loctite 4305 adhesive does not come into contact with either tissue or the tear film. The inner diameter of the drug insert can be 0.32 mm; and the length can be 0.95 mm. At least four latanoprost concentrations in the finished drug product can be employed: Drug cores can comprise 3.5, 7, 14 or 21 micrograms latanoprost, with percent by weight concentrations of 5, 10, 20, or 30% respectively. Assuming an overall elution rate of approximately 100 ng/day, the drug core comprising 14 micrograms of latanoprost is configured to deliver drug for approximately at least 100 days, for example 120 days. The overall weight of the drug core, including latanoprost or other intraocular pressure-reducing therapeutic agent(s), can be about 70 micrograms. The weight of the drug insert including the polyimide sleeve can be approximately 100 micrograms. In an embodiment, the drug core can comprise 46 micrograms of latanoprost, and in another embodiment, the drug core can comprise 95 micrograms of latanoprost.

In many embodiments, the drug core may elute with an initial elevated level of latanoprost or other intraocular pressure-reducing therapeutic agent(s) followed by substantially constant elution of the latanoprost or other intraocular pressure-reducing therapeutic agent(s). In many instances, an amount of latanoprost or other intraocular pressure-reducing therapeutic agent(s) released daily from the core may be below the therapeutic levels and still provide a benefit to the patient. An elevated level of eluted latanoprost or other intraocular pressure-reducing therapeutic agent(s) can result in a residual amount of latanoprost or other intraocular pressure-reducing therapeutic agent(s) or residual effect of the latanoprost or other intraocular pressure-reducing therapeutic agent(s) that is combined with a sub-therapeutic amount of latanoprost or other intraocular pressure-reducing therapeutic agent(s) to provide relief to the patient. In embodiments where therapeutic level is about 80 ng per day, the device may deliver about 100 ng per day for an initial delivery period. The extra 20 ng delivered per day can have a beneficial effect when latanoprost or other intraocular pressure-reducing therapeutic agent(s) is released at levels below the therapeutic level, for example at 60 ng per day. As the amount of drug delivered can be precisely controlled, an initial elevated dose may not result in complications or adverse events to the patient.

In certain embodiments, the methods of the invention result in a percentage reduction in intraocular pressure of approximately 24% from baseline. In some embodiments, the methods of the invention results in a percentage reduction or decrease in intraocular pressure of approximately 23%, approximately 22%, approximately 21%, or approximately 20% from baseline. In certain embodiments, the methods of the invention result in a percentage reduction or decrease in intraocular pressure of at least 24%, at least 23%, at least 22%, at least 21%, at least 20%, at least 15%, or at least 10% from baseline.

In certain embodiments, the methods of the invention result in a reduction in intraocular pressure from baseline over a treatment period of about 2 mm Hg, about 3 mm Hg, about 4, mm Hg, about 5 mm Hg, about 6 mm Hg, or about 7 mm Hg. In certain embodiments, the methods of the invention result in a reduction in intraocular pressure from baseline of at least 2 mm Hg, at least 3 mm Hg, at least 4 mm Hg, at least 5 mm Hg, at least 6 mm Hg, or at least 7 mm Hg. In some embodiments, intraocular pressure is reduced to less than or equal to 24 mm Hg, less than or equal to 23 mm Hg, less than or equal to 22 mm Hg, less than or equal to 21 mm Hg, less than or equal to 20 mm Hg, less than or equal to 19 mm Hg, less than or equal to 18 mm Hg, or less than or equal to 17 mm Hg, or less than or equal to 16 mm Hg, less than or equal to 15 mm Hg, less than or equal to 14 mm Hg, or less than or equal to 13 mm Hg.

In an embodiment, the implants and methods of the invention provide a 90-day course of treatment. In other embodiments, the implants and methods of the invention provide a 60-day course of treatment. In still other embodiments, the implants and methods of the invention provide a 45-day course of treatment. In still other embodiments, the implants and methods of the invention provide a 30-day course of treatment, depending upon the disease to be treated and the therapeutic agent to be delivered. Other embodiments include one week, two weeks, three weeks, four weeks, five weeks, six weeks, seven weeks, eight weeks, nine weeks, ten weeks, eleven weeks, or twelve weeks of treatment. In some embodiments, effective levels of latanoprost or other intraocular pressure-reducing therapeutic agent(s) release during the entire course of treatment. In a further embodiment, the variability in intraocular pressure over the course of treatment is less than about 1 mm Hg. In other embodiments, the variability in intraocular pressure over the course of treatment is less than about 2 mm Hg. In other embodiments, the variability in intraocular pressure over the course of treatment is less than about 3 mm Hg.

The implants described herein may be inserted into the superior punctum, the inferior punctum, or both, and may be inserted into one or both eyes of the subject.

Embodiments of the invention can be described by the following non-limiting examples.

Patient Noncompliance

Numerous studies have been published showing high noncompliance by patients using eye drops for treatment of various ocular disorders. One study showed only 64% of patients used the eye drops as directed (Winfield A J, et al. A study of the causes of non-compliance by patients prescribed eyedrops. Br J Ophthalmol. 1990 August; 74(8):477-80). Another study showed that 41% of patients using eye drops for glaucoma missed six or more doses over a 30-day period (Norell S E, Granstrom P A. Self-medication with pilocarpine among outpatients in a glaucoma clinic. *Br J Ophthalmol*. 1980 February; 64(2):137-41).

In an exemplary embodiment, the invention described herein provides methods to treat glaucoma that avoid the problem of noncompliance associated with eye drop administration. In some embodiments, the methods of the invention reduce patient noncompliance significantly compared to eye drop administration, e.g., by at least about 10%, at least about 20%, at least about 30%, at least about 40%, at least about 50%, at least about 60%, at least about 70%, at least about 80%, or at least about 90%. In some embodiments, overall patient noncompliance with the methods described herein is about 5%, about 10%, about 15%, about 20%, or about 25%.

Patient noncompliance may occur if an implant of the invention is intentionally removed by a patient or if the patient does not seek reinsertion of the implant after such implant has been unintentionally lost from the punctum of the patient. Patient compliance is considered to be met if the implant is intentionally removed and the patient seeks reinsertion within less than about 48 hours. Patient compliance is also considered to be met if the implant is intentionally removed and the patient seeks reinsertion within less than about 24 hours of removal or loss of the implant.

Methods of Treatment

In various embodiments, the invention described herein provides methods to treat glaucoma, elevated intraocular pressure, and glaucoma-associated elevated intraocular pressure with a therapeutic agent. Examples of glaucoma treatable according to the present invention include primary open angle glaucoma, normal intraocular tension glaucoma, hypersecretion glaucoma, ocular hypertension, acute angle-closure glaucoma, chronic closed angle glaucoma, combined-mechanism glaucoma, corticosteroid glaucoma, amyloid glaucoma, neovascular glaucoma, malignant glaucoma, capsular glaucoma, plateau iris syndrome and the like.

In one embodiment, the invention provides a method of treating glaucoma and/or ocular hypertension with a punctal plug delivering a therapeutic agent effective against these conditions in a sustained release manner. The release occurs at a rate and in an amount sufficient to be therapeutically useful. In various embodiments, the therapeutic agent is a prostaglandin, e.g., latanoprost.

In an exemplary embodiment, the condition treated is primary open-angle glaucoma (POAG) and ocular hypertension (OH) with punctual plug of the invention in which a sustained release formulation of a prostaglandin derivative is provided. In this method one to four punctual plugs may be inserted per patient. Exemplary punctal plugs are formulated with from about 40 µg to about 115 µg of prostaglandin. In various embodiments, the prostaglandin is latanoprost. In various embodiments, the plugs are formulated with either 46 µg or 95 µg of latanoprost so that a dosage which is a member selected from 46 µg, 92 µg, 95 µg, 141 µg or 190 µg is administered to each eye. In one embodiment 141 µg of latanoprost was administered to an individual eye. In another embodiment, 190 µg of latanoprost was administered to an individual eye. A patient may have the same amount of latanoprost administered to each eye or the patient may have a different amount administered to each eye.

In some embodiments, the therapeutic agent is released to the eye over a sustained period of time. In an embodiment, the sustained period of time is at least about 14 days, about 21 days, about 28 days, about 45 days, about 60 days or at least about 90 days. In some embodiments, the method comprises inserting through a punctum an implant having a body and a drug core so that the drug core is retained near the punctum. In some embodiments, the method comprises inserting through a punctum an implant having a body dispersed throughout with a therapeutic agent. In some embodiments, an exposed surface of the drug core or agent dispersed body located near the proximal end of the implant contacts the tear or tear film fluid and the latanoprost or other intraocular pressure-reducing therapeutic agent(s) migrates from the exposed surface to the eye over a sustained period of time while the drug core and body is at least partially retained within the punctum. In an exemplary embodiment, a method of treating an eye with latanoprost or other intraocular pressure-reducing therapeutic agent(s) is provided, the method comprising inserting through a punctum into a canalicular lumen an implant having an optional retention structure so that the implant body is anchored to a wall of the lumen by the retention structure. The implant releases effective amounts of latanoprost or other intraocular pressure-reducing therapeutic agent(s) from a drug core or other agent supply into a tear or tear film fluid of the eye. In some embodiments, the drug core may be removed from the retention structure while the retention structure remains anchored within the lumen. A replacement drug core can then be attached to the retention structure while the retention structure remains anchored. At least one exposed surface of the replacement drug core releases latanoprost or other intraocular pressure-reducing therapeutic agent(s) at therapeutic levels over a sustained period.

A replacement implant, or in other embodiments, a replacement drug core which can in some embodiments be attached to or include its own retention structure, can be attached to the retention structure approximately every 30 days, approximately every 60 days or approximately every 90 days to result in continuous release of the drug to the eye for a period of time of approximately 180 days, approximately 270 days, approximately 360 days, approximately 450 days, approximately 540 days, approximately 630 days, approximately 720 days, approximately 810 days or approximately 900 days. In some embodiments, a replacement implant can be inserted into the punctum approximately every 30 days, approximately every 60 days or approximately every 90 days to achieve release of the drug to the eye for extended periods of time, including up to about 180 days, about 270 days, about 360 days, about 450 days, about 540 days, about 630 days, about 720 days, about 810 days or about 900 days.

In other embodiments, a method for treating an eye with latanoprost or other intraocular pressure-reducing therapeutic agent(s) is provided, the method comprising inserting a drug core or other implant body at least partially into at least one punctum of the eye. The drug core may or may not be associated with a separate implant body structure. The drug core or agent-impregnated implant body provides sustained release delivery of latanoprost or other intraocular pressure-reducing therapeutic agent(s) at therapeutic levels. In some embodiments, the sustained release delivery of latanoprost or other intraocular pressure-reducing therapeutic agent(s) continues for up to 90 days.

In exemplary embodiments, a method for treating an eye with latanoprost or other intraocular pressure-reducing therapeutic agent(s) is provided, the method comprising inserting a distal end of an implant into at least one punctum and into at least one lacrimal canaliculus of the eye. In some embodiment, a retention structure of the implant is fitted so as to inhibit expulsion of the implant. The expansion of the retention structure can help to occlude a flow of tear fluid through the punctum. In some embodiments, the implant is configured such that, when implanted, an at least 45 degree angled intersection exists between a first axis, defined by a proximal end of the implant, and a second axis, defined by the distal end of the implant, to inhibit expulsion of the implant. Latanoprost or other intraocular pressure-reducing therapeutic agent(s) is delivered from a proximal end of the implant to the tear fluid adjacent the eye. Delivery of the latanoprost or other intraocular pressure-reducing therapeutic agent(s) is inhibited distally of the proximal end.

The methods of the invention provide sustained release of latanoprost or other intraocular pressure-reducing therapeutic agent(s). In some embodiments, the active agent is released from the implant for at least one week, at least two weeks, at least three weeks, at least four weeks, at least five weeks, at least six weeks, at least seven weeks, at least eight weeks, at least nine weeks, at least ten weeks, at least eleven weeks, at least twelve weeks, at least thirteen weeks, at least fourteen weeks, at least fifteen weeks, or at least sixteen weeks. In some embodiments, the active agent is latanoprost. In an embodiment, the latanoprost or other intraocular pressure-reducing therapeutic agent(s) is released for at least twelve weeks. In an exemplary embodiment, the methods of treatment according to the present invention comprises an adjunctive therapy with a latanoprost-delivering eye drop solution, for example, Xalatan®.

The amount of latanoprost or other intraocular pressure-reducing therapeutic agent(s) associated with the implant may vary depending on the desired therapeutic benefit and the time during which the device is intended to deliver the therapy. Since the devices of the present invention present a variety of shapes, sizes and delivery mechanisms, the amount of drug associated with the device will depend on the particular disease or condition to be treated, and the dosage and duration that is desired to achieve the therapeutic effect. Generally, the amount of latanoprost or other intraocular pressure-reducing therapeutic agent(s) is at least the amount of drug that, upon release from the device, is effective to achieve the desired physiological or pharmacological local or systemic effects.

Certain embodiments of the implants of the present invention can be configured to provide, in combination with each other or separately, delivery of latanoprost or other intraocular pressure-reducing therapeutic agent(s) at daily rates that are greater than or equivalent to the therapeutically effective drop form of treatment. Other embodiments of the implants of the present invention can be configured to provide, in combination with each other or separately, delivery of latanoprost or other intraocular pressure-reducing therapeutic agent(s) at daily rates that enable comparable clinical outcomes to that of daily administered eye drops. Other embodiments of the implants of the present invention can be configured to provide delivery of latanoprost or other intraocular pressure-reducing therapeutic agent(s) at daily rates that exceed the therapeutically effective drop form of treatment.

For comparison purposes, standard treatment, i.e., the recommended daily total dose, with drops, such as Xalatan® drops, delivers about 1.5 micrograms of latanoprost to the eye all at once, assuming a 35 microliter drop volume. In embodiments of the present invention, the sustained release of at least 1.5 micrograms of latanoprost per day can be administered. For example, in an embodiment, a sustained release ophthalmic drug delivery system is configured to release, on a sustained basis over the course of 24 hours to the eye, a total amount of latanoprost from a combination of a first lacrimal implant, located in a lower punctum of the eye, and a second lacrimal implant, located in an upper punctum of the same eye, that is greater than or equal to the recommended daily total dose of latanoprost that is in Xalatan® drops (i.e., eye drop form). In other embodiments, at least two times the recommended daily total dose of latanoprost that is in Xalatan® drops may be release by a combination of the first lacrimal implant and the second lacrimal implant that are in the lower punctum and the upper punctum, respectively, of the same eye. In an embodiment, both eyes of the patient may be treated with two lacrimal implants at the same time.

Methods of inserting and removing the implant are known to those of skill in the art. For instance, tools for insertion and removal/extraction of implants are described in U.S. Patent Application No. 60/970,840 (filed Sep. 7, 2007 and entitled Insertion and Extraction Tools for Punctal Implants), the disclosure of which is incorporated herein in its entirety. Generally, for placement, the size of a punctal implant to be used may be determined by using suitable magnification or, if provided, using a sizing tool that accompanies the punctal implant. The patient's punctum may be dilated if necessary to fit the punctal implant. A drop of lubricant may be applied if necessary to facilitate placement of the implant into the punctum. Using an appropriate placement instrument, the implant may be inserted into the superior or inferior punctum of the eye. After placement, the cap of the implant may be visible. This process may be repeated for the patient's other eye. For removal of the implant, small surgical forceps may be used to securely grasp the implant at the tube section below the cap. Using a gentle tugging motion the implant may be gently retrieved.

Kits

The present invention also provides methods that utilize kits that, in an exemplary embodiment, include one, two, three or four implants of use in the methods of the invention. In an exemplary embodiment, the implants are sterilized. In various embodiments, there is also provided an insertion tool. An exemplary insertion tool of use in this embodiment is set forth herein. In various embodiments, at least one implant is engaged with the insertion tool by engaging the pin of the tool (760) with the bore of the implant (385). In various embodiments, the tool is sterilized. In an exemplary embodiment, the elements of the kit are packaged together with one or more of a set of instructions for installing the implant in the punctum, a topical anesthetic, an administration device for the topical anesthetic or another component of use in installing the implant in the punctum.

The following Examples are provided to illustrate exemplary embodiments of the invention and are not to be construed as limiting the scope of the present invention.

EXAMPLES

Example 1—Evaluation of Safety and Efficacy of the Latanoprost Punctal Plug Delivery System (L-PPDS) Containing Latanoprost A Phase II, open-label, clinical study was conducted in human subjects with ocular hypertension (OH) or open-angle glaucoma (OAG) to evaluate safety and efficacy of the latanoprost punctal plug delivery system (L-PPDS).

The Phase II trial featured simultaneous placement of punctal plugs in both the upper and lower puncta for delivery of a daily drug load with a goal of enabling comparable clinical outcomes to that of daily administered Xalatan® eyedrops. The overall objective was a mean reduction in IOP of 5 mm Hg or greater. The primary endpoint in this Phase II study was a mean change in IOP from baseline (measured as mm Hg) at 2 weeks. Secondary endpoints were the mean change in IOP from baseline at 4 weeks and mean percentage change in IOP at 2 weeks and 4 weeks. A total of 95 ITT (Intent to Treat) subjects were included in the L-PPDS treatments in this study. The mean IOP as baseline was 25.8 mm HG for this group (with a range of baseline of 22.5 mm Hg to 33 mm Hg).

After 2 weeks of L-PPDS treatment, IOP showed a statistically significant mean change from baseline of −6.2 mm Hg (95% C.I. −6.8, −5.6). At the end of week 2, 73% of subjects showed an IOP reduction vs. baseline of 5 mm Hg or greater and 51% of subjects showed a reduction of 6 mm Hg or greater. The mean percentage change in IOP from baseline at 2 weeks was −24.3%, which was statistically significant (95% C.I. −26.7, −21.9).

After 4 weeks of L-PPDS treatment, IOP showed a statistically significant mean change from baseline of −5.7 mm Hg (95% C.I. −6.5, −4.9). At the end of 4 weeks, 60% of subjects showed an IOP reduction vs. baseline of 5 mm Hg or greater and 47% of subjects showed a reduction of 6 mm Hg or greater. The mean percentage change in IOP from baseline at 4 weeks was also statistically significant at 22.3% (95% C.I. −25.4, −19.2).

Subjects were fitted with L-PPDS containing specified latanoprost concentrations in the upper L-PPDS (46 μg) and the lower L-PPDS (95 μg).

Study Procedures

During the screening visit, the subjects were fitted with the trial punctal plugs for approximately 15 minutes to 2 hours to assess fitting and eligibility. Pre-washout IOP measurements were determined in each eye of the patient, and adverse device events (ADEs) were also monitored. After the trial fitting, subjects began the washout period in which subjects were discontinued from topical prostaglandin therapy to assess IOP eligibility for a minimum of 4 weeks and to a maximum of 6 weeks.

After the washout, baseline IOP was measured in each eye of a patient on two separate visits that were 2 to 4 days apart (Day −2 and Day 0 study visits), after the patient had washed out of previous topical prostaglandin therapy.

At the start of the study (Day 0), each patient had an L-PPDS inserted bilaterally into each puncta of each eyes and inspected thereafter at each visit. If an L-PPDS was spontaneously extruded, one replacement L-PPDS per patient was allowed. The L-PPDS were removed at the Week 4 visit.

After placement of the L-PPDS, subjects were monitored for any treatment-emergent or adverse events (Aes) during the 4-week treatment period. Subjects had weekly follow-up visits with the last study visit at Week 4. Tear volume was measured by a Schirmer test with anesthesia over 5 minutes at Day 0 and at the last visit. Visual acuity was measured with best correction using a Snellen chart at every visit. Biomicroscopy examinations were performed in each eye at every visit, including an inspection of the L-PPDS placement. Treatment-emergent ocular and systemic Aes and concomitant medications were monitored at every visit with standardized questioning techniques. Automated perimetry was performed to measure visual fields at the last visit. A funduscopy examination was performed at the last visit.

Goldmann IOP measurements (the average of 3 measurements) were measured in each eye at every visit. The baseline IOP was taken on two separate days, at least 48 hours apart. Specifically, IOP measurements were taken at 8:30 am (±30 minutes) at each visit.

L-PPDS

Each L-PPDS for the upper puncta was of a proprietary punctal plug design and had a latanoprost strength of 46 μg. Inactive components were medical grade silicone, polyimide tubing, DMPC, cyanoacrylate medical grade adhesive, and 2% green colorant. Each L-PPDS was supplied in a separate sterilized mylar foil pouch.

Each L-PPDS for the lower puncta was of a proprietary punctal plug design and had a latanoprost strength of 95 μg. Inactive components are medical grade silicone, polyimide tubing, DMPC, cyanoacrylate medical grade adhesive, and 2% green colorant. L-PPDS for the lower puncta were preloaded on an insertion tool. Each L-PPDS and insertion tool were supplied in a tray contained in a sterilized mylar foil pouch.

Figure 13:
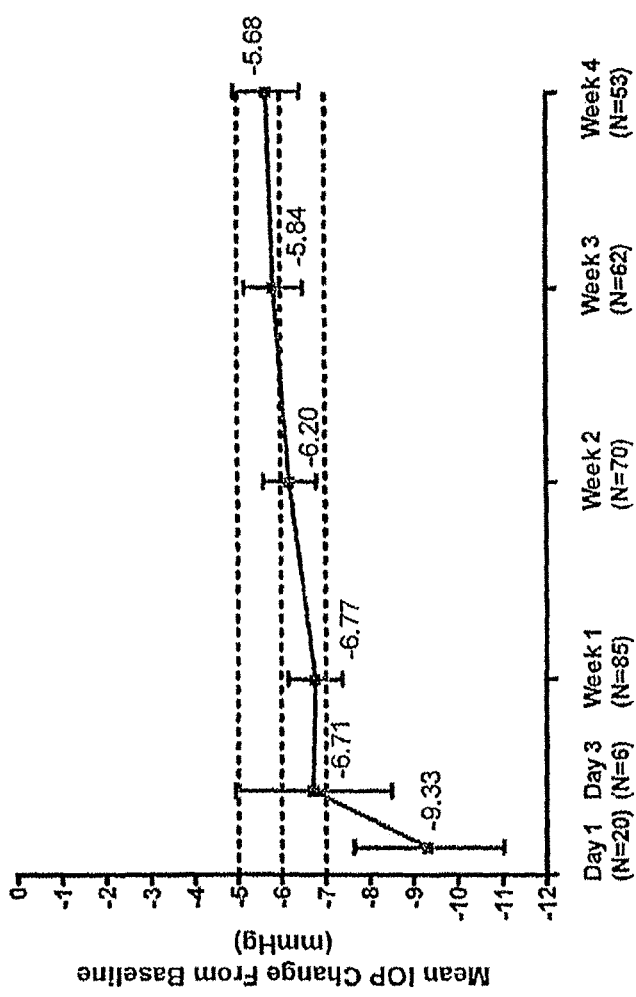
FIG. 13 illustrates mean intraocular pressure (IOP) change from baseline during treatment with a sustained release ophthalmic drug delivery system according to an embodiment of the present invention over a four-week period.
Figure 14:
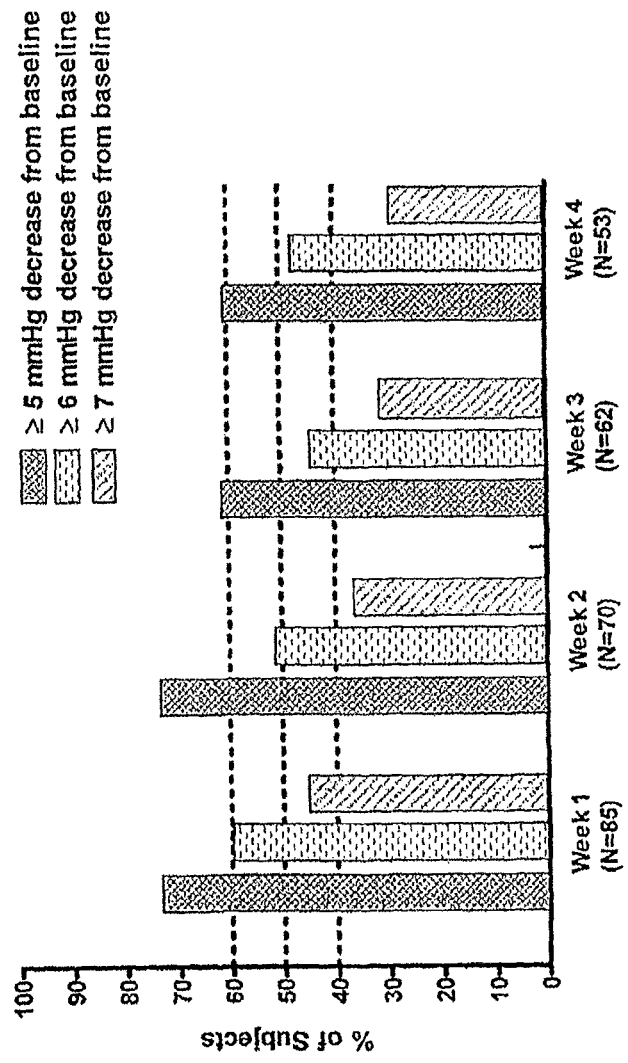
FIG. 14 illustrates percentage of subjects achieving categorical absolute intraocular pressure (IOP) reduction from baseline during treatment with the sustained release ophthalmic drug delivery system according to an embodiment of the present invention over the four-week period.

FIG. 13 shows the mean reduction in intraocular pressure (IOP) from baseline in weeks during the treatment period. FIG. 14 shows the percent of subjects that recorded an IOP reduction of ≥5 mm Hg from baseline, ≥6 mm Hg from baseline, and ≥7 mm Hg from baseline, in weeks.

Figure 15:
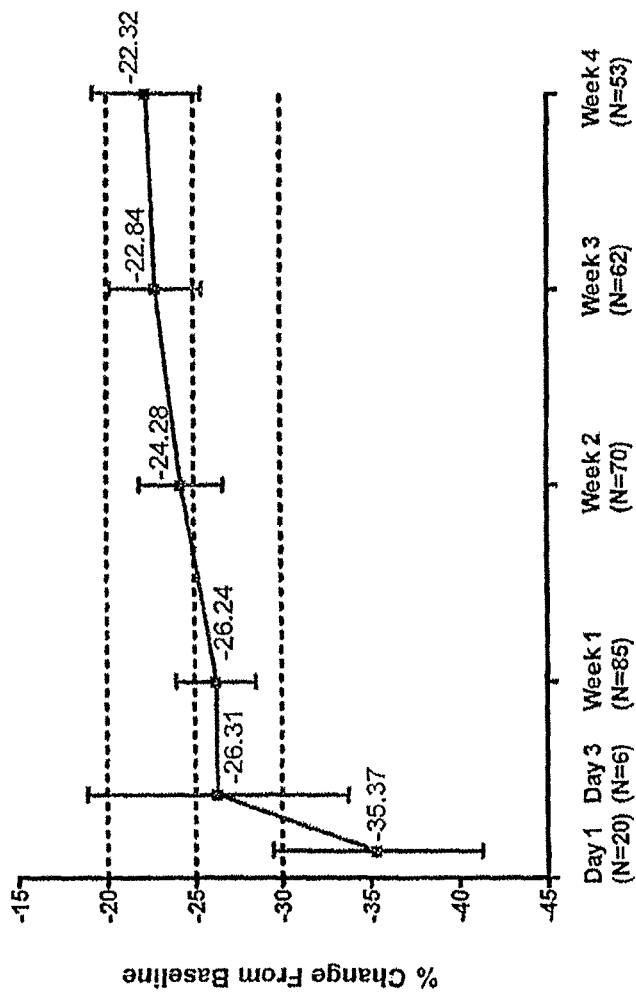
FIG. 15 illustrates percent change in IOP from baseline during treatment with a sustained release ophthalmic drug delivery system according to an embodiment of the present invention over a four-week period.

A secondary endpoint in the study was the percentage change in average IOP from baseline at 2 weeks and 4 weeks for L-PPDS treatment. FIG. 15 shows the mean reduction in IOP from baseline in weeks during the treatment period. At 2 weeks, the percentage change from baseline of −24.3% (95% C.I. −26.7, −21.9) was statistically significant, and at 4 weeks, the percentage change from baseline of −22.3% (95% C.I. −25.4, −19.2) was also statistically significant.

The IOP reduction results are summarized in the Table 2:

TABLE 2

Mean change and % change in IOP in weeks for L-PPDS containing latanoprost concentration of 141 μg

| | Mean Change in IOP from Baseline (95% C.I.) | % Change in IOP from Baseline (95% C.I.) |
|---|---|---|
| 2 weeks (n = 70) | −6.2 (−6.8, −5.6) | −24.3% (−26.7%, −21.9%) |
| 4 weeks (n = 53) | −5.7 (−6.5, −4.9) | −22.3% (−25.4%, −19.2%) |

Plug Retention Results

The lower punctal plug achieved 94% or greater retention per subject across the duration of the 4 week study. The upper punctal plug showed a retention rate of 40% per subject across the duration of the study.

Assessment of Treatment Safety and Tolerability

The L-PPDS was well tolerated over the testing period. The majority of AEs were ocular in nature, however, none were serious AEs. The most frequently reported AE was mild to moderate tearing. Few subjects experienced any discomfort related to the punctal plugs with most subjects having either no awareness or mild awareness of the punctal plugs by week 4.

Example 2—Comparison of Clinical Studies of the L-PPDS at Different Dosages

A number of clinical studies have been conducted to assess the safety, efficacy, and dosing for L-PPDS treatment in more than 300 human subjects with OH or OAG. These studies have investigated the preliminary safety and efficacy of L-PPDS over the dose range of 3.5 to 95 μg per eye, primarily delivered via an L-PPDS positioned in the lower puncta. See, for example, *ClinicalTrials.gov Identifier*: NCT00967811, "An Open-Label, Phase 2 Study of Different Formulations (E1 and E2) of the Latanoprost Punctal Plug Delivery System (L-PPDS) in Subjects With Ocular Hypertension (OH) or Open-Angle Glaucoma (OAG)," Study Start Date: August 2009, (other study ID number: PPL GLAU 07), incorporated herein by reference; and *ClinicalTrials.gov Identifier*: NCT01037036, "An Open-Label, Phase 2 Study of the Latanoprost Punctal Plug Delivery System (L-PPDS) With Adjunctive Xalatan® Eye Drops in Subjects With Ocular Hypertension (OH) or Open-Angle Glaucoma (OAG)," Study Start Date: Dec. 17, 2009, (other study ID number: PPL GLAU 08), incorporated herein by reference. Based on the published clinical results for IOP reduction associated with Xalatan® eye drops, the magnitude of mean IOP reductions has been less than expected; however, results for L-PPDS show that some subjects had IOP reductions that would be expected with Xalatan®. All studies have occluded only one punctum per eye. The overall mean IOP reduction for the L-PPDS was similar among most of the studies (range −3 to −5 mmHg), regardless of latanoprost concentration from 3.5 μg to 95 μg per eye. Specifically, the mean IOP reduction according to the clinical study described in Example 1 and the clinical studies of the L-PPDS containing latanoprost concentrations of 44 μg and 81 μg, see *ClinicalTrials.gov Identifier*: NCT00820300, "An Open-Label, Phase 2 Study of the Latanoprost Punctal Plug Delivery System (L-PPDS) in Subjects With Ocular Hypertension (OH) or Open Angle Glaucoma (OAG)," Study Start Date: January 2009, (other study ID number: PPL GLAU 03), incorporated herein by reference, and two different 95 µg formulations were compared, where the two 95 µg formulations (E1 and E2) were developed to deliver different average daily doses, see *ClinicalTrials.gov Identifier*: NCT00967811, "An Open-Label, Phase 2 Study of Different Formulations (E1 and E2) of the Latanoprost Punctal Plug Delivery System (L-PPDS) in Subjects With Ocular Hypertension (OH) or Open-Angle Glaucoma (OAG)," Study Start Date: August 2009, (other study ID number: PPL GLAU 07), incorporated herein by reference. Table 3 summarizes the range of mean IOP change from baseline during the first 4 weeks period of the L-PPDS treatments in the clinical studies. Table 4 summarizes the IOP change (mm Hg) in number (percent) of subjects in weeks 2 and 4.

TABLE 3

Mean IOP change from baseline in clinical studies

| | Study ID | | | | |
|---|---|---|---|---|---|
| | GLAU 03 | | GLAU 07 | | GLAU 11 (Example 1) |
| L-PPDS Formulation | 44 µg (N = 57) | 81 µg (N = 53) | 95 µg E1 (N = 42) | 95 µg E2 (N = 41) | 141 µg (N = 95) |
| Range of Mean IOP Change from Baseline: Weeks 1 to 4 (mmHg) | −3.5 to −3.6 | −3.0 to −3.4 | −3.5 to −4.2 | −3.9 to −4.7 | −5.7 to −6.8 |

TABLE 4

IOP Changes in % Subjects

| | | Study ID | | | | |
|---|---|---|---|---|---|---|
| | | GLAU 03 | | GLAU 07 | | GLAU 11 |
| | | L-PPDS Formulation | | | | |
| | | 44 µg (N = 57) | 81 µg (N = 53) | 95 µg E1 (N = 42) | 95 µg E2 (N = 41) | 141 µg (N = 95) |
| Week 2 | ≥5 | 31% | 25% | 31% | 22% | 73% |
| | ≥6 | 24% | 16% | 17% | 17% | 51% |
| | ≥7 | 16% | 4% | 12% | 15% | 36% |
| Week 4 | ≥5 | 35% | 29% | 38% | 31% | 60% |
| | ≥6 | 23% | 22% | 15% | 21% | 47% |
| | ≥7 | 8% | 12% | 13% | 10% | 28% |

No mean IOP change of ≥5 mm Hg was observed within the 4 weeks duration of treatments of L-PPDS containing latanoprost concentrations of 44 µg, 81 µg, and 95 µg. The mean IOP reductions were significantly greater with L-PPDS containing a combined latanoprost concentration of 141 µg recorded in the clinical study described in Example 1, compared with L-PPDS containing lower lantanoprost doses. The mean IOP change from baseline for L-PPDS with a combined latanoprost concentration of 141 µg was substantial, from −5.7 mm Hg to −6.8 mm Hg.

Example 3—Method of Preparation L-PPDS (95 µg) Cores

NuSil Silicone MED6385 part A was stirred for a minimum of 5 minutes, and 63 mg of which was weighed and transferred onto a glass slide. To the same glass slide was added Latanoprost (obtained from Everlight Chemical, Taipei, Taiwan) (48 mg), dimyristoylphosphatidylcholine (DMPC) (9 mg) and NuSil Med6382 crosslinker (2.4 mL). Using a 0.5 µL Hamilton Syringe, Nusil MED6385 part B (0.348 µL) was transferred directly onto a mini spatula. The latanoprost, NuSil MED6382 crosslinker, NuSil Silicone MED-6385 part B and DMPC were mixed together for 2-5 minutes to form a homogenous mixture. The resulting mixture was combined with NuSil Silicone MED6385 part A and was mixed for another 2 minutes to form a homogenous mixture, which was immediately transferred into a previously prepared syringe assembly. The syringe was then attached to polyimide tubing (0.024" OD) by way of an adapter. The polyimide tubing was kept at a temperature of 4° C. by way of a cooling jacket. After 2 minutes, the mixture was injected into the polyimide tubing by increasing the pressure of the system to 40 psi over 2.5 minutes. Once the mixture had extruded through the polyimide tubing to the end, the tubing was cut and both ends were clamped. The tube was placed into a humidity chamber at 40° C. and 80% relative humidity for 24-96 hours to cure the silicone, and the tubing was cut into 1.0 mm lengths. Loctite 4305 (Henkel Adhesives Technologies, Ltd.) was applied to the bottom end of the cut tubing and cured for 20 seconds in a 100 W UV curing chamber. These cores were then inserted into the cavity of punctal plugs with the glued end positioned in the bottom of the cavity.

Example 4—PP DEV 05: A Device Evaluation Study to Further Assess the Physical and Clinical Characteristics of Prototype Punctal Plug Design Iterations Study Objective To evaluate the physical and clinical performance characteristics of punctal plug design iterations.

Study Design

This is a multicenter, device assessment, feasibility study to assess the physical and clinical performance characteristics of prototype punctal plugs. Up to approximately 500 subjects will be enrolled at 5-15 sites in the US. No drug treatment will be administered. The study will evaluate the physical (handling) and clinical (comfort, tearing, retention) characteristics of punctal plug prototypes. The study will be iterative, with data monitored on an ongoing basis and design modifications to the punctal plugs made if further improvements are indicated. An investigational plug detection aid may also be evaluated.

Subjects will be enrolled into 1 of 2 groups. Group 1 will undergo two 12-week plug placement periods. Group 2 will undergo two 2-week plug placement periods followed by one 12-week plug placement period. Plug placement will be attempted in the lower and upper puncta of both eyes. Placement must be successful in both the upper and lower puncta of at least 1 eye for the subject to be eligible for the study. The Sponsor will inform the sites in advance in writing which plug iterations to use for each subject for each placement period. For Group 1, study visits will occur at Day 0, and Weeks 4, 8, 12, 16, 20 and 24, with plug placement at the Day 0 and Week 12 visits. For Group 2, study visits will occur at Day 0 and Weeks 1, 2, 3, 4, 8, 12 and 16, with plug placement at Day 0, Week 2, and Week 4.

A subject who completes or is withdrawn from the Group 1 or Group 2 treatment schedule may be re-enrolled into the study (to either Group 1 or Group 2). A re-enrolled subject will be assigned a new subject number and undergo screening procedures again.

Safety will be assessed throughout the study.

Study Population

Subjects will be male and female volunteers, age 50 years or older. Main exclusion criteria will include:
History of, or active, lid disease requiring lid scrubs (ie, moderate or severe blepharitis, dacryocystitis, meibomianitis)
Structural lid abnormalities (ie, ectropion, entropion)
Active anterior segment inflammatory disease
Ocular allergies
Habitual eye rubbing
Previous intolerance of punctal plugs (ie, inflammatory reaction, granuloma, dacryocystitis, etc. due to punctal plug wear)
Laser eye surgery within the last 3 months or incisional eye surgery within the last 6 months.

Study Devices

The punctal plugs will be placed bilaterally into the upper and lower puncta using an investigational insertion tool provided with the plug or ophthalmic forceps. The techniques for insertion and removal are similar to the procedures for other commercial punctal plugs.

Study Variables
Device Performance:
Retention rates
Insertion success
Ease of use
Tolerability
Comfort
Tearing
Safety
Adverse device events (ADEs)
Biomicroscopy
Study Procedures and Assessments:
Device Performance:
For subjects who provide additional consent, photographs of the punctal plugs may be taken after their placement to observe their location in the lid margin; videography of punctal plug placement and removal procedures may be performed for future physician training. In-person observational physician training of punctal plug placement and removal procedures may also occur.
Tolerability:
Subjects will rate the acceptability of tearing and comfort according to a visual analog scale at every visit.
Safety:
Biomicroscopy will be performed in each eye and ADEs will be collected at every study visit.
Sample Size and Statistical Analyses:
The sample size is based on clinical judgment and is believed to be sufficient to meet the study objectives. All study variables will be summarized descriptively. ADEs will be coded using the Medical Dictionary for Regulatory Activities (MedDRA) and summarized descriptively by system organ class and preferred term.

Example 5—Clinical Study of Punctal Plug Retention

Retention Study

Figure 10A:
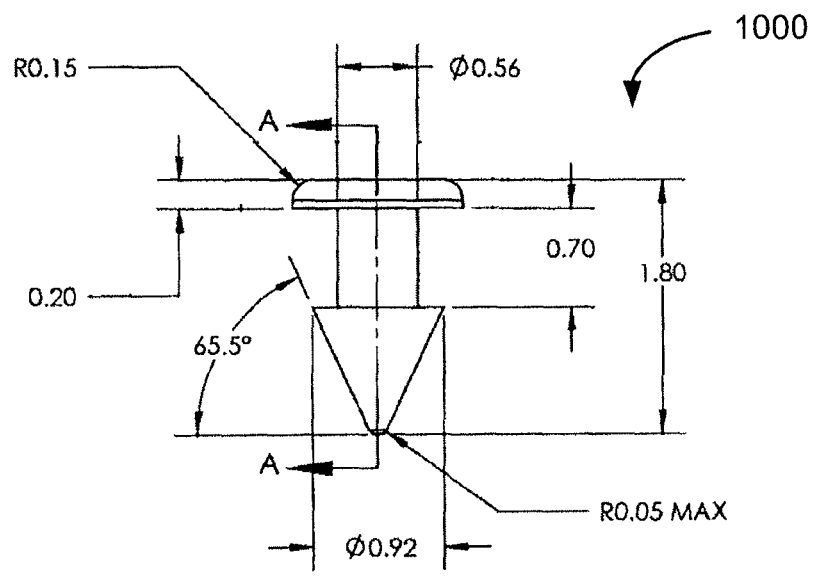
FIG. 10A illustrates a side view of a commercial implant used for the comparison studies herein.
Figure 10B:
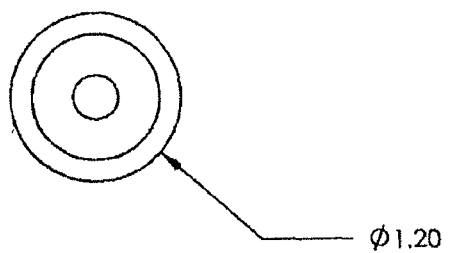
FIG. 10B illustrates a top view of the commercial implant used for the comparison studies herein.
Figure 10C:
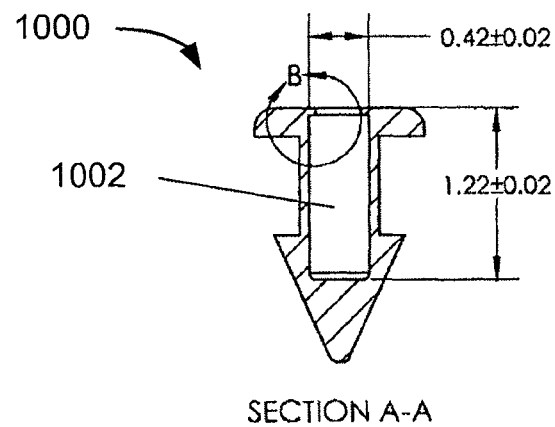
FIG. 10C is a cross-sectional view taken about line A-A of FIG. 10A illustrating a modified cavity formed in the commercial implant for the comparison studies herein.
Figure 10D:
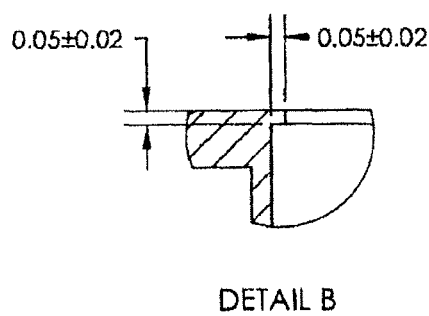
FIG. 10D is a partially enlarged view taken about circle B of FIG. 10C illustrating a lip at an opening of the modified cavity in the commercial implant for the comparison studies herein.

A clinical study was conducted to evaluate exemplary embodiments of the present invention in comparison with a modified commercial implant. The commercial implant 1000 is illustrated in FIGS. 10A and 10B, where a side view and a top view are depicted respectively along with corresponding major dimensions. The commercial implant 1000 has no cavity. For the purpose of comparison study, the commercial implant 1000 is modified by constructing a cavity 1002 in the implant 1000, as shown in FIGS. 10C and 10D. The cavity 1002 is configured such that it has essentially the same shape and the same size as of the cavity 458 in the exemplary embodiments of the present application selected for the comparison study.

The comparison study involves ninety six subjects, baseline demographics of which are provided in FIG. 11. Each subject is fitted with two modified commercial implants indicated and two selected exemplary embodiments of the present applications. The modified commercial implants are referred as upper implants and the selected exemplary embodiments of the present applications as lower implants. The upper implant contains 46 ug of latanoprost and the lower implant contains 95 ug of latanoprost for a total dose of 141 µg of total latanoprotst. The 141 µg of total latanoprotst drug is consistent with three months of Xalatan drops.

The study was conducted over four weeks. During the study, the subjects were examined and the intraocular pressure was checked weekly. The observed retention rate is plotted and illustrated in FIG. 9. In the study as well as in the present application, the retention rate is defined as the percentage of eyes that retains implants over a certain period of time. As indicated by the plot in FIG. 9, the selected exemplary embodiments of the present application achieves higher retention rates than the modified commercial implants. For example, while the retention rate of the modified commercial implants declines to a rate below 60% in week three, the retention rate of the selected exemplary embodiments of the present application maintains at a relatively higher rate, approximately 95% or more, over the entire clinical trial. Having higher retention rate over a longer period of time is one of various advantages of embodiments of the present application.

The above detailed description is intended to be illustrative, and not restrictive. For example, the above-described examples (or one or more features thereof) may be used in combination with each other. As an example, one or more dimensions from the various implant embodiments shown or described may be grouped together to form an implant embodiment capable of providing a desired drug concentration. Other embodiments may be used, such as by one of ordinary skill in the art upon reviewing the above description. Also, in the above Detailed Description, various features may be grouped together to streamline the disclosure. This should not be interpreted as intending that an unclaimed disclosed feature is essential to any claim. Rather, inventive subject matter may be in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

What is claimed is:

1. A method of using an implant for insertion into a lacrimal canaliculus, comprising:
   placing the implant into the lacrimal canaliculus, wherein the implant comprises;
   a first member defining a first axis and having a first end along the first axis, wherein the first member is configured to extend into the canaliculus;
   a second member defining a second axis and having a second end along the second axis, wherein the second member is configured to reside in a vertical portion of the canaliculus and to extend to an opening of, or out of the opening of, an associate lacrimal punctum;
   a third member connecting the first end of the first member and the second end of the second member at a first angle to form an angled intersection; the third member comprises a bore defining a third axis and a second angle and having an upper surface;
   wherein the bore is configured to be accessible to an insertion tool for facilitating insertion of the implant and extends from the upper surface into the third member; and further wherein the first angle is defined by the first axis with respect to the second axis and the second angle is defined by the first axis with respect to the third axis;
   wherein the first angle is from 30 degrees to 150 degrees;
   wherein the second angle is from 15 degrees to 90 degrees.

2. The method of claim 1, wherein the implant is made of a material selected from the group consisting of: plastic, rubber, polymer and a composite.

3. The method of claim 1, wherein the first angle is from about 75 degrees to about 105 degrees.

4. The method of claim 1, wherein the first member comprises an intermediate segment, a tip segment and a forward segment in between the intermediate segment and the tip segment.

5. The method of claim 4, wherein the forward segment is tapered and has a conical shape, such that the forward segment connects the intermediate segment at one end and the tip segment at the other end.

6. The method of claim 4, wherein the intermediate segment has a cylindrical shape.

7. The method of claim 4, wherein the tip segment is substantially a semi-sphere or a portion of a semi-sphere.

8. The method of claim 4, wherein the length of the intermediate segment is from about 0.5 mm to about 3.5 mm; a radius of the tip segment is from about 0.05 mm to about 0.3 mm; and the length of forward segment is from about 1.0 mm to 5.0 mm.

9. The method of claim 1, wherein the bore extends from an upper surface into the third member and the upper surface extends beyond the intersection with the second member.

10. The method of claim 1, wherein the third member comprises a heel connecting segment configured to couple the third member to the first member, wherein a width of the heel connecting segment in the direction of the second axis varies along the direction of the first axis.

11. The method of claim 1, wherein the second angle is about 45 degrees.

12. The method of claim 1, wherein the bore has a depth along the direction of the third axis that is from about 0.3 mm to about 0.7 mm.

13. The method of claim 1, wherein the implant further comprises a cavity that is configured to house a therapeutic agent core.

14. The method of claim 13, wherein the implant is formatted as a unit dosage of an antiglaucoma agent.

15. The method of claim 14, wherein the antiglaucoma agent is a prostaglandin or prostaglandin analogue.

16. The method of claim 13, wherein the implant further comprises the therapeutic agent core comprising a therapeutic agent and a matrix, and the method further comprises administering a therapeutic agent to an eye.

17. The method of claim 16, wherein the therapeutic agent core comprises a therapeutic agent selected from anti-inflammatory agents, anti-fungal agents, anti-viral agents, anti-glaucoma drugs, anti-microbial agents, and steroidal compounds.

18. A method of using an implant for insertion into a lacrimal canaliculus, comprising:
   placing the implant into the lacrimal canaliculus, wherein the implant comprises;
   a first member defining a first axis and having a first end along the first axis, wherein the first member is configured to extend into the canaliculus;
   a second member defining a second axis and having a second end along the second axis, wherein the second member is configured to reside in a vertical portion of the canaliculus and to extend to an opening of, or out of the opening of, an associate lacrimal punctum;
   a cavity that is configured to house a therapeutic agent core, wherein the cavity extends into the second member along the second axis;
   a third member connecting the first end of the first member and the second end of the second member at a first angle to form an angled intersection; the third member comprises a bore defining a third axis and a second angle and having an upper surface;
   wherein the bore is configured to be accessible to an insertion tool for facilitating insertion of the implant and extends from the upper surface into the third member; and further wherein the first angle is defined by the first axis with respect to the second axis and the second angle is defined by the first axis with respect to the third axis;
   wherein the first angle is from 30 degrees to 150 degrees;
   wherein the second angle is from 15 degrees to 90 degrees.

19. The method of claim 18, wherein the implant further comprises the therapeutic agent core comprising a therapeutic agent and a matrix, and the method further comprises administering a therapeutic agent to an eye.

20. The method of claim 19, wherein the therapeutic agent core comprises a therapeutic agent selected from anti-inflammatory agents, anti-fungal agents, anti-viral agents, anti-glaucoma drugs, anti-microbial agents, and steroidal compounds.

21. The method of claim 20, wherein the antiglaucoma agent is a prostaglandin or prostaglandin analogue.

22. The method of claim 18, wherein the cavity comprises a depth from about 0.2 mm to about 1.4 mm.

23. The method of claim 18, wherein the first member comprises an intermediate segment, a tip segment and a forward segment in between the intermediate segment and the tip segment.

24. The method of claim 23, wherein the forward segment is tapered and has a conical shape, such that the forward segment connects the intermediate segment at one end and the tip segment at the other end.

25. The method of claim 23, wherein the intermediate segment has a cylindrical shape.

26. The method of claim 23, wherein the tip segment is substantially a semi-sphere or a portion of a semi-sphere.

27. The method of claim 23, wherein the length of the intermediate segment is from about 0.5 mm to about 3.5 mm; a radius of the tip segment is from about 0.05 mm to about 0.3 mm; and the length of forward segment is from about 1.0 mm to 5.0 mm.

28. The method of claim 18, wherein the bore extends from an upper surface into the third member and the upper surface extends beyond the intersection with the second member.

29. The method of claim 18, wherein the third member comprises a heel connecting segment configured to couple the third member to the first member, wherein a width of the heel connecting segment in the direction of the second axis varies along the direction of the first axis.

30. The method of claim 18, wherein the second angle is about 45 degrees.

\* \* \* \* \*